United States Patent
Yohannes et al.

(10) Patent No.: US 12,287,341 B2
(45) Date of Patent: Apr. 29, 2025

(54) ASSAYS AND METHODS FOR TARGETED TREATMENT OF HYDROSALPINX

(71) Applicant: GOVERNMENT OF THE UNITED STATES, AS REPRESENTED BY THE SECRETARY OF THE ARMY, Fort Detrick, MD (US)

(72) Inventors: Elizabeth H. Yohannes, University Place, WA (US); Avedis A. Kazanjian, Olympia, WA (US); Richard O. Burney, University Place, WA (US)

(73) Assignee: GOVERNMENT OF THE UNITED STATES, AS REPRESENTED BY THE SECRETARY OF THE ARMY, Fort Detrick, MD (US)

( * ) Notice: Subject to any disclaimer, the term of this patent is extended or adjusted under 35 U.S.C. 154(b) by 9 days.

(21) Appl. No.: 17/879,330

(22) Filed: Aug. 2, 2022

(65) Prior Publication Data
US 2023/0176073 A1    Jun. 8, 2023

Related U.S. Application Data

(62) Division of application No. 16/352,683, filed on Mar. 13, 2019, now abandoned.

(60) Provisional application No. 62/642,378, filed on Mar. 13, 2018.

(51) Int. Cl.
G01N 33/68 (2006.01)

(52) U.S. Cl.
CPC ..... *G01N 33/6893* (2013.01); *G01N 2333/46* (2013.01); *G01N 2333/4704* (2013.01); *G01N 2333/90283* (2013.01); *G01N 2333/91177* (2013.01); *G01N 2800/367* (2013.01)

(58) Field of Classification Search
None
See application file for complete search history.

(56) References Cited

U.S. PATENT DOCUMENTS

| | | |
|---|---|---|
| 2007/0208213 A1* | 9/2007 | Swann .................. A61F 6/225 600/33 |
| 2010/0227335 A1 | 9/2010 | Baker et al. |
| 2010/0227343 A1 | 9/2010 | Cheek et al. |
| 2014/0147867 A1 | 5/2014 | Arnold et al. |
| 2016/0041153 A1 | 2/2016 | Brown et al. |
| 2018/0188257 A1 | 7/2018 | Moore et al. |

FOREIGN PATENT DOCUMENTS

| | | | | |
|---|---|---|---|---|
| WO | 2013023994 A1 | | 2/2013 | |
| WO | WO 2013/023994 | * | 2/2013 | ........... G01N 33/574 |
| WO | 2018170325 A1 | | 9/2018 | |

OTHER PUBLICATIONS

Yohannes et al., Reproductive Sciences vol. 26, Supplement 1, Mar. 2019 Abstract S-032, p. 309A (Year: 2019).*
Lindsay et al., Reproductive Sciences, 24, Supplement 1, Mar. 2017, Abstract O-152 (Year: 2017).*
Tsang et al., Nature Communications, 2014; 5: 3446, doi: 10.1038/ncomms4446 (Year: 2014).*
Aboulghar, M.A. et al., "Controversies in the modern management of hydrosalpinx", Human Reproduction Update, 1998, vol. 4, No. 6, pp. 882-890.
Ajonuma, Louis Chuckwuemka et al., "New insights into the mechanism underlyring hydrosalpinx fluid formation and its adverse effect on IVF outcome", Human Reproduction Update, 2002, vol. 8, No. 3, pp. 255-264.
American Society for Reproductive Medicine, "Role of tubal surgery in the era of assisted reproductive technology: a committee opinion", Fertil Steril, 2012, vol. 97, pp. 539-545.
American Society for Reproductive Medicine, "Salpingectomy for hydrosalpinx prior to in vitro fertilization", Fertil Steril, 2008, vol. 90, pp. S66-S68.
Bedaiwy, Mohamed A. et al., "Relationship between oxidative stress and embryotoxicity of hydrosalpingeal fluid", Human Reproduction, 2002, vol. 17, No. 3, pp. 601-604.
Bera, Tapan K. et al., "Mesothelin is Not Required for Normal Mouse Development or Reproduction", Molecular and Cellular Biology, Apr. 2000, vol. 20, No. 8, pp. 2902-2906.
Campion, Edward W., "Pelvic Inflammatory Disease", The New England Journal of Medicine, May 21, 2015, vol. 372, No. 21, pp. 2039-2048.
Calogero, Aldo E. et al., "Conservative Nonhormonal Options for the Treatment of Male Infertility: Antibiotics, Anti-Inflammatory Drugs, and Antioxidants", BioMed Research International, 2017, vol. 2017, article ID 4650182, 17 pages.
Camus, E. et al., "Pregnancy rates after in-vitro fertilization in cases of tubal infertility with and without hydrosalpinx: a meta-analysis of published comparative studies", Human Reproduction, 1999, vol. 14, No. 5, pp. 1243-1249.

(Continued)

*Primary Examiner* — Christina M Borgeest
(74) *Attorney, Agent, or Firm* — Timothy H. Van Dyke; Wolter Van Dyke Davis, PLLC

(57) ABSTRACT

A method including detecting a presence of at least one analyte in a sample from a subject wherein the at least one analyte is selected from the group consisting of: mesothelin, Galectin-3-binding protein, Clusterin, Polymeric immunoglobulin receptor, Neutrophil gelatinase-associated lipocalin, Leucine-rich alpha-2-glycoprotein, Osteopontin, Alpha-amylase 1, WAP four-disulfide core domain protein 2, Mucin-16, GSTP1, PRDX5, TXN, PRDX6, and SOD1, and determining the subject has hydrosalpinx if the sample comprises an increased level of mesothelin, Galectin-3-binding protein, Clusterin, Polymeric immunoglobulin receptor, Neutrophil gelatinase-associated lipocalin, Leucine-rich alpha-2-glycoprotein, Osteopontin, Alpha-amylase 1, WAP four-disulfide core domain protein 2, and/or Mucin-16 relative to a control, and/or a decreased level of GSTP1, PRDX5, TXN, PRDX6, and/or SOD1, relative to the control, is provided herein. The method may further include if the subject is determined to have hydrosalpinx, administering a hydrosalpinx therapy to the subject.

2 Claims, 18 Drawing Sheets

(56) References Cited

OTHER PUBLICATIONS

Chang, Kai et al., "Molecular cloning of mesothelin, a differentiation antigen present on mesothelium, mesotheliomas, and ovarian cancers", Proc. Natl. Acad. Sci., Jan. 1996, vol. 93, pp. 136-140.

Cheever, Martin A. et al., "The Prioritization of Cancer Antigens: A National Cancer Institute Pilot Project for the Acceleration of Translational Research", Clin Cancer Res., Sep. 1, 2009, vol. 15, No. 17, pp. 5323-5337.

Creagh, EM et al., "Heat shock proteins—modulators of apoptosis in tumour cells", Leukemia, 2000, vol. 14, pp. 1161-1173.

Draftary, Gaurang S. et al., "Salpingectomy increases peri-implantation endometrial HOXA10 expression in women with hydrosalpinx", Fertility and Sterility, Feb. 2007, vol. 87, No. 2, pp. 367-372.

Draftary, Gaurang S. et al., "Hydrosalpinx fluid diminishes endometrial cell HOXA10 expression", Fertility and Sterility, Sep. 2002, vol. 78, No. 3, pp. 577-580.

Fezeli, Alireza et al., "Sperm-Induced Modification of the Oviductal Gene Expression Profile After Natural Insemination in Mice", Biology of Reproduction, 2004, vol. 71, pp. 60-65.

Fischer, Bernard M. et al., "Neutrophil Elastase Induces MUC5AC Gene Expression in Airway Epithelium via a Pathway Involving Reactive Oxygen Species", American Journal of Respiratory Cell and Molecular Biology, 2002, vol. 26, pp. 447-452.

Gaipl, US et al., "Complement binding is an early feature of necrotic and a rather late event during apoptotic cell death", Cell Death and Differentiation, 2001, vol. 8, pp. 327-334.

Gardner, David K. et al., "Environment of preimplantation human embryo in vivo: metabolite analysis of oviduct and uterine fluids and metabolism of cumulus cells", Fertility and Sterility, 1996, vol. 65, No. 2, Feb. 1996.

Georgiou, A. Stephen et al., "Gametes Alter the Oviductal Secretory Proteome", Molecular & Cellular Proteomics, 2005, vol. 4, pp. 1785-1796.

Hammadieh, Nahed et al., "Ultrasound-guided hydrosalpinx aspiration during oocyte collection improves pregnancy butcome in IVF: a randomized controlled trial", Human Reproduction, 2008, vol. 23, No. 5, pp. 1113-1117.

Hassan, Raffit et al., "Mesothelin: A New Target for Immunotherapy", Clinical Cancer Research, Jun. 15, 2004, vol. 10, pp. 3937-2942.

Hassan, Raffit et al., "Phase 1 Study of the Antimesothelin Immunotoxin SS1P in Combination With Pemetrexed and Cisplatin for Front-Line Therapy of Pleural Mesothelioma and Correlation of Tumor Response With Serum Mesothelin, Megakaryocyte Potentiating Factor, and Cancer Antigen 125", Cancer, Nov. 2014. 01, vol. 120, No. 21, pp. 3311-3319.

Hassan, Raffit et al., "Phase II clinical trial of amatuximab, a chimeric anti-mesothelin antibody with pemetrexed and cisplatin in advanced unresectable pleural mesothelioma", Clin Cancer Res., Dec. 1, 2014, vol. 20, No. 23, pp. 5927-5936.

Johnson, N. et al., "Surgical treatment for tubal disease in women due to undergo in vitro fertilisation (Review)", Cochrane Database of Systematic Reviews, 2010, issue 1, Art. No. CD002125, 57 pages.

Jones, J et al., "Apoptosis is associated with reduced expression of complement regulatory molecules, adhesion molecules and other receptors on polymorphonuclear leucocytes: functional relevance and role in inflammation", Immunology, 1995, vol. 86, pp. 651-660.

Kabakov, A.E. et al., "Pharmacological attenuation of apoptosis in reoxygenated endothelial cells", CMLS, Cell. Mol. Life Sci., 2004, vol. 61, pp. 3076-3086.

Koga, Takeshi et al., "TNF-a induces MUC1 gene transcription in lung epithelial cells: its signaling pathway and biological implication", Am J Physiol Lung Cell Mol Physiol., 2007, vol. 293, pp. L693-L701.

Koski, Carol L. et al., "Cytolysis of nucleated cells by complement: Cell death displays multi-hit characteristics", Proc. Natt Acad. Sci. USA, Jun. 1983, vol. 80, pp. 3816-3820.

Kreitman, Robert J. et al., "Phase I Trial of Continuous Infusion Anti-Mesothelin Recombinant Immunotoxin SS1P", Clin Cancer Res. Aug. 1, 20095, vol. 15, No. 16, pp. 5274-5279.

Kufe, Donald W., "Mucins in cancer: function, prognosis and therapy", Nat Rev Cancer, Dec. 2009, vol. 9, No. 874-885.

Kuwahara, Ippei et al., "Neutrophil elastase stimulates MUC1 gene expression through increased Sp1 binding to the MUC1 promoter", Am J Physiol Lung Cell Mol Physiol., 2005, vol. 289, pp. L355-L362.

Lane, Michelle., "Embryo culture medium: which is the best?" Best Practice & Research Clinical Obstetrics and Gynaecology, 2007, vol. 21, No. 1, pp. 83e100.

Lapointe, Jerome et al., "Antioxidant Defenses Are Modulated in the Cow Oviduct During the Estrous Cycle", Biology of Reproduction, 2003, vol. 68, pp. 1157-1164.

Leng, Z. et al., "Characterization of ciliary activity in distal Fallopian tube biopsies of women with obstructive tubal Infertility", Human Reproduction, 1998, vol. 13, No. 11, pp. 3121-3127.

Love, Michael et al., "Moderated estimation of fold change and dispersion for RNA-seq data with DESeq2", Genome Biology, 2014, vol. 15, No. 550, 21 pages.

Matsuoka, Itsuko et al., "Impact of erythrocytes on mouse embryonal development in vitro", FEBS Letters, 1995, vol. 371, pp. 297-299.

Merle, Nicolas S. et al., "Complement system part i—molecular mechanisms of activation and regulation", Front. Immunol, 2015, vol. 6, No. 262, 30 pages.

Merle, Nicolas S. et al., "Complement system part ii: role in immunity", Immunol, 2015, vol. 6, No. 257, 26 pages.

Morgan, B.P. et al., "Extrahepatic complement biosynthesis: where, when and why?" Clin. Exp. Immunol., 1997, vol. 107, pp. 1-7.

Murphy, Ana A. et al., "Evidence for oxidat!vely modified lipidprotein complexes in endometrtum and endometriosis", Fertility and Sterility, Jun. 1998, vol. 69, No. 6, pp. 1092-1094.

Onda, Masanori et al., "Megakaryocyte Potentiation Factor Cleaved from Mesothelin Precursor is a Useful Tumor Marker in the Serum of Patients with Mesothelioma", Clin Cancer Res., 2006, vol. 12, No. 14, pp. 4225-4231.

Pannala, Venkat R. et al., "Mechanistic Characterization of the Thioredoxin System in the Removal of Hydrogen Peroxide", Free Radic Biol Med., Jan. 2015, vol. 78, pp. 42-55.

Pastan, Ira et al., "Discovery of Mesothelin and Exploiting it as a Target for Immunotherapy", Cancer Res., Jun. 1, 2014, vol. 74, No. 11, pp. 2907-2912.

Patil, Madhuri, "Assessing tubal damage", J Hum Reprod Scie, Jan.-Jun. 2009, vol. 2, issue 1, 10 pages.

Ricklin, Daniel et al., "Complement—a key system for immune surveillance and homeostasis", Nat Immunol., Sep. 2010, vol. 11, No. 9, pp. 785-797.

Roca, Jordi et al., "Survival and In Vitro Fertility of Boar Spermatozoa Frozen in the Presence of Superoxide Dismutase and/or Catalase", Journal of Andrology, 2005, vol. 26, No. 1, pp. 15-24.

Rudd, Pauline M. et al., "The Glycosylation of the Complement Regulatory Protein, Human Erythrocyte CD59", The Journal of Biological Chemistry, 1997, vol. 272, No. 11, issue of Mar. 14., pp. 7229-7244.

Rump, Armin et al., "Binding of Ovarian Cancer Antigen CA125/MUC16 to Mesothelin Mediates Cell Adhesion", The Journal of Biological Chemistry, 2004, vol. 279, No. 10, issue of Mar. 5, pp. 9190-9198.

Sagoskin, Arthur W. et al., "Salpingectomy or proximal tubal occlusion of unilateral hydrosalpinx increases the potential for spontaneous pregnancy", Human Reproduction, 2003, vol. 18, No. 12, pp. 2634-2637.

Savaris, Ricardo Francalacci et al., "The Influence of Hydrosalpinx on Markers of Endometrial Receptivity", Semin Reprod Med., 2005, vol. 25, pp. 476-482.

Andersen, Anders Nyboe et al., "Low implantation rate after in-vitro fertilization in patients with hydrosalpinges diagnosed by ultrasonography", Human Reproduction, 1994, vol. 9, No. 10, pp. 1935-1938.

(56) References Cited

OTHER PUBLICATIONS

Chang, Kai et al., "Isolation and characterization of a monoclonal antibody, K1, reactive with ovarian cancers and hormal mesothelium", Int. J. Cancer, 1992, vol. 50, pp. 373-381.
Chanr, Louis Y. et al., "Hydrosalpinx fluid induced embryotoxicity and lipid peroxidation", Reproductive Toxicology, 2004, vol. 19, pp. 147-148.
Cohen, Steven D. et al., "Selective Protein Covalent Binding and Target Organ Toxicity", Toxicology and Applied Pharmacology, 1997, vol. 143, pp. 1-12.
Enss, M.L .et al., "Proinflammatory cytokines trigger MUC gene expression and mucin release in the intestinal cancer cell line LS180", Inflamm. res., 2000, vol. 49, pp. 162-169.
Fedele, L. et al., "Degree of Endosalpingeal Deciliation (By S.E.M.) in Hydrosalpinx is Not Prognostic for Post-Surgical Fertility", Acta Europaea Fertilitatis, 1984, vol. 15, No. 3, 7 pages.
Hassan, Raffit et al., "Localization of Mesothelin in Epithelial Ovarian Cancer", Appl Immunohistochem Mol Morphol, 2005, vol. 13, pp. 243-247.
Heinrich, Jorg-Christian et al., "RP101 (brivudine) binds to heat shock protein HSP27 (HSPB1) and enhances survival in animals and pancreatic cancer patients", J Cancer Res Clin Oncol, 2011, vol. 137, pp. 1349-1361.
Kolev, Martin et al., "Complement—tapping into new sites and effector systems", Immunology, Dec. 2014, vol. 14, pp. 811-820.
Lundgren, J.D. et al., "The effect of neutrophil protenase enzymes on the release of mucus from feline and human airway cultures", Repiratory Medicine, 1994, vol. 88, pp. 511-518.
Meri, Seppo et al., "Structural composition and functional characterization of soluble CD59: heterogeneity of the oligosaccharide and glycophosphoinositol (GPI) anchor revealed by laser-desorption mass spectrometric analysis", Biochem. J., 1996, vol. 316, pp. 923-935.
Rossi, Tiziana et al., "Improved human sperm recovery using superoxide dismutase and catalase supplementation in semen cryoprservation procedure", Cell and Tissue Banking, 2001, vol. 2, No. 1, pp. 9-13.
Smirnova, Marina G. et al., "Up-regulation of mucin secretion in HT29-MTX cells by the pro-inflammatory cytokines tumor necrosis factoe-x and interleukin-6", Eur. Cytokine Netw., Mar. 2001, vol. 12, No. 1, pp. 119-125.
Weinstock, C. et al., "CD59: A long-known complement inhibitor has advanced to a blood group system", Immunohematology, 2015, vol. 31, No. 4, pp. 145-151.
Zalel, Yaron et al., "Contribution of Color Doppler Flow to the Ultasonographic Diagnosis of Tubal Abdnormalities", J. Ultrasound Med., 2000, vol. 19, pp. 645-649.
Scholler, Nathalie et al., "Soluble member(s) of the mesothelinymegakaryocyte potentiating factor family are detectable in sera from patients with ovarian carcinoma", Proc. Natl. Acad. Sci., 1999, vol. 96, pp. 11531-11536.
Seli. Emre et al., "Removal of hydrosalpinges increases endometrial leukaemia inhibitory factor (LIF) expression at the time of the implantation window", Human Reproduction, 2005, vol. 20, No. 11, pp. 3012-3017.
Shao, Ruijin et al., "Coordinate regulation of heterogeneous nuclear ribonucleoprotein dynamics by steroid hormones in the human Fallopian tube and endometrium in vivo and in vitro", Articles in PresS. Am J Physiol Endocrinol Metab., Mar. 20, 2012, 33 pages.
Shao, Ruijin et al., "Distinct Expression Pattern of Dicer1 Correlates with Ovarian-Derived Steroid Hormone Receptor Expression in Human Fallopian Tubes during Ovulation and the Midsecretory Phase", J Clin Endocrinol Metab, May 2011, vol. 96, No. 5, pp. E869-E877.
Sirover, Michael A., "Subcellular Dynamics of Multifunctional Protein Regulation: Mechanisms of GAPDH Intracellular Translocation", J Cell Biochem., Jul. 2012, vol. 113, No. 7, pp. 2193-2200.
Sirover, Michael A., "On the functional diversity of glyceraldehyde-3-phosphate dehydrogenase: Biochemical mechanisms and regulatory control", Biochimica et Biophysica Acta, 2011, vol. 1810, pp. 741-751.
Song, Yong et al., "NF kappaB expression increases and CFTR and MUC1 expression decreases in the endometrium of infertile patients with hydrosalpinx: a comparative study", Reproductive Biology and Endocrinology, 2012, vol. 10, No. 86, 8 pages.
Strandell, Annika et al., "Why does hydrosalpinx reduce fertility?" Human Reproduction, 2002, vol. 17, No. 5, pp. 1141-1145.
Strandell, A., "The influence of hydrosalpinx on IVF and embryo transfer: a review", Human Reproduction Update, 2000, vol. 6, No. 4, pp. 387-395.
Vam Voorhis, Bradley J. et al., "Ultrasound-guided aspiration of hydrosalpinges is associated with improved pregnancy and implantation rates after in-vitro fertilization cycles", Human Reproduction, 1998, vol. 13, No. 3, pp. 736-739.
Demir, Melike et al., "Evaluation of New Biomarkers in the Prediction of Malignant Mesothelioma in Subjects with Environmental Asbestos Exposure", Lung, 2016, vol. 194, pp. 409-417.
Kaneko, Osamu et al., "A Binding Domain on Mesothelin for Ca 125/MUC16", The Journal of Biological Chemistry, Feb. 6, 2009, vol. 284, No. 6, pp. 3739-3749.
Sirois, Allison R. et al., "Fn3 proteins engineered to recognize tumor biomarker mesothelin internalize upon binding", Plos One, 2018, vol. 13, No. 5, 19 pages.

* cited by examiner

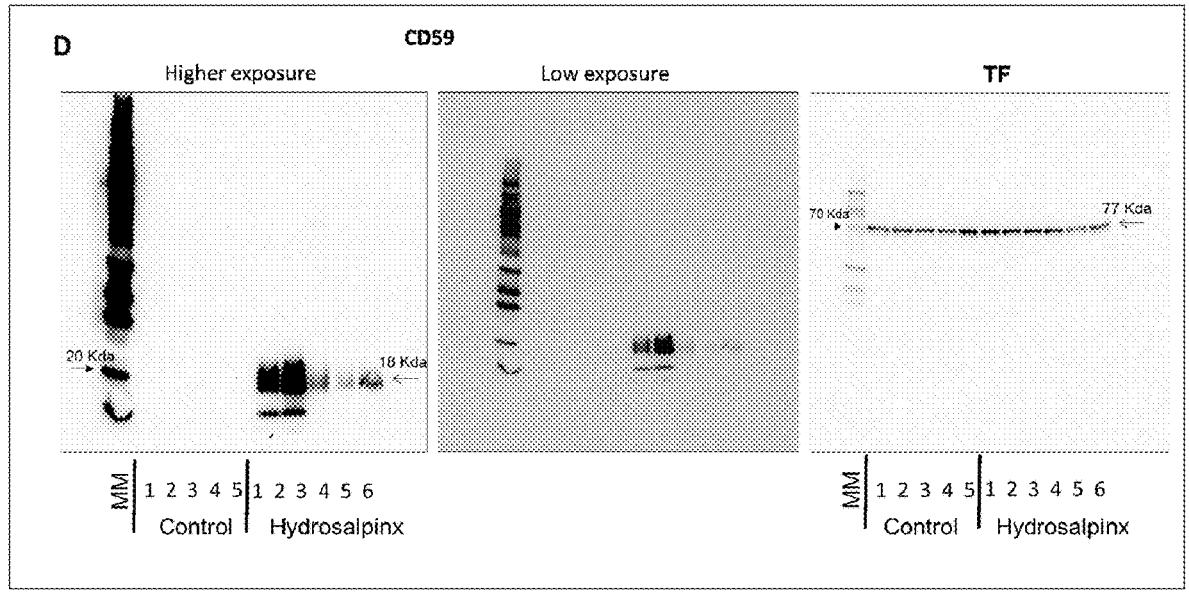
Figure 16
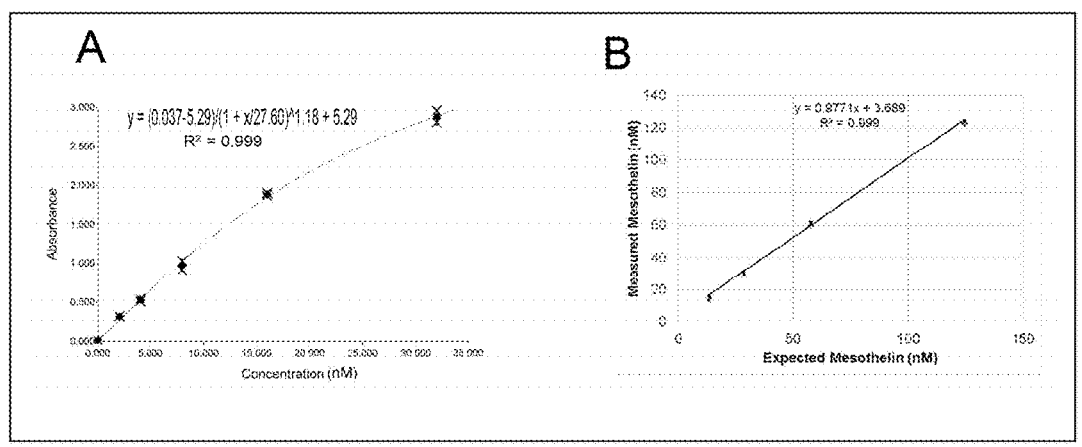

ASSAYS AND METHODS FOR TARGETED TREATMENT OF HYDROSALPINX

CROSS-REFERENCE TO RELATED APPLICATIONS

This application is a divisional of U.S. application Ser. No. 16/352,683 filed on Mar. 13, 2019 and claims priority to U.S. Provisional Application No. 62/642,378 filed Mar. 13, 2018 which is incorporated by reference in its entirety herein.

STATEMENT AS TO RIGHTS OR INVENTIONS MADE UNDER FEDERALLY SPONSORED RESEARCH AND DEVELOPMENT

This invention was made with government support from the Madigan Army Medical Center, a subordinate organization of the United States Department of Army. The United States Government has certain rights in the invention.

BACKGROUND

Hydrosalpinx is a significant long-term complication of pelvic inflammatory disease (PID). It is usually a result of fallopian tube damage and distal adhesion formation subsequent to PID leading to distally blocked fallopian tubes that are enlarged and filled with fluid. Despite declining rates of PID in North America and Western Europe, it remains a problematic disease process because of its impact on reproductive health (1). Many women with PID experience a subclinical course, resulting in delayed or no treatment. However, even those women who do receive the Center for Disease Control (CDC) recommended treatment upon diagnosis report infertility, ectopic pregnancy, and chronic pelvic pain. Those with recurrent PID have an almost two-fold increase in infertility (1). In addition to the impact of distal tubal occlusion, PID results in decreased ciliation and ciliary dyskinesia of the endosalpinx (2). Even when tubal patency is reestablished following surgical correction of distal tubal occlusion, intrauterine pregnancy rates remain low while ectopic pregnancy rates increased. These rates are further impacted by the degree of tubal damage secondary to hydrosalpinx (3).

Several clinical studies have shown detrimental effect of hydrosalpinx on IVF success rates. Two meta-analyses have validated the association between hydrosalpinx and poor IVF outcome via demonstrating 50% reduction in pregnancy, implantation, and delivery, while 2-fold increase in spontaneous abortion rate among women with hydrosalpinx (4, 5). Subsequent to these clinical observation, surgical removal of bilateral and unilateral hydrosalpinx, or proximal tubal occlusion have shown to resolve the deleterious impact of hydrosalpinx and improved IVF assisted pregnancy rates (6-8). In addition, transvaginal aspiration of the hydrosalpnix fluid has improved IVF assisted pregnancy rate (9, 10). Despite there is unambiguous negative impact of hydrosalpinx fluid and clear benefit to its surgical removal or transvaginal aspiration, the mechanism by which hydrosalpinx mediate pathogenesis at the molecular level remain poorly understood.

Given the prevalence of pelvic inflammatory disease and associated complications such as hydrosalpinx, procedures for infertility generally include an assessment of tubal patency which can be investigated with hysterosalpingography and/or laparoscopy. Hydrosalpinx can be reliably detected with these diagnostic tests, however, they are expensive, invasive, and not without risk. A 2011 National Institutes of Health Workshop identified research needs related to the diagnosis, treatment, and prevention of PID. Accurate diagnosis and treatment of hydrosalpinx is essential to the future success of both spontaneous and IVF pregnancies. Thus, the development of a less invasive, diagnostic approach for the diagnosis of hydrosalpinx is needed.

BRIEF DESCRIPTION OF THE DRAWINGS

FIG. 7A shows immunohistochemistry related to mesothelin. FIG. 7B shows a zoomed in view of the box in FIG. 7A. FIG. 7C shows immunohistochemistry related to mesothelin. FIG. 7D shows a zoomed in view of the box of FIG. 7C. FIG. 7E shows immunohistochemistry related to CD45. FIG. 7F shows a zoomed in view of the box of FIG. 7E. FIG. 7G shows immunohistochemistry related to CD45. FIG. 7H shows a zoomed in view of the box of FIG. 7G.

FIG. 15 A shows full length images for SOD1 and GSTP1 and TF. FIG. 15B shows full length image for TXNRD1 and TXN with high contrast (left) and low contrast (right). FIG. 15C shows full length images for MSNL and TF. FIG. 15D shows CD59 with higher and lower magnification along with TF.

FIG. 16A shows graphical representations of a standard curve for human mesothelin and FIG. 16B shows results from a linearity study of mesothelin in plasma from women with hydrosalpinx.

BRIEF DESCRIPTION OF THE TABLES

Figure 1:
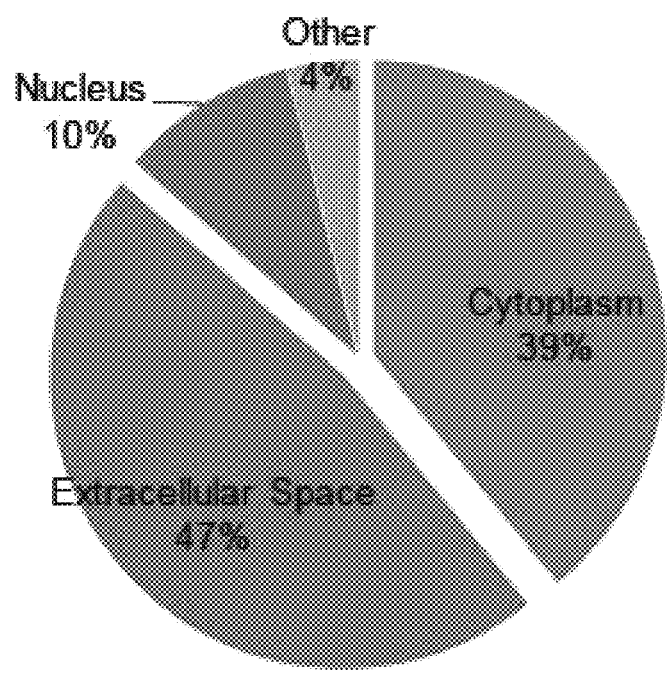
FIG. 1 is a pie chart showing cellular localization for non-redundant proteins identified with shotgun label free proteomics analysis.

Table 1: Relative fold changes for the selected proteins determine from verification western blot analysis of hydrosalpinx and healthy control tubal lavages.

Table 2: Patient Information for fallopian tube aspirates (hydrosalpinx) and lavages (from fertile controls undergoing tubal re-anastomosis). A total of 26 independent samples were used for shotgun proteomics. The additional independent control samples were used for western blot verification analysis presented in FIGS. 4B and C.

Table 3: Differential proteome profile of tubal fluids from subjects with hydrosalpinx relative to lavages from healthy fertile donors.

DETAILED DESCRIPTION

Introduction

Embodiments of the invention relate to the accurate determination of certain biomarkers in bodily fluid or tissue samples from a subject. Monitoring of important biomarkers of disease is useful in preventing unnecessary test and treatments, such as IVF for patients suffering from infertility when the infertility is caused by inflammation or fluid filled pockets in the fallopian tube or surrounding tissues of the patient, and a diagnosis of hydrosalpinx and treatment thereof would be less invasive, save time, and reduce cost for patients.

Accordingly, embodiments of the present invention provide assays and methods for detecting the presence of hydrosalpinx biomarkers, in qualitative and quantitative form, in a biological sample. These assays and methods can be used to test for these biomarkers in any fluid taken from the subject, but preferably test for biomarkers of hydrosalpinx in a blood sample taken from the patient.

By using embodiments of the invention, unnecessary treatment rates and unnecessary risk associated with alternative infertility treatments, such as IVF for example, would reduce cost and complications or side effects, and increase quality of life for the patient.

Overview

Fallopian tube fluid is a complex mixture of components secreted from the epithelial cells and blood plasma to support early embryo development. Though human fallopian tube secretome changes across the menstrual cycle have not been well described, much has been inferred from animal studies, which has contributed to the development of cleavage stage embryo culture media (18-20). The fallopian tube is supported by a rich mesosalpingeal vasculature such that intratubal molecular alterations like those occurring in hydrosalpinx may be testable in the plasma. However, tubal secretome such as proteome are not well described neither in healthy human tubal fluid nor those with hydrosalpinx partly due to the inherent difficulty of collecting these bio-specimens.

Herein, a discovery label-free shotgun proteomics was carried out to identify proteome abundance differences in hydrosalpinx fluid compared to normal tubal lavages from fertile controls. This analysis provided several proteins of interest in the hydrosalpinx, and some of these proteins detected directly by shotgun proteomics were validated by western blotting and immunohistochemistry. To leverage the protein abundance changes, differentially expressed proteins were identified as inputs for bioinformatics analysis of pathways and bioprocesses that are likely involved in the disease process. This analysis uncovered significantly dysregulated pathways and bioprocesses due to hydrosalpinx. With these integrated approaches, hydrosalpinx biomarkers and proteins that provide valuable mechanistic insight, which are precursors to and/or responsible for hydrosalpinx induced tubal damages and/or impaired IVF successes have been identified.

There currently exists an unmet need in the art for methods for determining the presence and levels of biomarkers for detecting hydrosalpinx in a patient. The present invention provides useful embodiments for aspects of such determination, including sample collection and testing, as well as methods useful in assisting appropriate diagnosis and treatment of patient suffering from this condition.

Infertility diagnoses are growing, and hydrosalpinx has been found to cause at least temporary infertility in some patients. Treatment for hydrosalpinx in these patients results in regained fertility. Consequently, the typically subsequent step of fertility treatments, including, for example IVF, is unnecessary upon early identification of and treatment for hydrosalpinx in patients suffering therefrom.

Definitions

The following terms as used herein have the following definitions. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, because measurements are subject to inherent variability, any temperature, weight, volume, time interval, pH, salinity, molarity or molality, range, concentration and any other measurements, quantities or numerical expressions given herein are intended to be approximate and not exact or critical figures, unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount. The terms front, back and side are only used as a frame of reference for describing components herein and are not to be limiting in any way.

The terms "first," "second," and the like, as used herein, do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context. All ranges disclosed within this specification are inclusive and are independently combinable. Furthermore, to the extent that the terms "including," "includes," "having," "has," "with," or variants thereof are used in either the detailed description and/or the claims, such terms are intended to be inclusive in a manner similar to the term "comprising." The terms front, back and side are only used as a frame of reference for describing components herein and are not to be limiting in any way.

The term "analyte" refers to any compound or composition to be measured in an assay, for example a biomarker or a portion thereof. Such an analyte also is referred to as a target or target analyte, and is capable of binding specifically to a capture molecule, which can be an antigen, hapten, protein, drug, metabolite, nucleic acid, ligand, receptor, enzyme, aptamer, antibody or fragment thereof, affibody, affimer, avimer, aptamer, aptide, cell, or cytokine. Preferably, the analyte is mesothelin or a portion thereof, such as an epitope or hapten thereof. Analytes also can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity.

The term "antibody" is used here in its broadest sense refers to an immunoglobulin, or fragment or active fragment thereof, or antibody substitutes. The antibody can be monoclonal or polyclonal and can be prepared by techniques that are well known in the art such as, for example, immunization of a host and collection of sera or hybrid cell line technology, or recombinant technology. The term includes monoclonal antibodies, polyclonal antibodies, anti-idiotypic antibodies, synthetic antibodies, multispecific antibodies (e.g., bispecific antibodies) formed from at least two intact antibodies, and antibody fragments so long as they exhibit the desired binding activity. The antibodies can be chimeric antibodies, including humanized antibodies as described in Jones et al., Nature 321:522-525, 1986, Riechmann et al., Nature 332:323-329, 1988, Presta, Curr. Opin. Struct. Biol. 2:593-596, 1992, Vaswani and Hamilton, Ann. Allergy, Asthma & Immunol. 1:105-115, 1998, Harris, Biochem. Soc. Transactions 23:1035-1038, 1995, and Hurle and Gross, Curr. Opin. Biotech. 5:428-433, 1994. Antibodies of any class or isotype (e.g., IgA, IgA1, IgA2, IgD, IgE, IgG, IgG1, IgG2, IgG3, IgG4, and IgM) can be used.

The term "antibody" also refers to any antibody fragment(s) that retain a functional antigen binding region. Examples of antibody fragments include Fab, Fab', F(ab')2, and Fv fragments; diabodies; linear antibodies; single-chain antibody molecules; and multispecific antibodies formed from antibody fragments, all of which are known in the art. Papain digestion of antibodies produces two identical antigen-binding fragments, called "Fab" fragments, each with a single antigen-binding site. Pepsin treatment yields an F(ab')2 fragment that has two antigen-combining sites and is still capable of cross-linking antigen. Fab' fragments differ from Fab fragments by the addition of a few residues at the carboxy terminus of the heavy chain CH1 domain including one or more cysteines from the antibody hinge region. F(ab')2 antibody fragments are pairs of Fab' fragments which have hinge cysteines between them. Other chemical couplings of antibody fragments are also known. "Fv" is the minimum antibody fragment which contains a complete antigen-binding site. Diabodies are described more fully in, for example, European Patent No. 404,097, International Patent Application WO 1993/01161, Hudson et al., Nat. Med. 9:129-134, 2003, and Hollinger et al., PNAS USA 90: 6444-6448, 1993. Triabodies and tetrabodies also are described in Hudson et al., Nat. Med. 9:129-134, 2003.

The term "antibody," also includes antibody substitutes or any natural, recombinant or synthetic molecule that specifically binds with high affinity and specificity to a particular target. Thus, the term "antibody" or the term "antibody substitute" includes such synthetic antibodies or antibody substitutes such as aptamers, affibodies, affimers, avimers, aptides, and the like. Therefore, when describing the assay systems, devices and methods according to embodiments of the invention here, use of the term "antibody" for use as, for example, a reagent in the assay, indicates any of these alternatives also can be used.

The term "aptamer" refers to a nucleic acid or peptide molecule that specifically binds to a molecule of interest (target) with high affinity and specificity. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target.

The term "biomarker" refers to an analyte that appears or increases or decreases in amount, as an indicator of or marker of a particular disease or condition. In particular, this term includes any naturally occurring and detectable biological molecule, the presence of which, or the modulation of their concentration (increase or decrease) in a subject or subject sample, indicates a hydrosalpinx condition. For example, mesothelin is an example of a biomarker that has been identified herein as being overabundant in hydrosalpinx patients. Other biomarkers contemplated as useful with the present invention include Galectin-3-binding protein, Clusterin, Polymeric immunoglobulin receptor, Neutrophil gelatinase-associated lipocalin, Leucine-rich alpha-2-glycoprotein, Osteopontin, Alpha-amylase 1, WAP four-disulfide core domain protein 2, Mucin-16, CD55, CD59, GSTP1, PRDX5, TXN, PRDX6, and SOD1. The term "biomarker" also can refer to any analyte used to determine the presence or degree of a hydrosalpinx-related disease or condition.

The term "control" or "healthy control" as used interchangeably herein in reference to any one of the methods of the invention defined may include one or more control(s) selected from: the level of analyte found in a healthy control sample from a healthy individual (i.e. individual without hydrosalpinx), a healthy analyte level; or a healthy analyte level range. Samples obtained from a subject to be tested may be compared to a control to determine if the level of an analyte is increased or decreased relative to the control.

A "hydrosalpinx control" used in any one of the methods of the invention defined herein may include one or more control(s) selected from: a level analyte found in a sample from a subject known to have hydrosalpinx, a hydrosalpinx analyte level or a hydrosalpinx analyte level range. Specific examples of a level of analyte found in a sample from a hydrosalpinx subject is found in Table 3.

The term "sample" refers to any acquired material to be tested for the presence or amount of an analyte. Preferably, a sample is a fluid sample, preferably a liquid sample. Examples of liquid samples that may be tested using an assay described in embodiments herein, include bodily fluids including blood, fallopian tube or "tubal" fluid, blood, serum, vaginal fluid, plasma, saliva, urine, and spinal fluid. The term "sample" also includes material that has been collected from a subject and treated further, for example solubilized or diluted in a solvent suitable for testing.

The term "reagent" refers to a molecule that is used to detect a target analyte, including reagents that bind to the target (e.g. a capture molecule for mesothelin), agents that bind to the capture molecule, detectably labeled reagents and the like. Reagents are molecules typically involved in assays described herein.

The terms "capture molecule" or "capture reagent" are used interchangeably herein to refer to an antibody or antibody substitute that specifically binds to the target analyte to be detected. The capture reagent may include a detectable label associated therewith.

The term "hydrosalpinx therapy" refers to any treatment or method used to cure or treat, either partially or completely, hydrosalpinx or infertility caused by hydrosalpinx in a subject. Examples of therapies may include sclerotherapy, surgical removal or excision of all or a part of a fallopian tube, dilating the obstructed lumen, i.e., fallopian tube with a balloon catheter or other mechanism, removal of any peritubal or other adhesions in the fallopian tube, laser treatment of all or a portion of the anatomy to remove an adhesion or otherwise treat hydrosalpinx, treatment of any illness or cause of the onset of hydrosalpinx, for example, treatment or prevention of an infection, such as a chlamydial infection or any other infection or disease which may lead to hydrosalpinx.

The term "fertility treatment" pertains to a treatment designed to increase incidence of successful pregnancy. Examples of a fertility treatment include in vitro fertilization (IVF), fertility drug administration, intrauterine insemination (IUI), intracytoplasmic sperm injection (ICSI), gamete intrafallopian transfer (GIFT), and/or zygote intrafallopian transfer (ZIFT)

The terms "subject" and "patient" are used interchangeably herein. The term "subject refers to an animal, preferably a mammal such as a non-primate and primate (e.g., monkey and human" and most preferably a human of the female gender. A target subject may include a subject to which the assays, methods and treatments herein are targeted to, which may include, in a non-limiting embodiment, a human of the female gender of approximately 40 years of age or younger. In a more specific embodiment, the subject is 35 years or younger, or 30 years or younger.

The invention is described herein with reference to specific embodiments thereof. Various modifications and changes, however, can be made to the invention without departing from the broader spirit and scope of the invention. The specification and drawings are, accordingly, illustrative rather than restrictive. Throughout this specification and the claims, unless the context requires otherwise, the word "comprise" and its cognates, such as "comprises" and "comprising," imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Assays

Assays according to the invention are biochemical tests that detect, in a specific and qualitative, semi-quantitative or quantitative manner, the presence of a target analyte in a sample. Specific binding assays of this type rely on the ability of a specific-binding "capture" molecule to bind to the target analyte to be detected or measured without appreciable binding to any other component of a complex sample containing numerous other macromolecules. Commonly, these types of tests are referred to as ligand binding tests, or, for example, immunoassays. A detection method is used to determine the presence and extent of the binding which occurs, therefore the assay involves a label or other means to produce a detectable or measurable signal in response to this binding. Many different labels or other mechanisms are available to permit detection of the signal through different means, such as detection of radiation, color change or intensity, fluorescence, chemiluminescence, enzyme activity, physical agglutination or clumping, and the like. Steps in a typical assay of this type usually involve (1) sample collection and preparation; (2) analyte capture; and (3) detection. Examples of assays that may be implemented to detect analytes useful in accord with the assay and method embodiments herein are further described below.

Sample collection can be performed according to any of the methods known in the art for collecting a bodily fluid, cellular, tissue or other sample. Any sample which contains or is suspected of containing the target analyte to be detected in the assay can be used. Samples can be taken from any subject, including human and animal subjects such as companion animals, laboratory animals, or livestock. Suitable subjects include, but are not limited to humans, simians, mice, rats, rabbits, dogs, cats, horses, cattle, sheep, and the like.

Fluid (liquid, semi-liquid, gelatinous, and the like) samples commonly are be collected by aspiration using a needle or collection in a vessel or by swab. Fluid samples optionally are treated prior to assay by, for example, mixing, filtration, dilution or serial dilution, or centrifugation (e.g., to remove cells, cellular debris, or other particulates) to produce a better or cleaner sample for assay. When the sample is a solid or semi-solid material, including but not limited to stool, biopsy or autopsy tissue samples, and the like, it optionally is treated by maceration or dissolution, for example.

Target analytes which can be detected using the systems and methods according to embodiments of the invention include any molecule for which a specific binding capture molecule can be found or made. Important analytes include nucleic acids, proteins, peptides, pharmaceuticals, hormones, biomarkers of disease, and the like. Most preferably, the analyte is a molecule of biomedical importance to diagnosis or treatment of a patient. In preferred embodiments, the analyte is of diagnostic significance, for example a biomarker, the presence of which indicates a disease or condition in the subject from whom the sample was taken. In some embodiments, if the analyte is a nucleic acid, the analyte in the sample optionally can be amplified by known methods of molecular biology such as PCR (polymerase chain reaction), or RT-PCR, prior to assay to increase the sensitivity of the method.

Capture of the analyte can be performed in solution or on a substrate using any convenient capture molecule. Most commonly, antibodies, such as polyclonal or monoclonal antibodies, or binding fragments thereof are used as the capture molecule, however any convenient capture molecule is suitable for use with the invention as long as it binds to the analyte specifically and with high affinity and specificity. Preferably, the capture molecule is able to bind the analyte at nanomolar concentrations or less, more preferably at picomolar or attomolar concentrations. Antibody substitute capture molecules such as aptamers, aptides, affibodies, affimers, avimers, and the like can serve as capture molecules, as well as receptors, specific binding partners, ligands, and the like.

Assays according to embodiments of the invention can be configured to operate in any convenient format known in the art. For example, the assay can be competitive or non-competitive, or a sandwich assay, and can be performed in solution (liquid phase) or on any of several known substrates. Some immunoassays can be carried out simply by mixing the reagents and sample and making a physical measurement, including newer "mix-and-measure" assays, which do not require the separation of bound from free ligand, for example bead-based assays. Such assays are called homogenous assays or less frequently non-separation assays. Multi-step assays are often called separation assays or heterogeneous assays. Commonly used assay types include radioimmune assays (RIA), immunoradiometric assays (IRA), enzyme-linked immunosorbant assays (ELISA), agglutination assays, precipitation or sedimentation assays, lateral flow (immuno) assays (LFIA), or blotting assays such as dot blots, western blots, and the like, each using any of the known capture molecules and detection systems. The assays according to embodiments of the invention can be automated using high throughput automatic analyzer instruments or robotic methods.

Many assays are named for the detection system which they employ, for example radioimmunoassays use a radioactive label, magnetic immunoassays use a magnet for separation, fluorescent immunoassays use a fluorescent label, while ELISA tests use an enzyme-substrate reaction to develop a detectable color. Fluorescent resonance energy transfer (FRET) systems and proximity ligation assays are other examples of assays that are described based on the detection system. Any of these assay types are contemplated for use with embodiments of the invention. Further description of detection methods is found below. Liquid phase ligand binding assays that rely on specifically binding capture molecules also include nucleic acid hybridization assays, which typically use an intercalating fluorescent dye that emits fluorescence via secondary structure conversion, molecular beacon capture of specific nucleic acid sequences, or real-time RT-qPCR using a molecular beacon or fluorophore intercalating dye.

A very simple form of assay is the "mix-and-measure" type or homogenous assay, in which the reagents are mixed together and the signal is read. Specific examples of such assays are described in, for example, Kreisig et al., Scientific Reports 4:5613, 2014; Miskolci et al., Meth. Mol. Biol. 1172:173-184, 2014; Wang et al., Biosensors and Bioelectronics 26(2):743-747, 2010; Luu et al., tech.co.jp/products/intellicyt/ique_screener/intellicyt_hybridoma.pdf; Edelhoch, H., Hayaishi, O., and Teply, L.: The Preparation and Properties of a Soluble Disphosphopyridine Nucleotide Cytochrome C Reductase, *J Biol Chem* 197, 97, 1952; Mahler, H., Sarkar, N., Vernon, L., and Alberty, R.: Studies on Diphosphopyridine Nucleotide-Cytochrome c Reductase II. Purification and Properties, *J Biol Chem* 199, 585, 1952; Stowell et al., Anal. Biochem. 15:58-64, 2016; Einhorn et al., EPMA J. 6:23. 2015. Other homogenous assays that may be implemented with the system and method embodiments described herein include:

1. Fluorescence Polarization Immunoassay (FPIA) Maragas, Toxins, 2009 1:196-207;
2. Enzyme Multiplied Immunoassay (EMIT), Zherdev et al., Analytica Chimica Acta, 1997 347:131-138;
3. Dynamic Light Scattering. Nanoparticles conjugated with a capture molecule will bind to analyte contained in the sample creating a particle-biomolecular complex. These complexes can be detected using dynamic light scattering. See U.S. Pat. Nos. 8,883,094 and 9,005,994 and Liu et al. J. Am. Chem. Soc. 2008, 130, 2780-2782; for examples of detecting analytes using dynamic light scattering and metal particles;
4. Homogenous Temperature and Substrate Resolved Chemiluminescence Multi-analyte Immunoassay, See Kang et al., Analyst, 2009, 134:2246-2252; and
5. AlphaLISA assay (Perkin-Elmer, Waltham, MA). Ullman, E. F. et al. Luminescent oxygen channeling assay (LOCI): sensitive, broadly applicable homogeneous immunoassay method. Clin. Chem. 42, 1518-1526 (1996). McGiven, J. A. et al. A new homogeneous assay for high throughput serological diagnosis of brucellosis in ruminants. J. Immunol. Methods. 337, 7-15 (2008). This assay uses two different beads (alpha donor bead and AlphaLISA acceptor bead) that when both are bound to analyte, the acceptor bead can emit light at a certain wavelength upon excitation.

Assays according to the invention can be used on a purely qualitative basis particularly when detecting the presence of mesothelin, and optionally, another analyte, or alternatively, detecting the presence of mesothelin in view of a subject symptomatic for hydrosalpinx. Indications of or symptoms of of hydrosalpinx include infertility, pelvic pain, vaginal discharge, or existence of or history of pelvic inflammatory disease (PID) in some embodiments. However, in many embodiments, assays according to the invention can be used with a measure of the intensity of the signal indicating binding to produce a quantitative or semi-quantitative result. These assays may provide a level of analyte in the sample, which may be compared to a threshold level of one or more analytes in the sample in order to detect hydrosalpinx in the subject.

For example, hand-held point-or-care analytical devices can provide a quantitative result by using unique wavelengths of light for illumination and either complementary-symmetry metal-oxide-semiconductor (CMOS; complementary metal-oxide-semiconductor) or charge couple device (CCD) detection technology to produce a readable image of the result. Using image processing algorithms specifically designed for a particular test type and medium, intensity is correlated with analyte concentrations. Other non-optical techniques for reporting quantitative results in the lateral flow test form include magnetic immunoassay (MIA). Liquid phase binding assays are performed in solution. Solid phase specific binding assays provide very sensitive detection of analytes in fluid samples. These assays incorporate a solid support to which a capture molecule (such as an antibody, antibody substitute, antigen, hapten, receptor, analyte, receptor, ligand, and the like, or any member of a specific binding pair) is attached. The support can be any convenient substrate, including but not limited to the inside surface of a reaction vessel, a plate, tube, well, dipstick, microfluidic conduit, particles or beads made of a material such as polystyrene, nylon, nitrocellulose, cellulose acetate, glass fibers, poly-vinylidene fluoride), gold, magnetic material, polysaccharide (e.g., agarose), and the like. The reaction site or substrate on which the capture molecules are immobilized also is chosen to provide characteristics for detection of light absorbance. For example, the reaction site may be functionalized glass, Si, Ge, GaAs, GaP, $SiO_2$, $SiN_4$, modified silicon, or any one of a wide variety of gels or polymers such as (poly)tetrafluoroethylene, (poly) vinylidenedifluoride, polystyrene, polycarbonate, polypropylene, or combinations thereof. In general, any suitable or appropriate material(s) can be used in accordance with the present invention.

Methods for immobilizing the capture molecule on these substrates depend on the identity of the substance to be immobilized and the surface. These methods are well known in the art and can be chosen and/or modified according to need by any person of skill in the art.

Detection of the binding of capture molecule to target analyte can be achieved by any of a large number of known methods. Any of these methods are contemplated for use with embodiments of the invention. Examples of labeling and detection methods include, but are not limited to, radioactive isotope, enzyme-substrate, colorimetric and visual, fluorescence, chemiluminescence, magnetic, molecular beacons, and the like.

In certain embodiments, the assay platform is configured for multiplex detection of more than one analyte. Such assays employ two or more capture molecules, each of which specifically binds an analyte, and two or more detection methods so that the binding of each analyte can be determined. In preferred assays of this type, the target analytes include an angiogenic ocular analyte and an inflammatory ocular analyte. The dual detection can be performed in a single container where all the reagents for both assays are mixed together, or in two separate containers or vessels.

In one embodiment, homogenous temperature and substrate resolved chemiluminescence multi-analyte immunoassay format can be implemented to detect one or more analytes in a sample. See Kang et al., Analyst, 2009, 134:2246-2252 for explanation of this assay format.

Traditional competitive (homogenous) assays involve a competition reaction in which the target analyte in the sample competes for binding to a specific binding capture molecule (such as an antibody or aptamer, for example) with a labeled analyte reagent. After binding, the amount of the labeled, unbound analyte is measured. The more analyte present in the sample, the less labelled analyte reagent is able to bind to the capture molecule, therefore the amount of labeled, unbound analyte is inversely proportional to the amount of analyte in the sample. In a competitive (heterogenous) assay, unlabeled target analyte from the sample competes for binding to the capture molecule with a labeled analyte reagent as described above, however the labeled unbound analyte reagent is separated or washed away and the remaining labeled bound analyte is measured. Any of these types of assays, or variations thereof as known in the art, are contemplated for use with embodiments of the invention.

Commonly, the capture molecule is immobilized on a membrane, a reaction vessel surface or on suspended beads such as agarose beads, and detection is achieved using a labeled secondary binding molecule, such as an antibody or aptamer, that specifically binds to the primary capture molecule or to another binding region on the target analyte. If the capture molecule is immobilized on beads, separation and detection can be achieved using flow cytometry, magnetic separation, and the like. In addition, binding of the capture molecule and target analyte can be detected in solution without immobilization on a substrate.

In a typical non-competitive assay, the target analyte binds to a specific capture molecule that is labeled. After separating the unbound labeled capture reagent, the bound material is measured. The intensity of the signal is directly proportional to the amount of unknown analyte in the original sample. Alternatively, the assay is performed in a "sandwich" format where the target analyte binds to the capture molecule (which usually is bound to a surface for ease of separation) and labeled secondary capture molecule also binds to the target analyte. The amount of labeled capture molecule on the surface is then measured. The label intensity is directly proportional to the concentration of the analyte because labelled antibody will not bind forming a "sandwich" if the analyte is not present in the unknown sample.

Sandwich format binding ligand affinity assays can be performed with different detection methods. Typically, these assays are performed as solid-phase assays, where the target analyte is "sandwiched" between an immobilized capture molecule and a labeled capture molecule, each capture molecule binding to a different, non-overlapping epitope or binding area of the analyte. Immobilization allows the user to remove unbound substances from the bound analyte prior to detection with the labeled capture molecule. The primary capture molecule can be immobilized on any surface, for example the surface of the testing vessel (e.g., a multiwell plate), beads, a dipstick, filters, or column resins. The capture molecules (primary and secondary (labelled)) can be selected individually from antibodies, antibody substitutes, receptors, aptamers, nucleic acids, or any specific binding molecule. Most commonly these assays use an enzyme detection system, but any detection system can be used. Further labels and detection systems are discussed below.

An exemplary sandwich-type assay can be performed using a biotinylated aptamer or antibody capture molecule, immobilized on a streptavidin plate or beads. Sample containing the target analyte is incubated in a buffered solution with the immobilized capture molecule and then is washed away, leaving bound target analyte. A secondary capture molecule, such as an antibody or antibody substitute, then is incubated in a buffered solution with the bound target. The sandwich complexes are detected directly, by detecting the label on the secondary capture molecule, or indirectly using a labeled antibody that binds to the secondary capture molecule. These assays are known in the art and can be modified as necessary by a person of skill, including determining optimum concentrations of the reagents, and the like.

Competitive assays can be designed on a number of platforms and using various detection methods, however a two-step assay is preferable when greater sensitivity is required or the available sample size is small. In a typical two-step assay, sample containing the target analyte is exposed to immobilized capture molecules that bind the analyte. The immobilized analyte, bound to the capture molecules, then is exposed to a solution containing conjugated (labeled) analyte at a high concentration. This conjugated analyte saturates any of the immobilized capture molecules which are not bound to target analyte from the sample. Before equilibrium is reached and the previously bound target analyte can be displaced, the conjugate solution is removed. The amount of label bound to the immobilized capture molecules is inversely proportional to the amount of analyte present in the sample.

"Pull-down assay" refers to an assay which comprises removal of a target from solution. This removal occurs when a capture molecule in solution or suspension is mixed with the sample containing the target analyte and specifically binds to it. The capture molecule is labeled or bound to a substrate which allows the bound material to precipitate, agglutinate or otherwise be physically separated, for example using simple gravity, a magnet, centrifugation, and the like. In an agglutination assay, capture molecules that are bi- or multimeric- (i.e., that possess two or more specific binding areas, like an antibody) or substrates bearing multiple capture molecules, bind to the target analyte, forming large complexes that clump, precipitate, or agglutinate in the solution and fall to the bottom of the testing vessel. These large complexes can be seen with the naked eye if large enough and contain a visible color, for example, or can be seen with the aid of a microscope. In some embodiments, the clumps also contain a label that can be detected by other means, or the clumped material can be analyzed by chromatographic means. Latex agglutination involves latex particles, preferably colored particles, which are coated with bound capture molecules, which form complexes in the presence of the target analyte. Pull-down assays are convenient methods to determine whether a physical interaction between the target analyte and the capture molecule has taken place, i.e., to determine the presence of the analyte or as a semi-quantitative assay to determine relative amounts of the analyte.

Lateral flow tests also known as lateral flow immunochromatographic assays, are simple devices intended to detect the presence (or absence) of a target analyte in sample (matrix) without the need for specialized and costly equipment. Typically, these tests are used for medical diagnostics either for home testing, point of care testing, or laboratory use. These tests are based on a series of capillary beds through and across which the sample fluid migrates from a sample area or sample pad, across defined areas that contain various reagents. A typical assay uses a conjugate pad, in which the conjugated capture molecule which binds specifically to the target analyte is located. Upon binding, the captured analyte continues to flow laterally to a second area where a secondary capture molecule binds and immobilizes the conjugate-analyte complex in a relatively small area. Once the complexes accumulate, the conjugate's label, usually a colored particle, becomes more concentrated and hence detectable, often by the accumulation of color. Lateral flow tests of this type can operate as either competitive or sandwich assays.

General background information regarding lateral flow immunoassay systems is provided in Lateral Flow Immunoassay, Raphael C. Wong and Harley Y. Tse (Editors), 2009, Humana Press, a part of Springer Science+Business Media, LLC. (Library of Congress Control Number 2008939893) and U.S. Pat. No. 8,011,228. A specific embodiment of a lateral flow test is as follows.

Targets

A certain threshold level of analyte preferably is detected in a sample in order to provide beneficial information regarding the subject. Persons of skill are able to determine the optimal concentrations of the capture molecule, conjugate (labeled) molecule, and other reagents and assay components tor optimal sensitivity and accuracy.

Preferred targets are proteins or peptides. The most preferred target analytes include, but are not limited to, mesothelin, Galectin-3-binding protein, Clusterin, Polymeric immunoglobulin receptor, Neutrophil gelatinase-associated lipocalin, Leucine-rich alpha-2-glycoprotein, Osteopontin, Alpha-amylase 1, WAP four-disulfide core domain protein 2, Mucin-16, CD55, CD59, GSTP1, PRDX5, TXN, PRDX6 and SOD1. Mesothelin is the most preferred target analyte. Other preferred targets are found in Table 3. In addition, explanation and scientific relevance of various targets are provided in the Examples below.

EXAMPLES

Example 1: Methods and Materials

Experimental Procedures

Reagents

The majority of chemicals used herein were obtained from Thermo scientific (Rockford, IL), Cell signaling Technology (Danvers, MA) and Invitrogen (Carlsbad, California) and used without further purification unless otherwise stated. Antibodies to MSLN, CD59, SOD1, GSTP1 (Cell Signaling Technology, Danvers, MA) PRDX pathway cocktail and TF (abcam, Cambridge, MA) were purchased from the indicated vendors.

Patient Selection

Ethical approval for this study was obtained from the Institutional Review Board at Madigan Army Medical Center (No. 212093). All women were aged 18-45 years and provided written and informed consent for study inclusion before sample collection. Fallopian tube aspirates (from women with hydrosalpinx) or lavages (from women undergoing tubeal re-anastomosis) and sera (for measurement of circulating estradiol and progesterone concentrations for endocrine staging and for validation analysis) were collected from women with regular menstrual cycles (24-34 days) who had no previous history of ectopic pregnancy and had not taken any hormonal preparations in the three months prior to surgery (n=26; mean age 31 years; see Table 2).

Women in the control group (n=16; mean age 32.1±1 years) were fertile with a history of isthmic tubal interruption and desired fertility requesting microtubal anastomosis (MTA) surgery. Prior to laparotomy for MTA, a laparoscopic survey was conducted to assess adequacy of segments for re-anastomosis at which time a normal pelvis (no endometriosis, tubal disease or leiomyomata) was visually documented. Women in the hydrosalpinx group (n=10; mean age 30.5±2 years) were identified as having a communicating hydrosalpinx by hysterosalpingogram (HSG) performed three or more months prior to surgery. At laparoscopy, hydrosalpinx was confirmed by the presence of tubal distention >3 cm diameter in the setting of distal tubal phimosis and a variable degree surrounding pelvic and/or perihepatic adhesions.

Clinical Samples.

Prior to general anesthesia, serum was collected by venipuncture for estradiol and progesterone analysis. For fallopian tube lavage specimen collection, laparoscopy, which is used to enter the abdomen, was converted to laparotomy via Pfannenstiel incision for women with adequate tubal segments to support re-anastomosis surgery. The external surface of the fallopian tube and fimbria were rinsed of any blood with warm normal saline (NS). The proximal (isthmic) end of each distal fallopian tube segment was entered with a 24-gauge needle and irrigated with 1 mL of NS. The lavage fluid was collected from the distal fimbriated end of the tube in a sterile conical tube, immediately placed on ice and taken to the lab for further processing. For hydrosalpinx specimen, the affected tube was entered at the isthmic-ampullary region of the tube using a laparoscopic aspirating needle attached to a sterile 10 cc syringe prior to salpingectomy for hydrosalpinx-associated infertility. The hydrosalpinx fluid was aspirated, transferred to a sterile collection tube, immediately placed on ice, and taken to the lab for further processing. The in vivo collection of tubal fluids precluded the potential confounding influence of ischemia on proteomic signatures.

Experimental Design and Statistical Rationale
Sample Size and Power Analysis

Figure 9:
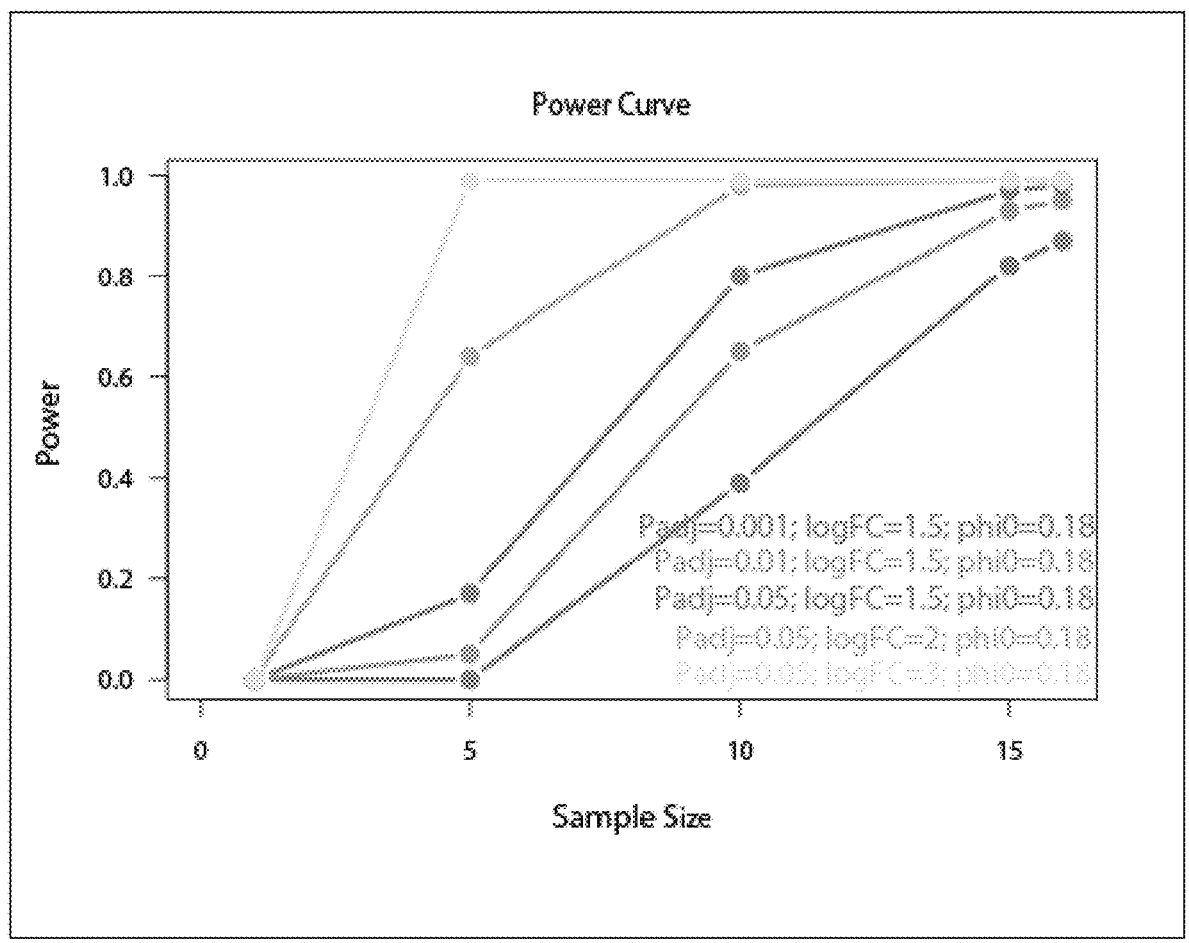
FIG. 9 is a graphical representation of a relationship between power and sample size at Padj=0.001, 0.01 or 0.05 for log FC=1.5, 2, or 3 in protein expression.

Power analysis was performed using a pilot shotgun proteomics data set and an open source RnaSeqSampleSize package (www.biocondactor.org) to estimate the number of samples providing enough power to detect minimum differences in mean protein abundance between hydrosalpinx and lavages from healthy fertile controls. The within-group median dispersion (variances) was computed using DEseq2 ((www.biocondactor.org) for spectral count data collected from a pilot shotgun proteomics experiment for hydrosalpinx fluids (n=5) and lavages from healthy fertile controls (n=7). The power curves per hypothesis of the negative binomial distribution test were generated as a function of sample size required to detect log 2 fold changes of 1.5, 2, 3, at the adjusted p-value of 0.05, 0.01, and 0.001 and shown in FIG. 9. It is clear from these curves that with the data median dispersion (dispersion=0.18 from our pilot study), significance level, and sample size have profound effect on power. As clinical sample numbers were limiting, the power curve at p-adjusted=0.05 was an appropriate choice for our study and using this curve it was estimated that biological replicates of ten per experimental group results in >=80% of chance of detecting a 1.5- and above fold change. Thus, we design this study with n=10 for hydrosalpinx and n=16 for lavages from health fertile controls.

Label-Free Shotgun LC-MS

Tubal fluids collected from women with hydrosalpinx (n=10) and healthy fertile women undergoing tubal sterilization reversal (n=16) were immediately spun down at 200 g to pellet any cellular contaminants. The supernatant was then transferred to Eppendorf tube (e.p.t) and any cell debris was removed by further centrifugation at 14,000 g for 10 minutes. The supernatant was transferred into clean e.p.t tube, spiked with cocktails of protease inhibitors (Thermo Scientific) and then stored in 50 µl aliquots at −80° C. until used for the downstream analysis.

For label free shotgun proteomics, proteome content of each tubal fluid was normalized via BCA assay (Thermo Scientific), and each sample was diluted to 5 micrograms in 20 microliters reduced and alkylated with DTT and iodacetamide respectively. Proteolytic digestion was performed with modified trypsin (Promega) for 18 hours at 37° C. A primary stock solution of pierce peptide retention time calibration mixture standard (ThermoFisher Scientific) containing heavy labeled lysine and arginine was prepared to a concentration of 1 pmole/µL each. The standard peptides mix was added to each proteolytic digestion such that their final concentration was 75 fmole/µL. Six hundred nanograms of each sample was analyzed by LC-MS and the order of sample injections were randomized to account for random error. Separation of peptides via liquid chromatography was performed using Acquity UPLC system. Mobile phase A (aqueous) contains 0.1% formic acid in water and mobile phase B (organic) contained 0.1% formic acid in 100% acetonitrile. Sample was trapped and desalted on-line in mobile phase A at 10 µL/minute for 5 minutes using a nanoAcquity UPLC trap column 5 µm, 180 µm×20 mm. The sample was subsequently loaded onto an Acquity UPLC M-class peptide BEH C18 130 Å, 1.7 µm, 75 µm×150 mm, reversed phase column with 5% mobile phase B. Separation was obtained by employing a gradient of 5% to 30% mobile B at 0.300 µL/minute over 180 minutes. The column was washed at 90% mobile phase B for 10 minutes, followed by a re-equilibration at 99% A for 15 minutes. Mass spectrometry analyses of samples were performed using LTQ Orbitrap XL mass spectrometer (Thermo Scientific). Positive mode electrospray was conducted using a nebulized nanoflow sprayer and the mass spectrometer was operated at a resolution of 60,000. Quantitative and qualitative data was acquired using alternating full MS scan and MS/MS scans. Survey data was acquired from m/z of 380 to 1800 and each full MS scan was followed by six MS/MS scans using data-dependent acquisition with the dynamic exclusion option specified as follows: repeat count, 2; repeat duration, 30 s; exclusion duration, 45 s.

Data Search Parameters.

Automated identification followed by differential quantification of proteins in sets of samples was accomplished by Proteome Discoverer version 1.4.0.288 (Thermo Fisher Scientific) and open source R-packages respectively. Within this over all workflow, first peak lists from Xcalibur raw data file were extracted using Proteome Discoverer spectrum selector algorithm once the raw data files of interest were imported into proteome discoverer. Spectrum selector node was set to its default values, therefore the data was not smoothed, no signal to noise threshold was set, and no charge state filtering or de-isotoping took place. Prior to searching the peak list files, Swiss-Prot.fasta human database 20,183 sequences was downloaded (Mar. 23, 2017) from UniPort (www.uniprot.org/) to the local server and appended with decoy sequences. The resulting peak list files were then searched against the human database by running SEQUEST search engine. SEQUEST searches performed with search parameters set to search for tryptic peptides with up to 2 missed cleavages (C-Term K/R restrict P), static modifications with carbamidomethyl (C), dynamic modifications with deamidation (N/Q), and/or oxidation (M). Precursor mass tolerance was set to 10 ppm and fragment mass tolerance to 0.5 Da.

Peptides identification were validated via running decoy database search with Percolator. Peptide-spectrum match (PSM) is considered correct if it achieved the estimated q-value (minimal false discovery rate) of 0.01 or less. For protein identification, a minimum of two peptides with delta Cn (delta correlation)<=0.05 and with high confidence based on q<=0.01 were utilized to ensure the protein level stringency. Peptide and protein grouping were enabled, peptides were grouped by both mass and sequence similarities. Protein grouping was considered only PSMs with high confidence and via applying strict maximum parsimony principle.

Quantitation and Statistical Analysis.

The relative abundance for identified proteins was measured on the basis of the spectral count (the total number of identified peptide spectra matched to the protein of interest, including those redundantly identified). The spectral counts or peptide-spectrum matches (PSMs) and associated protein identity was exported to MS-EXCEL. This MS-excel file was then processed to generate spectral count matrix. The count matrix cell in the $i^{th}$ row and the $j^{th}$ column indicates how many peptide spectra matched to protein i in sample j (which stems from an independent biological replicate). Missing count values were replaced with zero and zero counts in DEseq algorithm (21) treated as some positive value below 1. The spectral count matrix along with the metadata Table, which contains samples ID, Factors and Levels were read into R.

For differential expression analysis, the raw count data was processed using an DESeq2 which is implemented as a package for the R statistical environment (21) and available through Bioconductor repository (www.biocondactor.org). DESeq2 is an open source and one of the two widely used differential expression analysis methods for high throughput count data. The method and the workflow used to test for differential expression is described in detail by Love et al (21). Briefly, the analysis with DEseq2 started with the observed spectral count matrix where the matrix entries Xij indicate the number of spectral counts that have been unambiguously mapped to a protein i in a sample j. In case where there were multiple isoforms in the sample and they were resolved based on additional unique peptides, PSMs from the common peptides were shared among the isoforms. DESeq2 analysis is based on the assumption that Xij are observation from the negative binomial distribution with expected mean pij and dispersion αij, the expected spectral count matrix is expressed as generalized linear model (GLM) of binomial family with log link (22). Based on prior studies demonstrating sex steroid regulation of protein expression in the Fallopian tube (23, 24), we sought to control for menstrual cycle phase in comparing the proteomic signatures from hydrosalpinx-affected and normal tubes. Experimental samples from each group were matched for menstrual cycle phase (Table 2), and cycle phase was added to the model formulae as a second factor affecting protein expression. The raw spectral count data (spectral count Table) and the metadata Table were used to generate a DESeqDataSet object using DESeqDataSetFromMatrix. The DEseq function was run using DESeqDataSet object which sequentially performs estimateSizeFactors, estimateDispersions, and nbinomWald Test analysis that are wrapped into a single DEseq function. Proteome result Table including log 2 fold changes, P-values, and adjusted P values were extracted using results function. Differential expressed proteins were then filtered with Benjamini Hochberg adjusted p<=0.05 and summarized in Table 3.

High Dimensional Data Visualization

To assess overall similarity or differences between samples within and among the experimental groups and to identify any outlier data, we computed the Euclidean distance between samples using the R function dist on normalized and regularized log (rlog) transformed spectral count data. Sample-to-sample distances were then visualized via hierarchical clustering and Heatmap and/or PCA analysis using heatmap and/or plotPCA R-function.

Western Blotting Analysis

Tubal fluid collected from women with hydrosalpinx (n=6) and tubal lavages from cycle phase matched healthy fertile women (n=5) were processed for immunoblot analysis using an established protocol. Briefly, twenty micrograms of tubal fluid proteome from each sample resolved on 4-12% polyacrylamide gels (Invitrogen) and transferred onto nitrocellulose membrane. The membrane was blocked with 5% skim milk, washed, and incubated overnight with specific primary antibody against MSLN (0.59 ng/µl), CD59 (8 pg/µl) SOD1 (1.11 ng/l), GSTP1 (0.04 ng/µl), PRX pathway (cocktail of TXN, PRX1, and TXNRD1, at 0.38×/µl), or TF (0.70 ng/µl). The membrane was washed and incubated with horseradish peroxidase (HRP)-conjugated secondary antibody (2 ng/µl). Once the blot was incubated in chemiluminescent substrate, signals were captured using Kodak imaging system. The bands on the image were processed and quantified using an open source image processing tool ImageJ 1.48V (http://imagej.nih.gov/ij) software. Each blot was re-probed for transferrin for the purpose of signal normalization (loading control).

Immunohistochemistry

Immunohistochemical analysis of fallopian tissue sections from both hydrosalpinx and healthy control was conducted using an established protocol. Briefly, 4 µm tissue sections from formalin-fixed paraffin-embedded tissues were prepared and deparaffinized. The antigenic epitopes were unmasked using the antigen retrieval method. Then, the sections were soaked in peroxidase and alkaline phosphatase blocking reagent (Dako North America Inc.,) for 30 min at room temperature to inactivate the endogenous peroxidase activity. The sections were then blocked with 2.5% horse serum for 30 minutes, and incubated overnight at 4° C. with anti-MSLN at 52 pg/µl. Sections were then incubated with a peroxidase-conjugated anti-rabbit and visualized with DAB (Impact DAB kit, Vector). Cell nuclei were counterstained with hematoxylin for 5 seconds, and then rinsed in water. For CD45, however, staining in 4 µm paraffin-embedded tissue section was performed using automated system (Ventana Discovery).

Enzyme-Linked Immunosorbent Assay (ELISA)

Figure 13:
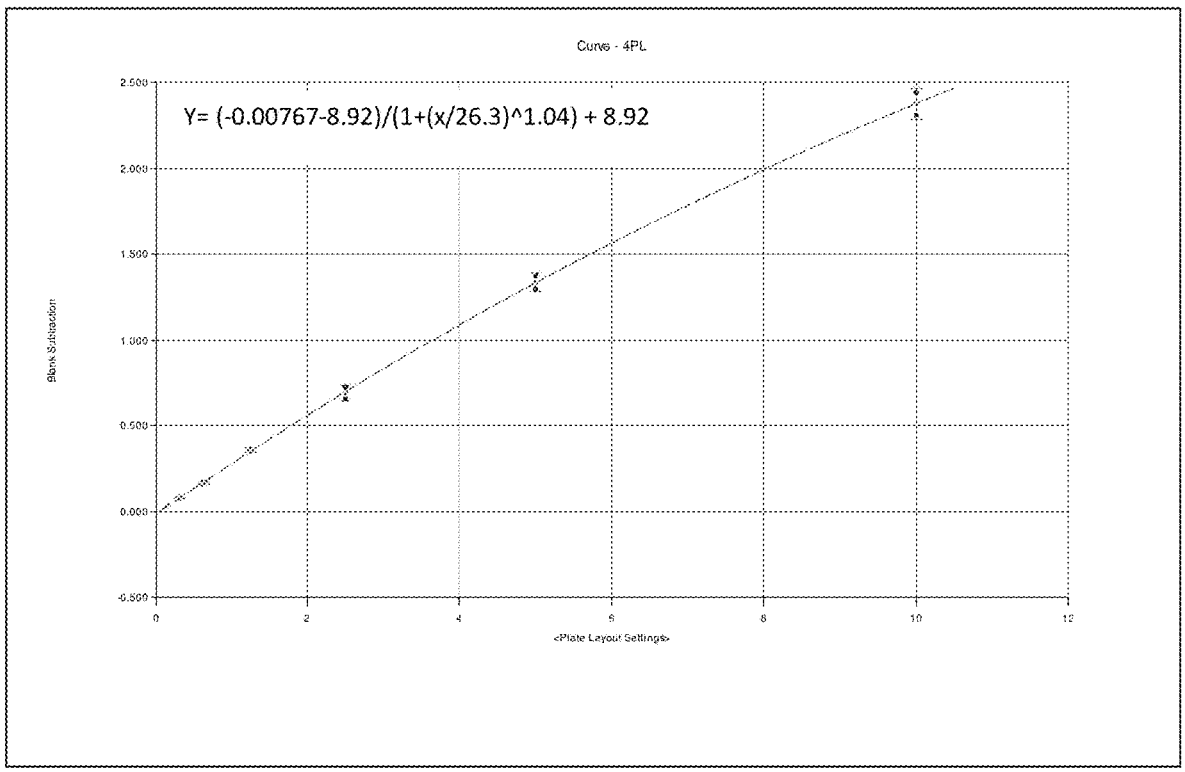
FIG. 13 is a graphical representation of a standard curve for human mesothelin.

Plasma collected from women with hydrosalpinx (n=9) and healthy fertile women (n=9) were processed for ELISA using an established protocol (www.RnDSystem.com). Briefly, human mesothelin standards with working concentration of 10, 5, 2.5, 1.25, 0.625, 0.313, 0.156, 0 ng/mL (each in duplicates) and 10 fold diluted plasma samples (each in triplicates) were added into 96-well plate coated with a monoclonal antibody specific for human mesothelin and incubated for 2-hours. The plate was washed and incubated with monoclonal antibody specific to mesothelin conjugated to HRP. The plate was washed, incubated with substrate for 30 min for signal to develop. The absorbance of each well was read at 450 nm and at 570 nm after the addition of stop solution. Once the absorbance readings at 570 nm and for blanks subtracted from 450 nm reading, standard curve was generated and fitted using a four-parameter logistic curve fit (FIG. 13). Linearity of the assay was assessed using serially diluted plasma containing higher concentration of Mesothelin per manufacturer recommendation (www.RnDSystems.com).

Enrichment Analysis

List of proteins with significant changes (Padj value<=0.05) and their corresponding estimated log 2 fold changes were uploaded into Ingenuity Pathway Analysis (IPA) (www.qiagenbioinformatics.com). Cellular locations and biological insights for the uploaded protein lists were performed using IPA software and manually curated databases.

Plasma Mesothelin Concentration in Women with and without Hydosalpinx

Plasma collected using heparin as anticoagulant from patients with and without hydrosalpinx were tested for mesothelin using Fujirebio Diagnostic Inc. Mesomark ELISA kit Assay protocol. However, the diluted (101-fold, per assay protocol) plasma levels of mesothelin in women with and without hydrosalpinx were below the lowest concentration of the Calibration Fit. In order to optimize the accuracy of the results, the levels of mesothelin were re-assayed at various dilutions of plasma from one of hydrosalpinx patients. FIG. 16 shows a graphical representation of plasma mesothelin concentration in women with and without hydrosalpinx. FIG. 16A shows a standard curve for soluble mesothelin related peptides: a plot of mean absorbance for each standard with standard error from the mean (SEM) on the y-axis against the concentration on the x-axis. FIG. 16B shows a linearity of the mesothelin ELISA. A plasma specimen from women with surgically confirmed hydrosalpinx was serially diluted with assay diluent to produce the expected concentrations of serum mesothelin (x-axis) with the values within the dynamic range of the assay. Data points are mean of duplicates.

From the linearity test (FIG. 16B), it is clear that there is not any variation associated with dilution. The levels of mesothelin in the 20-fold diluted sample was close to the mid-point of the calibration standard curve (FIG. 16A) and this dilution was used for the follow up analysis using all the available samples.

Figure 2:
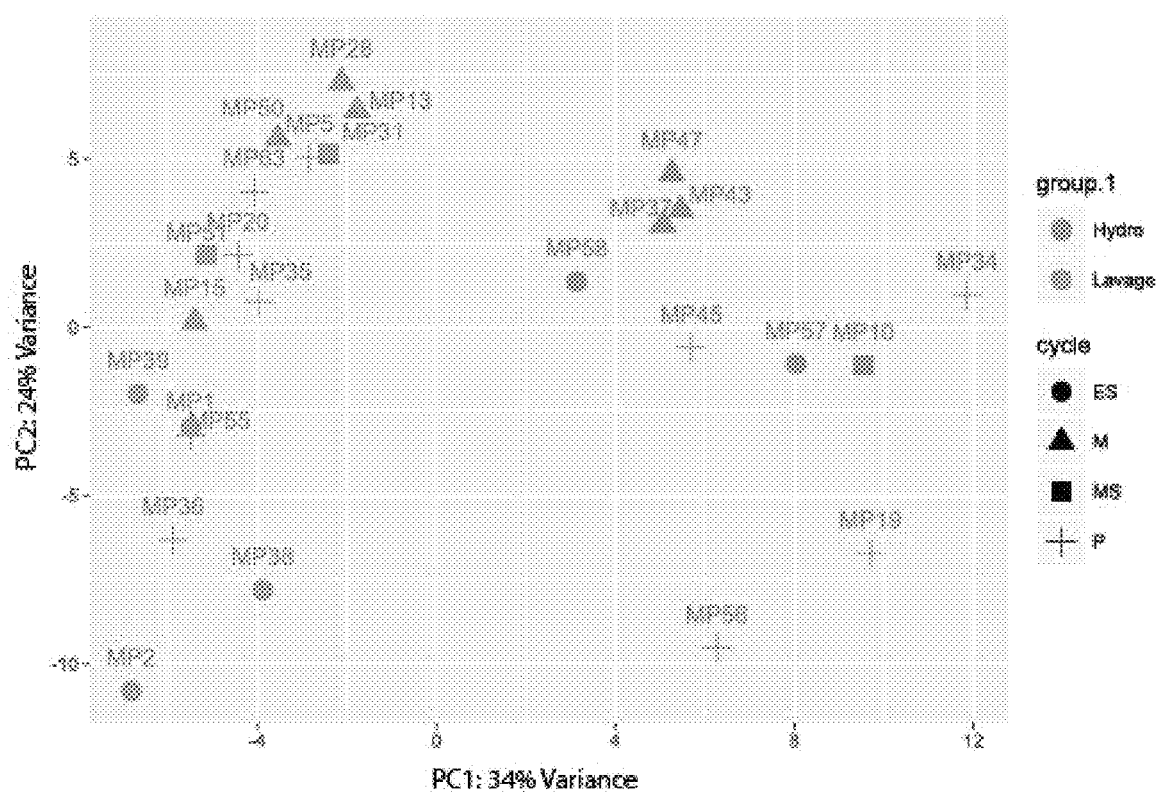
FIG. 2 provides a schematic, a principal component analysis (PCA) of secretome samples from subjects with tubal hydrosalpinx (red) and of samples from subjects of healthy fertile tubes (blue).
Figure 17:
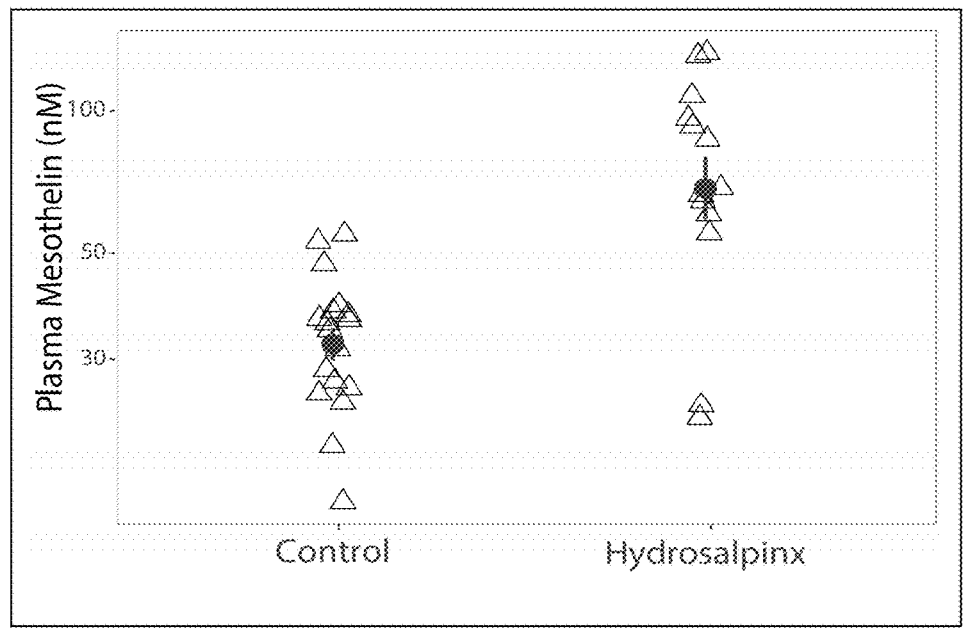
FIG. 17 provides a graphical representation of a scatter plot of plasma MSLN in control (n=18) and in women with hydrosalpinx (n=13) assayed by ELISA.

Thus, plasma collected from women with hydrosalpinx (n=13) and health controls (n=18) were 20-fold diluted and re-assayed for mesothelin. Concentration of mesothelin in the healthy control and patients with hydrosalpinx (FIG. 17) were determined from the standard curve that was generated and fitted using a four-parameter logistic regression model. FIG. 17 provides a graphical representation of a scatter plot of plasma MSLN in control (n=18) and in women with hydrosalpinx (n=13) assayed by ELISA. Mean and SEM for each group are represented with blue circle and error bar respectively. The mean plasma concentration of mesothelin in women with hydrosalpinx (77.515±9.58 nM) was significantly (p=0.00002) higher vs healthy controls (33.86±2.50 nM) (FIG. 2). This result consistent with the results obtained with R and D System ELISA Assay kit showing significantly higher mesothelin level in the plasma of patients with hydrosalpinx. Plus, similar to what was reported in the cancer patient, about 25% of women with surgically confirmed hydrosalpinx and higher concentrations of MSLN in tubal lavages exhibited lower levels in their plasma.

ROC Analysis

Figure 18:
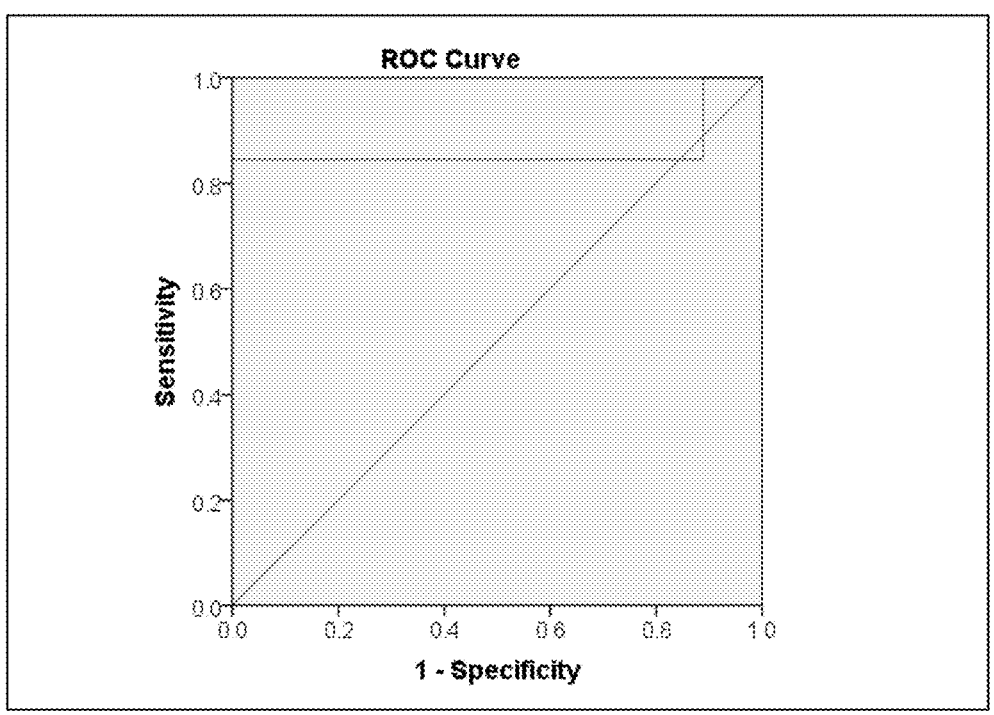
FIG. 18 is a graphical representation of an operating characteristic (ROC) curve showing the relationship between sensitivity and (true positive) and 1-specificity (true negative) in determining the predictive value of mesothelin in patients with hydrosalpinx.

From the shotgun proteomics and validation ELISA analyses we have confirmed elevated levels of mesothelin in patients with hydrosalpinx. Based on this finding, we believe that higher and lower values for mesothelin in the plasma is a predictor of a positive and a negative test for hydrosalpinx respectively. In order to know what these relationship looks like we run Receiver operating characteristic (ROC) analysis on the second ELISA data set using SPSS. Looking at the ROC curve (blue line), FIG. 18, mesothelin ELISA test could be a good diagnostic test. It is also apparent from the area under the curve (0.863, P=0.001), and 95% Confidence interval (0.687, 1.000) that a test has favorable sensitivity and specificity characteristics. Out of all the possible cutoff values on the ROC we have identified 54.945 nM as a cutoff value which has 84.6% sensitivity and 0.00% 1-specificity (0% false positive result). FIG. 18 provides a graphical representation showing receiver operating characteristic (ROC) curve demonstrating the relationship between sensitivity and (true positive) and 1-specificity (true negative) in determining the predictive value of mesothelin in patients with hydrosalpinx.

Label free LC-MS/MS analysis provided coverage with over 5,000 peptides which mapped to 519 non-redundant proteins in the two experimental groups combined. The distribution of these 519 proteins with respect to cellular location is provided in FIG. 1. As can be seen, FIG. 1 provides a pie chart showing cellular localization for non-redundant proteins identified with shotgun label free proteomics analysis.

As expected with samples obtained from a fluidic microenvironment, the majority (47%) of the identified proteins were extracellular. However, cytosolic, nuclear and proteins with unknown localization were also represented, comprising 39, 10 and 4% of the total proteins identified, respectively.

Example 2: Principal Component Analysis

Figure 10:
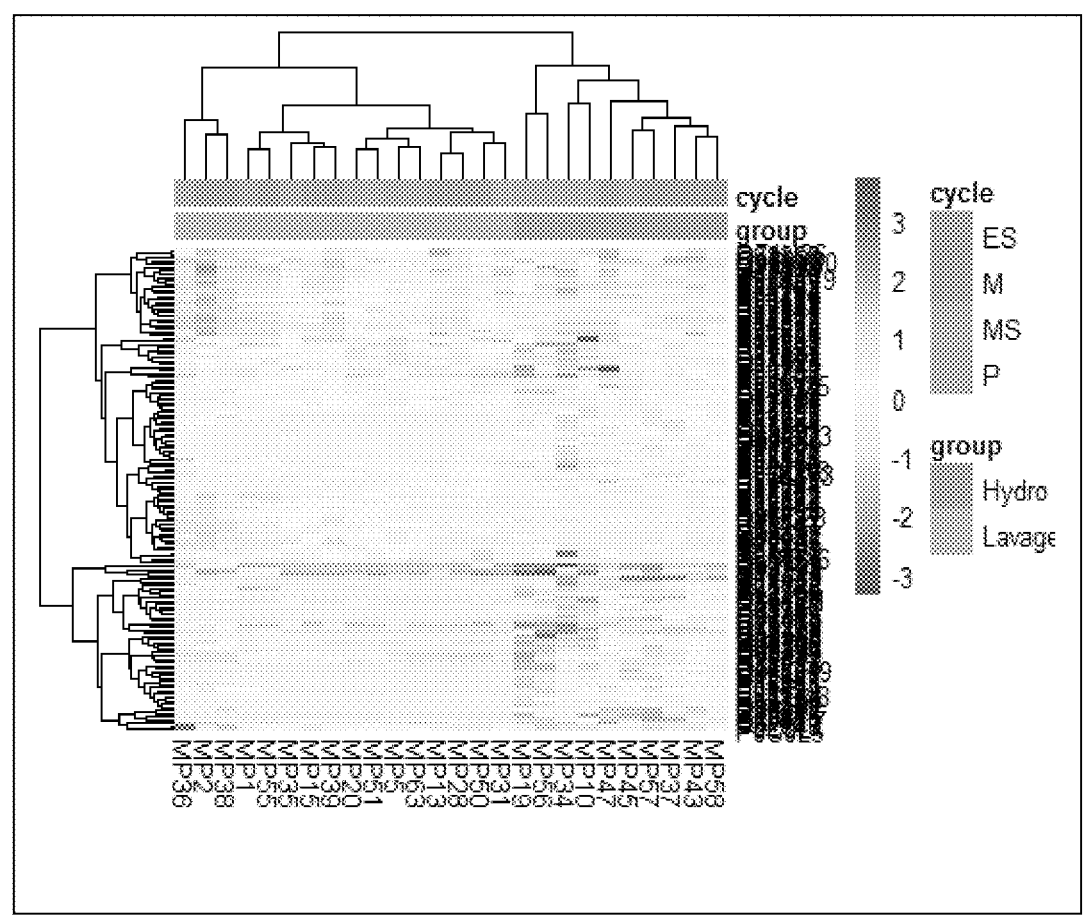
FIG. 10 is a schematic showing Hierarchical clustering and heatmap of proteins. In this heatmap proteins and/or samples are grouped together based on protein expression pattern. It is clearly in this figure that samples clustering aligns with experimental factor (hyrosalpinx/lavages).

Global relationships among samples were visualized by performing a principal component analysis on rlog transformed spectral count data and shown in FIG. 2. Before dimensional reduction, each sample existed in multidimensional space (one dimension for counts for a given protein). The sample comparisons were plotted in two-dimensional space, corresponding to the first and second principal components of variation. The first principal component for each protein is the weighted linear combination of rlog transformed spectral count values that shows maximum variation, whereas the second principal component is a weighted linear combination orthogonal to the first component that has maximum variance. For the 519 proteins, the first principal component distinguished 34% of the variance with 24% additional variation distinguished by the second principal component. Samples clustered principally by disease status of the fluid proteome (hydrosalpinx or normal) with striking absence of overlap. In this way, PCA analysis revealed that differences among the experimental groups are much more considerable than that within group differences. Clusters corresponding to the experimental groups also emerge from the hierarchical clustering (FIG. 10). In this case, it is clear that the expression vectors (the columns of the heatmap) for samples within the same cluster are much more similar than expression vectors for samples from different clusters.

Example 3: Differentially Expressed Proteins

Figure 11:
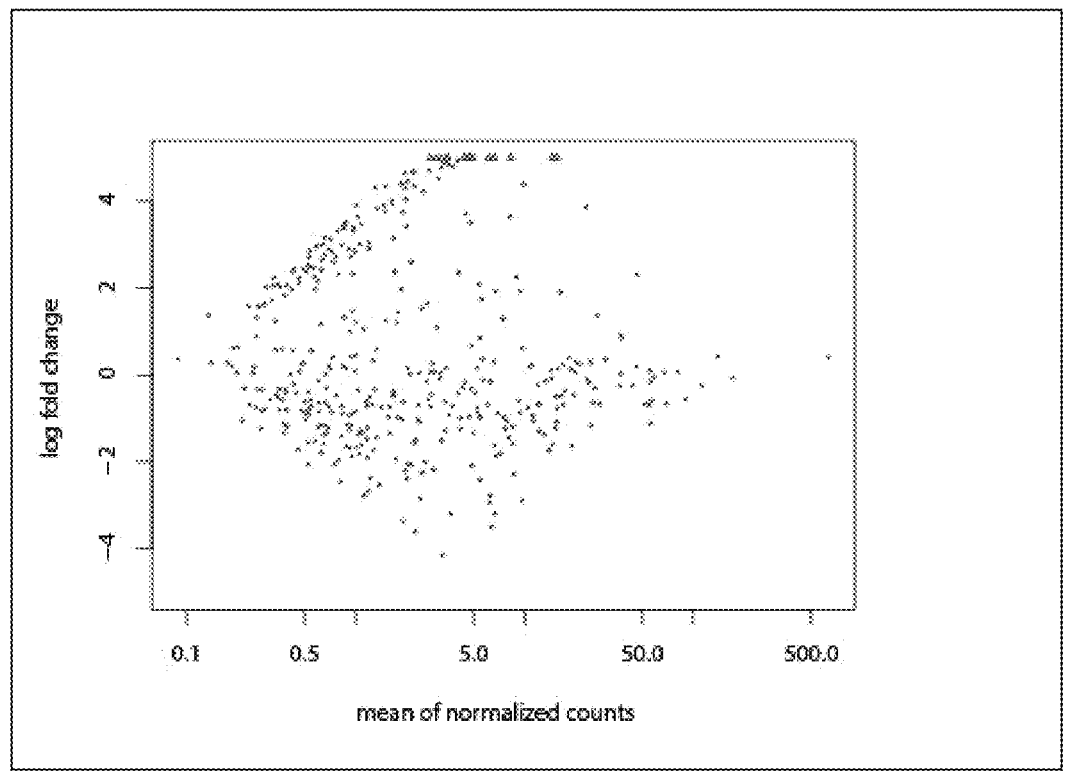
FIG. 11 is a plot showing log2fold change against mean normalized counts for the contrast hydrosalpinx versus lavage.
Figure 12:
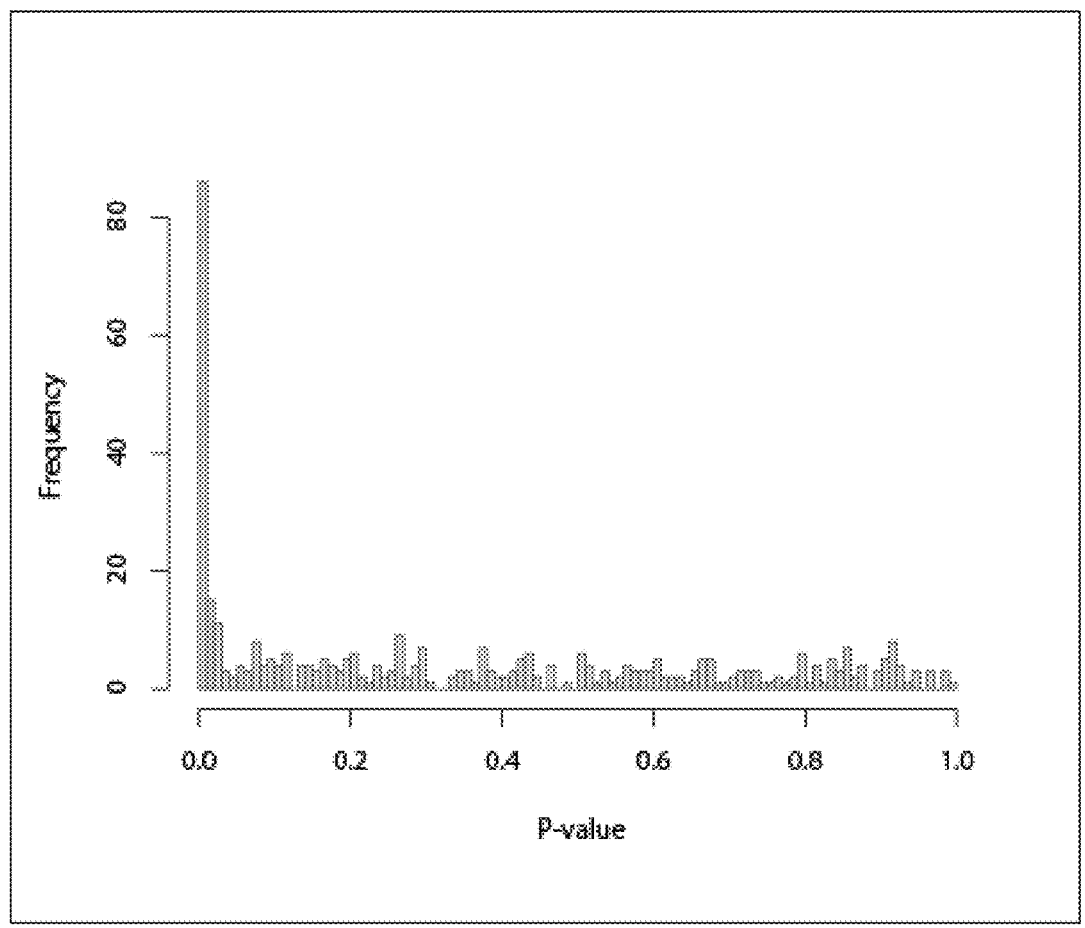
FIG. 12 is a graphical representation including a histogram of p-value from the call to binomial test. It is clear to see from this histogram that these are well behaved p-values.

The overall protein quantification for the contrast hydrosalpinx verses lavages from healthy controls were visualized in log 2 fold changes against the mean normalized counts plot (FIG. 11). Proteins that are significant at 0.1 Padj colored in red. In addition, from the P-values histogram shown in FIG. 12 it is evident that there are a set of well-behaved p-values. Flat distribution along the bottom represents null-p-values, which are uniformly distributed between 0 and 1. In this histogram it is also clear that the enrichment of low p-value close zero steams mainly from the differentially expressed proteins in hydrosalpinx relative to healthy lavages along with some null hypotheses that appear at low p-values. Once well-behaved p-value distribution was evident from p-values histogram, p-values were adjusted to control for false discovery rate. The majority of the proteins with 1.5 and above or −1.5 and below (per power analysis) and exhibiting statistical significant at Padj<=0.05 were considered significant. Thus, 116 proteins passed these criteria were filtered as differential abundant in hydrosalpinx fluids relative to tubal lavages from healthy controls and summarized in Table 3. Among these 116 proteins, 76 were up regulated and 40 were down regulated in hydrosalpinx relative to lavages from healthy controls.

Example 4: IPA Core Analysis

Figure 3:
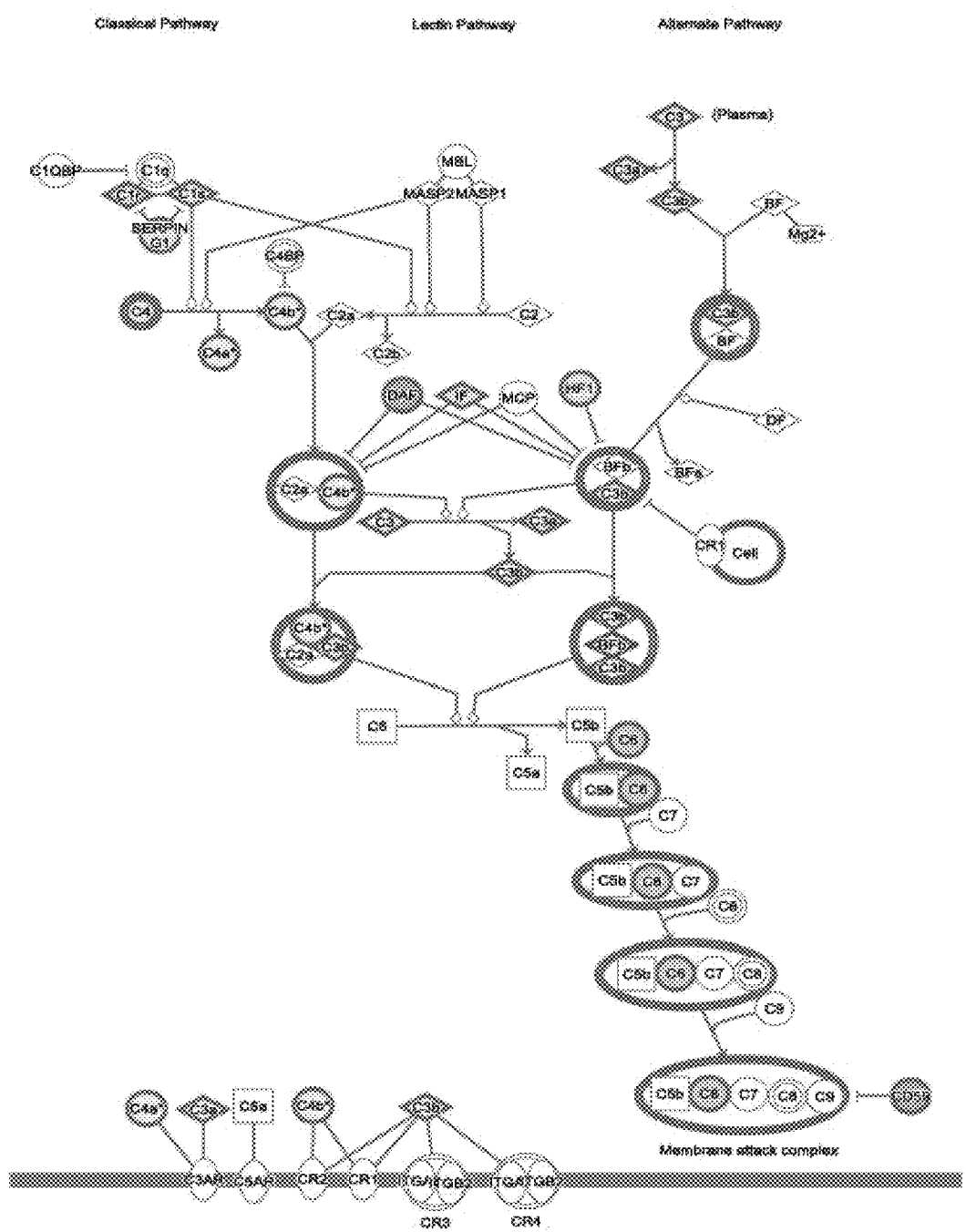
FIG. 3 shows a graphical representation of the complement system and the proteins mediated by hydrosalpinx.
Figure 4:
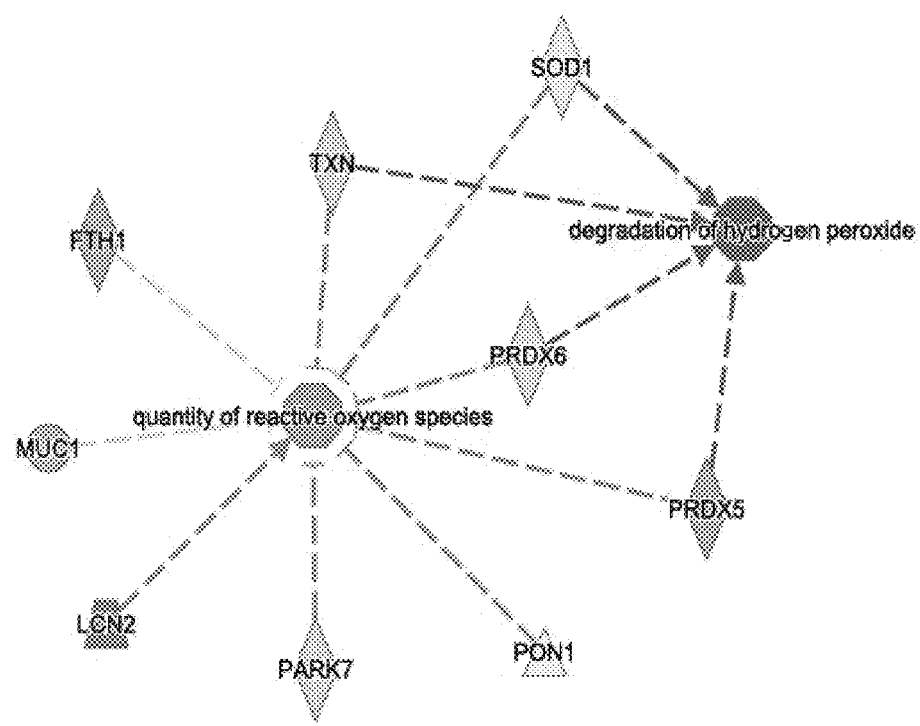
FIG. 4 is a schematic providing networks of proteins involved in the activation of reactive oxygen species (ROS) and inhibition of hydrogen peroxide degradation.
Figure 5:
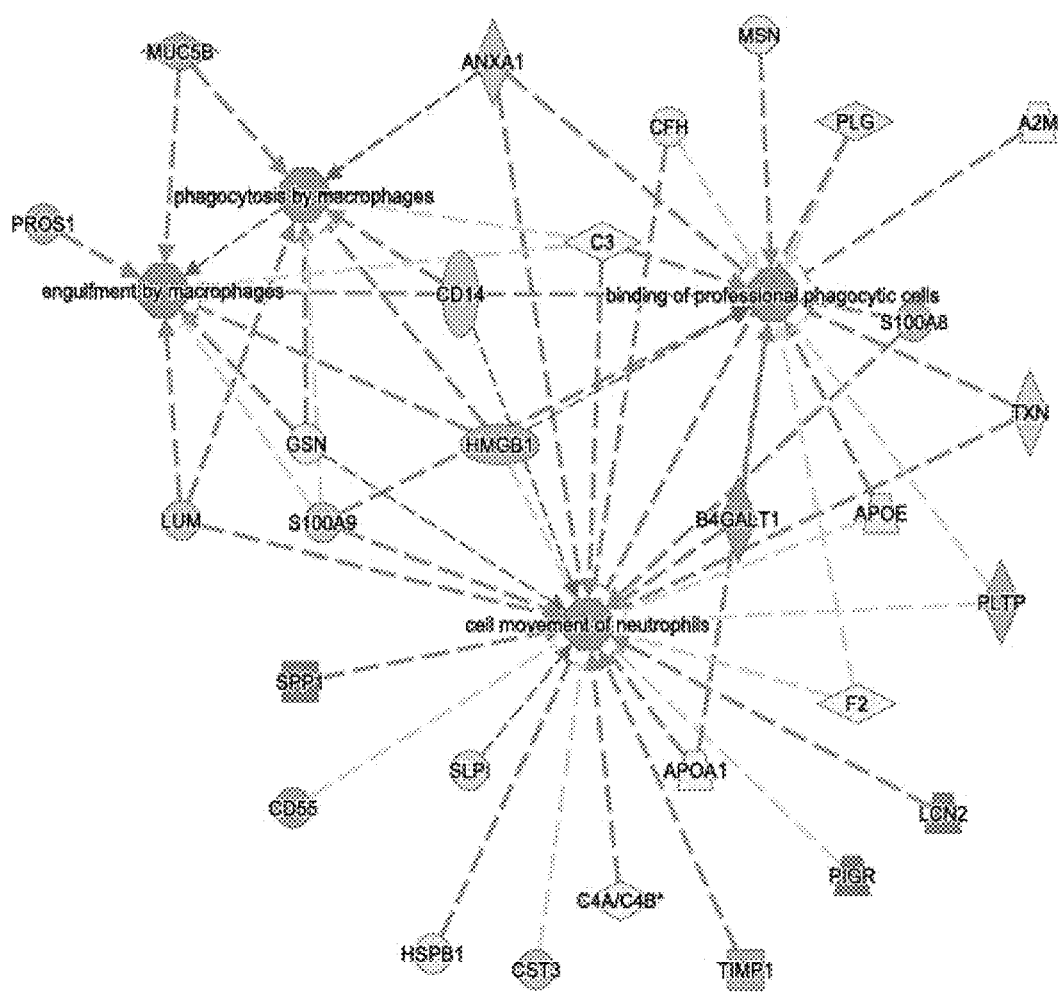
FIG. 5 is a schematic of networks of proteins involved in the immune cell infiltration and activation of phagocytosis.

To identify relationship of the differentially expressed proteins, and their enrichment in pre-defined pathways, the list of differential abundant proteome were analyzed using IPA core analysis a web-based entry tool developed by Ingenuity System, Inc. (www.qiagenbioinformatics.com). The core analysis algorithms are based on a master network which derived from Ingenuity Knowledge Based (www.qiagenbioinformatics.com). The significant results from this analysis were summarized in the pre-defined pathway (FIG. 3) and in the form of networks (FIGS. 4, and 5). FIG. 3 shows a pre-existing pathway demonstrating significant enrichment of proteins that are mediated by hydrosalpinx. In these networks, nodes with red and green highlights around the three biological processes (in the middle) are proteins identified in the current study. The red and the green colors represent the direction of change in protein expression, with red indicating up-regulation and green indicating down-regulation in the hydrosalpinx fluid relative to tubal fluid from fertile controls. The edges on the network represent predicted relationships and directional changes between the proteins and the biological processes. The blue and orange edges represent for inhibition and activation respectively, the black edges are for effects that are not predicted and yellow edge inconsistent with the state of downstream biological process. The edges with pointed arrowhead represent activating relationship and edges with blunt arrowheads represent inhibitory relationships.

Enrichment analysis revealed up-regulation of more than 25% of proteins involved the complement pathway in hydrosalpinx fluid, suggesting significant activation of the complement system in the pathophysiology of this tubal disorder (FIG. 3). Additionally, an increase in reactive oxygen species (Z-score 2.44; p=6.79E-06) and decrease in hydrogen peroxide metabolism (Z-score−2.16; P=7.96E-08) was observed (FIG. 4). FIG. 4 provides a schematic showing networks of proteins involved in the activation of reactive oxygen species (ROS) and inhibition of hydrogen peroxide degradation. Proteins are represented by different shapes of nodes that are highlighted with red (up) and green (down) regulated in hydrosalpinx. Bioprocesses in the center are represented by octagons that are highlighted with orange (activated) and blue (deactivated) in hydrosalpinx.

FIG. 5 shows a network of proteins involved in the immune cell infiltration and activation of phagocytosis. Red and green nodes represent up and down regulated proteins respectively in hydrosalpinx. In this network, up regulation of the activators and down regulation of inhibitor proteins predict the activation of the biological processes represented by orange octagons Proteins directly related to the activation of immune-cell infiltration to the site of inflammation and phagocytosis by macrophages were up-regulated in hydrosalpinx fluid. Conversely, proteins that involved in the inhibition of these biological processes were down-regulated (FIG. 5).

It is clear from these networks that the direction of the fold changes for the majority of proteins are consistent with the predicted downstream status of the biological processes. The increase in the generation of reactive oxygen species (ROS), but decease in the metabolism of hydrogen peroxide was consistent with the directionality of the fold changes for the proteins on this network with the exception of MUC1 and FTH1. It is also clear in this network that the predictive increase in ROS could also be attributed to the predictive decrease in metabolism of hydrogen peroxide due to dys-regulation of proteins that are responsible for ROS detoxification.

The interactions described by these networks identify significant functional modules that are coordinately dysregulated in hydrosalpinx tubal fluid relative to tubal lavage from fertile controls. IPA core analysis not only helped uncover the dysregulated protein modules and processes but also provided a framework for evaluating individual protein.

Example 5: Orthogonal Validation by Western Blot

To verify the directionality of fold change identified by shotgun spectral counting proteomic analysis, western blot for representative proteins was conducted in a subset of 11 patient samples (six hydrosalpinx, and five healthy control tubal lavages). Protein that is novel in the hydrosalpinx pathology (MSLN) and proteins which are involved in inflammatory and tissue damage pathway (CD59) and in the oxidative stress pathway (SOD1, GSTP1, PRX1, TXN and TXNRD1) were selected for immunoblot validation. The relative fold changes for these proteins were computed using ImageJ software with statistical significance computed using student's T-test (Table 1). For all 6 proteins, the directionality of significant fold change difference detected by shotgun spectral counting proteomics was confirmed.

Figure 6:
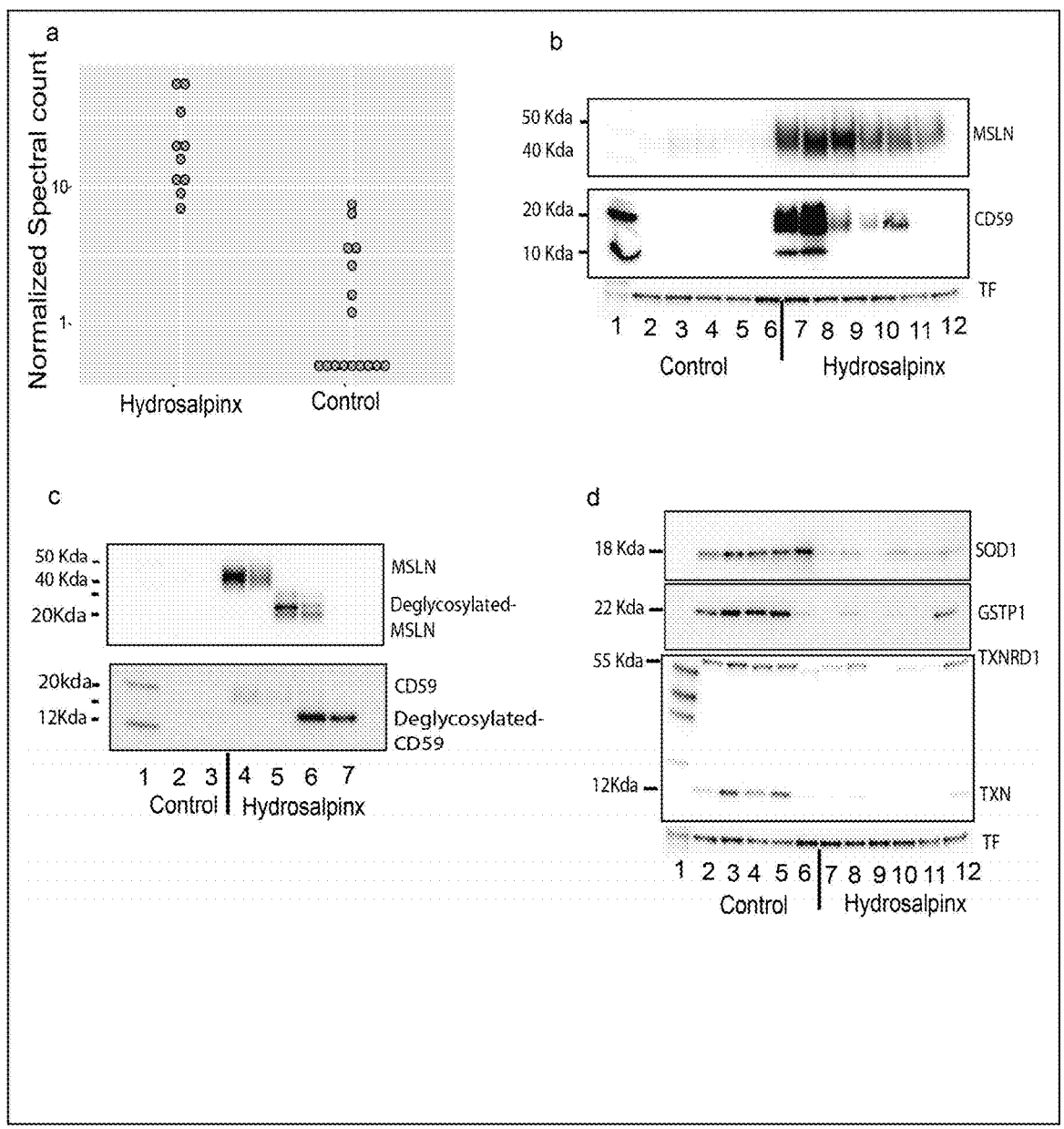
FIG. 6A is a schematic showing spectral counts for mesothelin across biological replicates in two experimental groups.
FIG. 6B shows a western blot analysis for mesothelin (MSLN), CD59 and loading control transferrin (TF) in lavages from women with and without hydrosalpinx.
FIG. 6C is an overview of before and after N-deglycosylation of MSLN and CD59 visualized by gel-shift on SDS PAGE followed by immunoblot analysis.
FIG. 6D provides results of a western blot analysis for SOD1, GSTP1, TXNRD1, TXN and TF.

FIG. 6 provides a schematic showing protein abundance for representative proteins assayed by spectral counting and orthogonal western blotting. FIG. 6A shows Spectral counts for mesothelin across biological replicates in the two experimental groups. FIG. 6B provides a verification western blot analysis (lanes 2-6 control) and (lanes 7-12 hydrosalpinx) for CD59, MSLN, and TF. FIG. 6C provides an overview of before and after N-deglycosylation of MSLN and CD59 visualized by gel-shift on SDS PAGE followed by western blot analysis (lanes 2 and 3 control) and (lanes 4-7 hydrosalpinx). FIG. 6D provides a verification western blot analysis for SOD1, GSTP1, TXNRD1, TXN and TF (lanes 2-6 control and lanes 7-12 hydrosalpinx). Mesothelin (MSLN) was among the most overabundant proteins in hydrosalpinx fluid (log 2FC=4.20; Padj=1.29E-09). Scatter plot of MSLN expression levels stratified by cohort revealed minimal overlap in expression between hydrosalpinx and fertile control specimens (FIG. 6a). Western blot analysis of MSLN levels verified significantly increased expression of MSLN in hydrosalpinx fluid (FIG. 6b and Table 1).

It is clear from the western blot (FIG. 6b) that MSLN and CD59 run as broad band which is well over and below the expected molecular weights 40 Kda, and 18 kda respectively on SDS-PAGE. Both MSLN and CD59 are glycosylphosphatidylinositol (GPI)-anchored glycoproteins (26-28) and it is possible that these samples have multiple isoforms of these proteins due to post-translational modifications. It has been shown that mesothelin has up to four potential N-linked glycosylation sites (www.uniprot.org/uniprot/Q13421) and CD59 has one (29). To see if these variances are due to N-linked glycosylation, representative samples from hydrosalpinx and control lavages were treated with PNGase F to release N-linked glycan. De-glycosylated samples were then subjected to western blot analysis using monoclonal anti-mesothelin and monoclonal anti-CD59. The result from this analysis, shown in FIG. 6c clearly highlights the glycosylated and de-glycosylated versions of MSLN and CD59 where the de-glycosylated products run faster than the glycosylated analog. De-glycosylation of CD59 results a single and sharp band right above 12 Kda indicating a complete de-glycosylation of N-linked glycosylation of CD59. However, the de-glycosylation of MSLN produced three bands that are sharp and distinct compared to a very broad band spanning between 30 Kda and 50 Kda in the original samples. These results clearly validated that the bands for both MSLN and CD59 in the original samples without de-glycosylation represent mature and various degree of N-linked glycosylated versions of the two proteins. For MSLN, however, the three sharp bands after de-glycosylation clearly suggest the presence of additional species that could arise either due to other forms of post-translational modification or due to the N-terminal cleaved product of the preproprotein in addition to the various degree of N-linked glycosylation.

The result from IPA core analysis shown in FIG. 2, in addition to displaying the predicted dysregulated biological processes, it also clearly delineated the co-dysregulation of PRX pathway which leads to a dysregulation of hydrogen peroxide metabolism (33). FIG. 2 provides the results of a principal component analysis (PCA) of secretome samples from subjects with tubal hydrosalpinx (red) and of samples from subjects of healthy fertile tubes (blue). The shapes of data points represent the menstrual cycle including: menstrual (M), proliferative (P), early secretory (ES), and mid-secretory (MS). Each plotted point represents an individual sample's expression profile distributed into a two-dimensional space based on the variance in protein expression. The labeled axes represent the two PCA components with the percentage of protein expression variation explained by each component.

To evaluate the involvement of the PRX pathways key targets in hydrosalpinx compared to control lavages were analyzed using the PRX pathway western blot cocktail (Abcam) which is designed to determine the relative abundance of TXN, TXNRD1, and PRX1 proteins that are key enzymes in the thioredoxin redox pathway. As shown in (FIG. 6d and Table 1) hydrosalpinx samples have about 11- and 4-fold less TXN and TXNRD1 respectively compared to healthy control lavages. However, western blot analysis of these samples using PRX pathway cocktail did not reveal any signal for PRX1.

In addition, verification western blot analysis for additional redox modulator proteins including GSTP1 and SOD1 in hydrosalpinx and healthy control lavages (FIG. 6d and Table 1) delineated significant suppression of both GTP1 and SOD1 in hydrosalpinx compared to healthy control lavages confirming the results of the shotgun proteomic analysis.

Example 6: Immunohistochemistry

Figure 7:
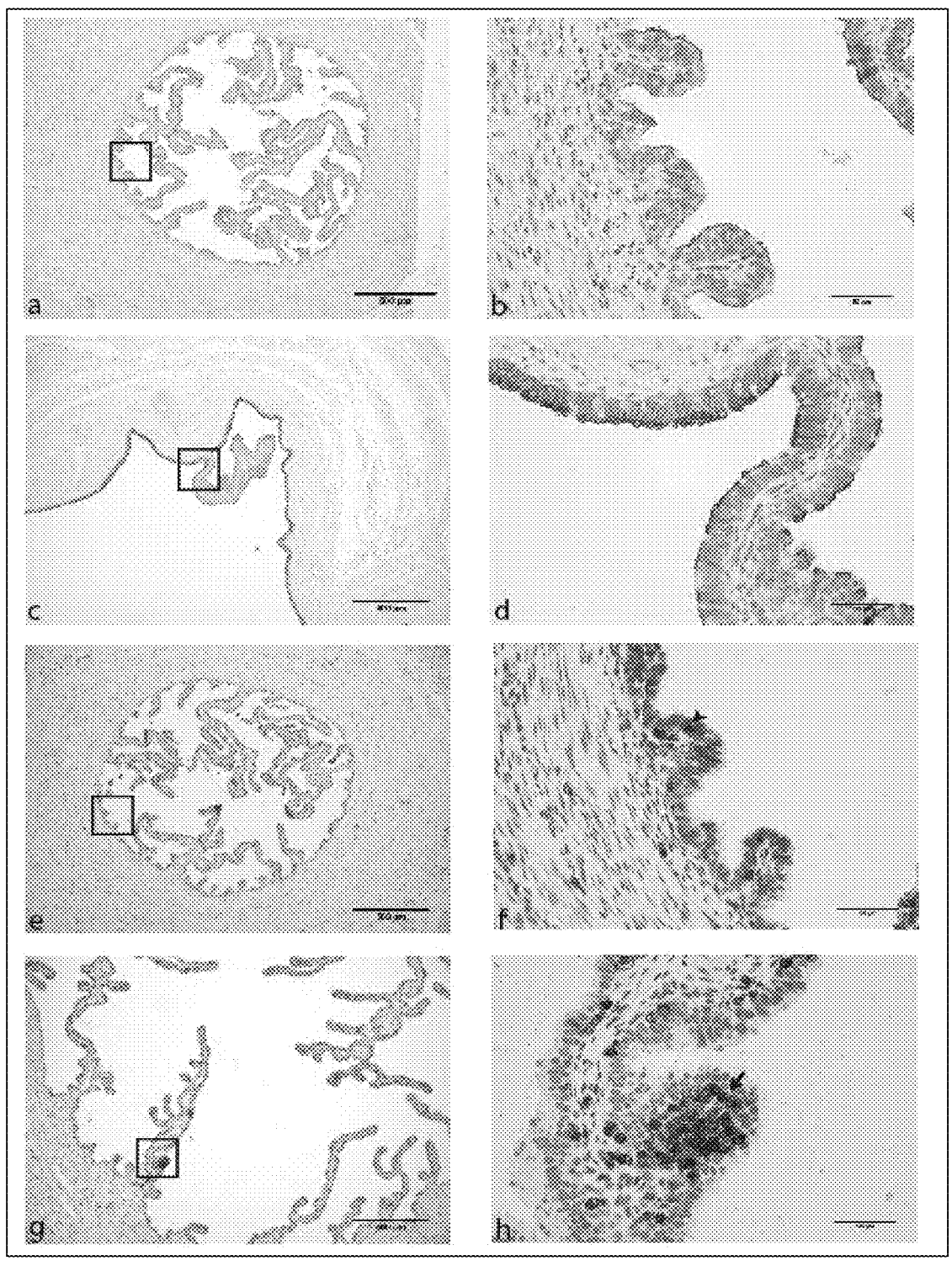
FIGS. 7A-H show results of an immunohistochemistry assay, demonstrating abundance of mesothelin (a through d) and CD45 (e through h).

To determine mesothelin tissue localization immunohistochemistry (IHC) analysis was carried out in representative fallopian tissues sections from hydrosalpinx- and healthy controls. FIG. 7 shows a protein abundance for MSLN and CD45 as assayed by immunohistochemistry. Micrographs 7a through 7d represent results from immunohistochemical detection of membrane bound mesothelin in fallopian tissue sections from healthy control (a and b) and hydrosalpinx-(c and d) with monoclonal anti-mesothelin antibody. Micrograms 7e through 7h represent results from immunohistochemical detection of cluster of differentiation 45 (CD45) in fallopian tissue sections from healthy control (7e and 7f) and hydrosalpinx (7g and 7h) with monoclonal anti-CD45 antibody. Micrographs in the right panel including: 7b, 7d, 7f and 7h are 40× of the area highlighted within squares on micrographs in the left panel.

A very strong immunostaining for MSLN observed in hydrosalpinx (FIGS. 7c and 7d) unlike what was observed in the healthy control (FIGS. 7a and b) clearly elucidated over-abundant membrane bound MSLN in hydrosalpinx. It also appeared that there was a mild to moderate degree of cytoplasmic staining associated with the membrane staining in the hydrosalpinx but not in the healthy control. Furthermore, this result suggests that the over-abundant soluble MSLN in the hydrosalpinx fluid may have been due to overexpression and subsequently an active shedding of the surface MSLN which is a very common phenomenon for MSLN expression pattern in the cancer pathology (26, 30). It is also apparent that the mucosa folds seen in the healthy fallopian tube, FIG. 7 a, in the most part disappears in hydrosalpinx tube, FIG. 7c, leaving behind a hollow and distended tube.

In addition, IHC analysis for CD45, shown in FIGS. 7e and 7f, clearly shows sparingly distributed infiltrating inflammatory cells within the mucosa and smooth muscles (arrow head) of the healthy tubal tissue. Unlike in the healthy tissue, CD45+ cells appear to be more and clustered within the mucosa of hydrosalpinx tissue (FIGS. 7g and 7h). Within the mucosa, it is also apparent from CD45+ leucocytes stain (FIGS. 7f and 7h) that CD45+ cells are localized close to the lumen side of the columnar epithelial cells. However, there was no apparent co-localization of CD45+ cells with the MLSN expressing columnar epithelial cells suggesting that mucosa epithelium rather than CD45+ cells were the sole source of MSLN consistent with the previous reports (34).

Figure 15:
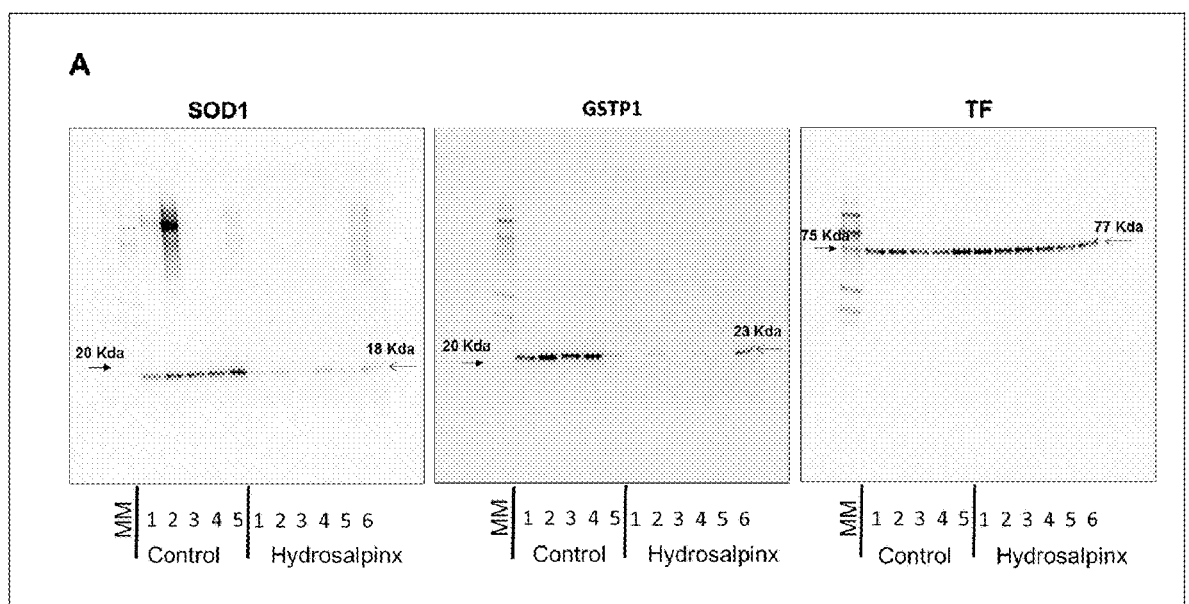
FIG. 15 provides graphical representation of full length blot images related to FIG. 6.
Figure 15:
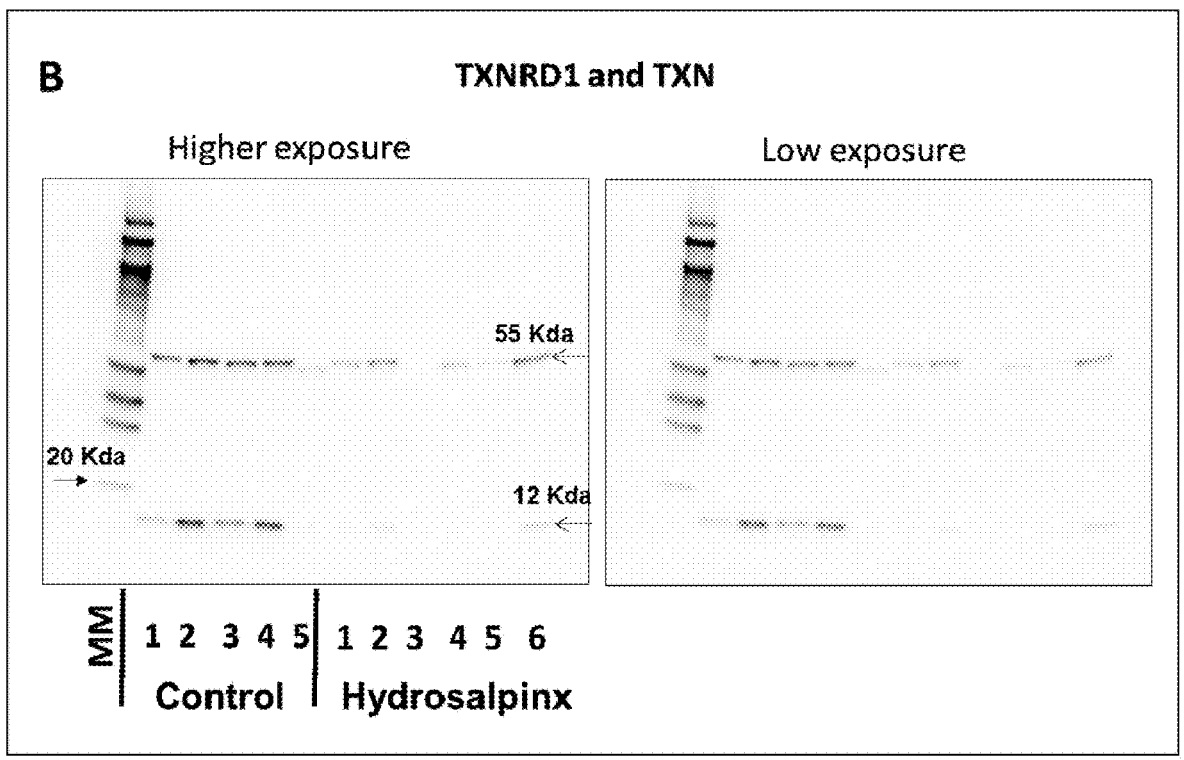
Figure 15:
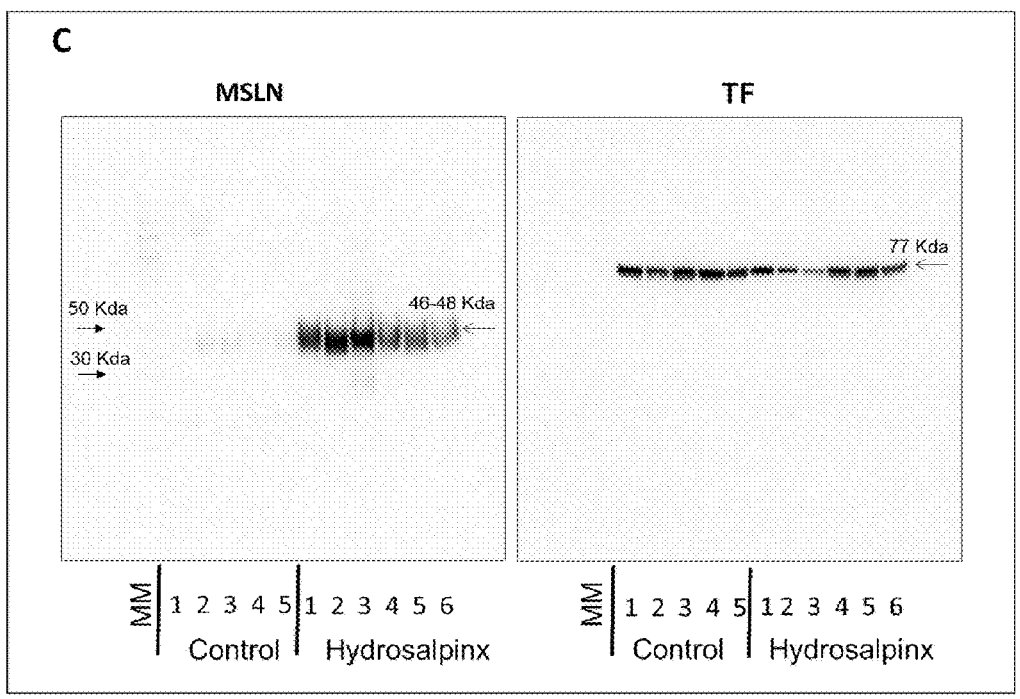

Example 7: Plasma Mesothelin Levels in Subjects with Hydrosalpinx and Healthy Fertile Control To determine whether mesothelin shed into the peripheral blood and to accurately measure it, plasma collected from women with hydrosalpinx and healthy fertile control were analyzed using quantikine ELISA. The concentration of mesothelin (ng/mL) in each plasma sample was determined using a calibration curve (FIG. 13) generated using human mesothelin standard. FIG. 15 provides graphical representation of full length blot images related to FIG. 6. (A) Full length images for SOD1 and GSTP1 and TF. B) Full length image for TXNRD1 and TXN with high contrast (left) and low contrast (right). (C) Full length images for MSNL and TF. (D) CD59 with higher and lower magnification along with TF. Each blot in each panel with the exception of blot in panel A has been stripped once for TF analysis as a loading control. Solid arrow denotes the nearest molecular ladder and open arrow indicates the predicted molecular weight of each target.

Figure 8:
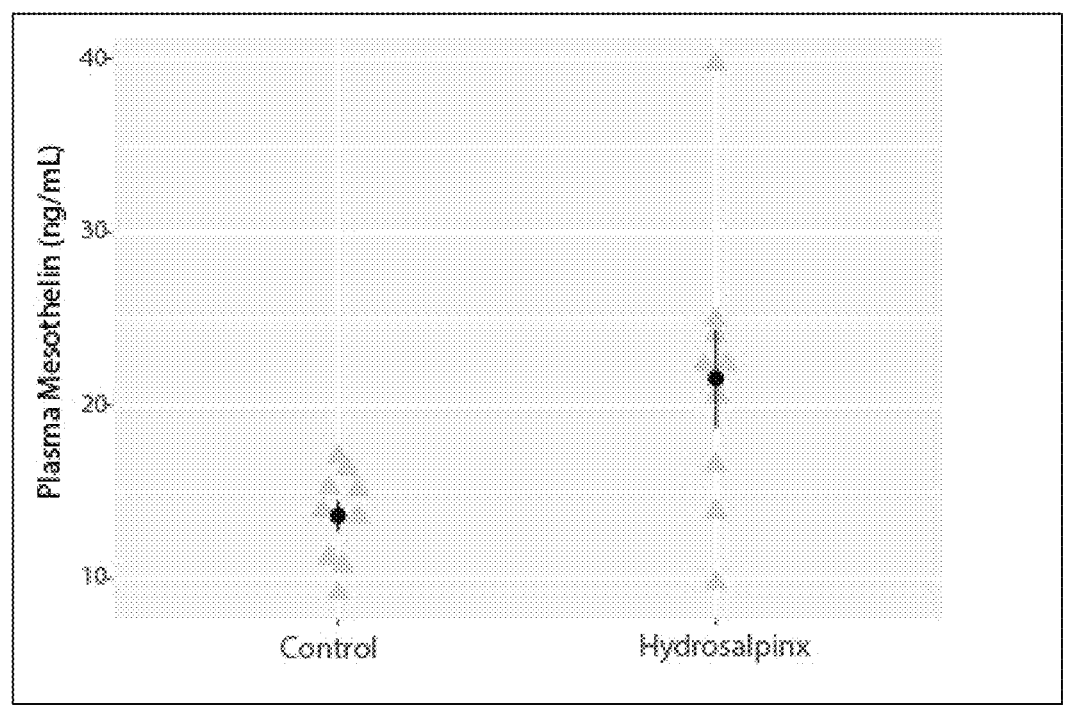
FIG. 8 is a schematic scatter plot of plasma mesothelin in women with hydrosalpinx and healthy fertile controls.
Figure 14:
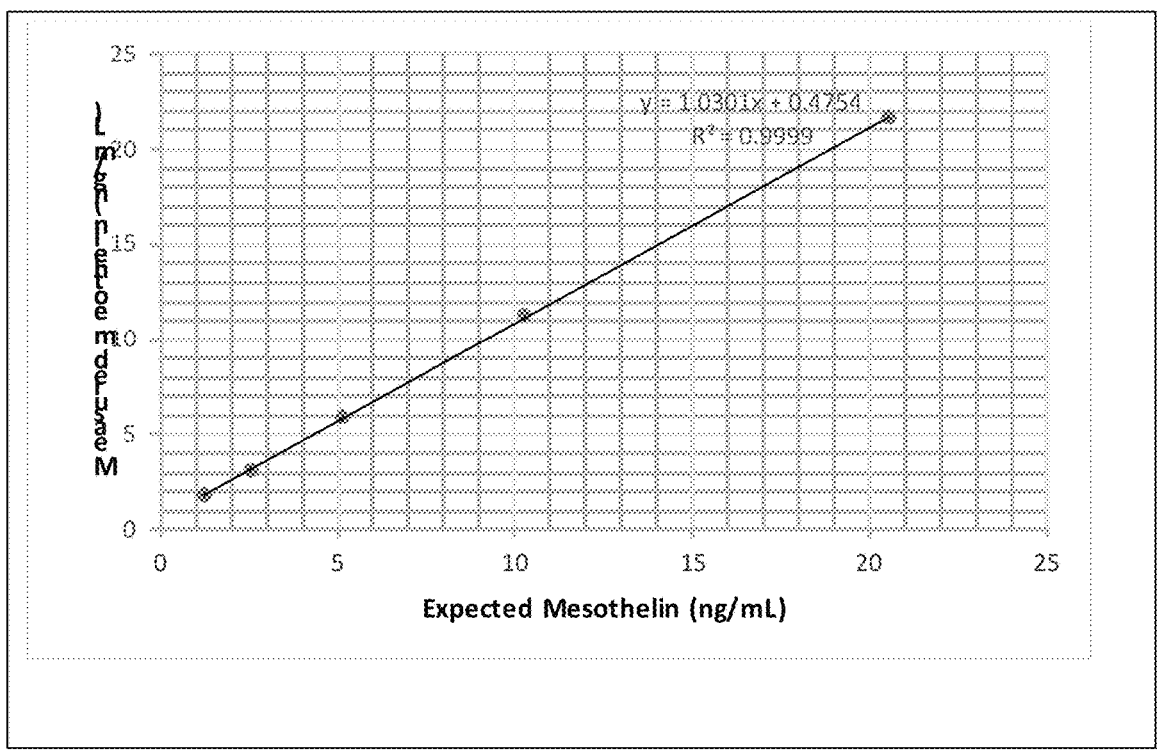
FIG. 14 is a graphical representation of results from a linearity study of mesothelin in plasma from women with hydrosalpinx by ELISA.

The scatterplot of plasma mesothelin in women with hydrosalpinx (n=9) and healthy fertile controls (n=9) is shown in FIG. 8. Mean and standard error from the mean represented with black circle and lines respectively. The scatter plot of individual data point (light blue triangle), and the mean (black circle with an error bar) for each group shown in FIG. 8. The mean plasma mesothelin levels in women with hydrosalpinx was 21.52±2.81 ng/mL, and it was significantly different from healthy control, 13.60±0.89 ng/mL ($p<0.05$). Of the nine women with hydrosalpinx who had elevated mesothelin levels in the tubal fluid (FIG. 6, Table 1, and Table 3) six (67%) had elevated plasma mesothelin levels. Linearity of the assay was also tested using plasma with a higher concentration of mesothelin. These results are shown in FIG. 14. FIG. 14 is a graphical representation of results from a linearity study of mesothelin ELISA. A plasma specimen containing 20.56 ng/mL of mesothelin was serially diluted with calibration diluent to produce the expected concentrations of serum mesothelin (x-axis) with the values within the dynamic range of the assay.

Example 8: Discussion of Examples 1-7

The adverse effects of hydrosalpinx not only on the physiology and morphology of the fallopian tube but also on the outcome of IVF have been well documented (11, 35-38). Examination of molecular changes in the fallopian tube lavage upon hydrosalpinx-formation is necessary to understand the mechanisms underlying hydrosalpinx mediated tubal damage, chronic pelvic inflammatory disease, impaired IVF successes and is central to the discovery of novel diagnostic and treatment options. In this study, we have focused on proteomics abundant changes in fallopian tube lavage, to understand the host responses and/or possible mechanisms that are responsible for hydrosalpinx pathology. We have identified a total of 519 proteins in both the healthy lavage and hydrolapinx fluid combined using a label free shotgun proteomics platform. Of these proteins, we report changes in abundance for over 110 proteins in hydrosalpinx fluids compared to lavages of healthy fallopian tube.

Mesothelin and its Binding Partners are Over-Abundant in Hydrosalpinx

Among over-abundant proteins in hydrosalpinx were mesothelin (MSLN) and binding partners MUC1, MUC5B, and MUC16. These proteins are intimately associated with inflammation and cancer pathophysiology with mesothelin levels highly correlated with mucin levels in several types of human cancers (30, 39, 40). MSLN expression and its distribution in normal human tissue is limited to the mesothelial cells lining of the pleura, peritoneum, and pericardium (41). However, it is highly expressed in many human cancers (30, 41) and actively shed from cell surface, generating an antigen pool in the circulation and the tumor interstitial space. Like in the tumor microenvironment, in the occluded fallopian tube filled with hydrosalpinx the expression level of MSLN both the bound, FIGS. 7c and d, and soluble (Table 3, Table 1, FIGS. 6a, and 6b) is overwhelmingly high. In addition, quantitative ELISA for plasma mesothelin clearly showed (FIG. 8) elevated levels of mesothelin in 67% of patients with hydrosalpinx.

Unlike mesothelin, the different isoforms of mucins are ubiquitous and they are produced by epithelial tissues. Mucins can form gels; therefore, they are key components in most gel-like secretions, serving functions from lubrication to cell signaling, to forming chemical barriers. In addition, expression of cell-surface and gel-forming mucins can be upregulated by inflammatory cytokines such as interleukins, interferons, tumor necrosis factor-α, nitric-oxide (42-44). It has been shown that Neutrophils stimulate increases in production of both gel-forming and cell-surface mucins by mucosal epithelial cells (45-47). These reports and the results from this study may have provided link between mucins, innate mucosal immunity, and mucosal inflammatory responses.

The co-overexpression of MSLN along with several mucins in many adenocarcinomas has been implicated to have a role in cell adherence, cell survival/proliferation, tumor progression, and chemo-resistance (26, 48). Mice in which the mesothelin gene had been inactivated appeared perfectly normal (49), they bred normally, had normal blood counts, and grew to normal size (49). Even though MSLN role in cancer is still unclear and may be cancer type specific, it has several features mentioned above which make it potential target for cancer diagnosis and therapy (50). As a result, several pre-clinical and phase I/II clinical trials are currently evaluating antibodies against MSLN and mucins as therapeutic alternatives (51-54). Inventors have discovered herein an overabundance of MSLN and its binding partners MUC1, and MUC16 in hydrosalpinx compared to normal lavage. Overabundances of these set of proteins and their possible functions have not been reported previously with hydrosalpinx. In addition, the overlapping pathophysiology involving MSNL between cancer and hydrosalpinx is yet to be determined. However, this result demonstrate that hydrosalpinx shares a molecular target with tubal and/or ovarian cancer pathology. It is possible that mesothelin overexpression with hydrosalpinx precedes tubule and/or ovarian cancer. Mesothelin is related to the disease process of hydrosalpinx that may be unconnected to the development of cancer. In this case it would be the first instance of mesothelin overexpression in the context of a disease process unrelated to cancer. The identification of mesothelin in the context of disease independent of cancer has never been described and has implication that may lead to a greater understanding of this disease process and the repurposing of anticancer therapies for hydropsalpinx. The results from ELISA assay provided herein identifies plasma mesothelin as a biomarker for hydrosalpinx. This finding provides a useful diagnostic for hydrosalpinx, and for a test for tracking a response to therapy.

Analogues to ovarian cancer we also observed a significant increase of MSLN in plasma from patients with hydrosalpinx. Hydrosalpinx typically presents in sexually active woman at an average age of 25 years[79]. Ovarian cancer occurs predominately in woman middle age or older with a family history of cancer[80]. MSLN in the sera of patients with ovarian cancer and mesothelioma has been identified as diagnostic biomarker[32,81]. It is possible that MSLN has utility as a non-invasive diagnostic biomarker for hydrosalpinx in younger woman with prior history of PID. However, it would not be able to distinguish hydrosalpinx in woman at risk for ovarian cancer. The other limitation worth noting, is that not all woman with higher concentrations of MSLN in tubal lavages exhibited greater amounts in their plasma (FIGS. 8, and 17). Similar heterogeneity in plasma MSLN concentrations among patients with mesothelioma and ovarian carcinoma have partly been attributed to the lack of MSLN expression in their tumors, and/or to differences in the study population[82]. However to elucidate the mechanisms that leads to the absence of plasma MSLN in subset of patients and to examine the diagnostic accuracy of plasma MSLN in patients with hydrosalpinx will require a larger cohort of patients.

Inflammatory Protein Modules are Over-Abundant in Hydrosalpinx

Nearly two third of the up regulated proteins in hydrosalpinx are associated with inflammatory responses. Subsets of these proteins are mainly involved in biological process that activate neutrophils movement and infiltration, promote binding of professional phagocytic cells, and phagocytosis by macrophages. These bio-processes suggest persistent extravasation of lymphocytes from the circulation into the site of occluded fallopian tube filed with hydrosalpinx and thus promote inflammatory responses. The other subsets are mainly part of complement systems and this subset incorporates 10 out of 37 known complement systems along with complement regulators including CD55 and CD59 are over abundant in hydrosalpinx. The co-over expression of over 25% of the complement proteins, via enrichment analysis, predicts the significant activation of the complement system in the hydrosalpinx (ref FIG. 3). As such, the function of the complement system has classically been thought to be rapid recognition and opsonic tagging of the microbial intruders to facilitate elimination of pathogens and support the development of adaptive immune responses (55-57). However, in the past few decades compelling evidences have shown that complement systems have much broader functions in immune surveillance and homeostasis (55). Complement assists in the clearance of immune complexes, cellular debris, and apoptotic cell, and has been associated with the early development and tissue repair (58).

On the contrary, complement is also known to be pro-inflammatory and to cause necrotic cell death (59). The balance between clearance enhancing anti-inflammatory properties and necrosis-inducing pro-inflammatory actions of complement may be crucial in determining the consequences of apoptotic cell death in tissues. Whether the over-abundance of complement protein is protective or damaging in the context of hydrosalpinx pathology is yet to be determined. However, it is known that self-cells are normally protected from complement by membrane bound complement regulators including CD46, CD55 and CD59. Prior studies revealed loss of both cell bound CD46 and CD59 during neutrophil apoptosis in vitro, and this loss made the cells more susceptible to complement-mediated lysis (60). In the same study, the lost membrane bound CD46 and CD59 has shown being accumulated in the supernatant. Similarly, over-abundance of both CD55 and CD59 in the hydrosalpinx may have been accompanied with loss of membrane bound CD55 and CD59.

In addition, the soluble form of CD59 from urine has shown to retain its specific complement binding activity, but exhibits greatly reduced ability to inhibit complement membrane attack (28). In the current study, the accumulation of soluble CD55 and CD59 coupled with an increase in complement-associated proteins and inflammatory cytokines suggests that complement mediated lytic processes may contribute to the striking mucosa fold loss and tissue damage observed in tubes affected with hydrosalpinx. Mucosa fold loss has been correlated with poor recovery of fallopian tube function and permanent loss of fertility (61). Importantly, a recent study also suggest that complement is not a strictly intravascular system; instead, local secretion of complement components by tissue and infiltrating cells, and potentially even intracellular complement turnover, contribute to the overall complement response in many circumstances (62, 63). In this regard, over-abundant complements in the hydrosalpinx may have been from local secretion. Taking together our results suggest that complement activation can be one of the mechanisms by which hydrosalpinx orchestrate chronic inflammatory process, the different degrees of tubal mucosa fold loss, and tubal tissue damage.

Dysregulated Protein Modules in Hydrosalpinx

Among the dysregulated proteins in hydrosalpinx fluid relative to lavages from healthy controls were detoxification enzymes involved in the ROS defense mechanism. Their down-regulation is predicted to result in decreases in hydrogen peroxide metabolism and subsequently, increases in reactive oxidative species (ref FIG. 4). Oxidative stress is a central feature of a number of inflammatory pathologies associated with infertility (64, 65) and strongly contributes to the embryotoxicity of hydrosalpingeal fluid (66).

The expression and activity of detoxification enzymes within the Fallopian tube is critical for normal reproductive physiology. Intratubal expression of superoxide dismutase 1 (SOD1), glutathione S-transferase pi 1 (GSTP1), thioredoxin (TXN) and peroxiredoxin (PRX) are induced by the presence of gametes in the oviduct, highlighting the importance of oviductal regulation of ROS for successful fertilization, embryo cleavage and/or embryo transit (20, 67). Recognition of the beneficial effects of SOD upon sperm viability and motility has made its addition to sperm cryopreservation media routine (68, 69). Furthermore, the addition of antioxidant enzymes such as SOD and catalase (CAT) to oocyte in vitro maturation (IVM) media results in improved fertilization rates and embryonic cleavage rates (70) whereas the addition of ROS such as xanthine and xanthine oxidase decreases both fertilization and embryonic cleavage rate (70). Studies in the bovine oviduct revealed that antioxidant enzymes such as glutathione peroxidase (GPX1), catalase (CAT) and the major cellular antioxidant GSH normally increase over the course of the estrus cycle (71). Additionally, the level of SOD in the bovine oviduct epithelium and its activity in the oviductal fluid remain at a high level throughout the estrus cycle (71). Consistent with these preclinical observations, we noted increased expression of SOD1 in lavage fluid from healthy Fallopian tubes irrespective of menstrual cycle phase (FIG. 6d). However, in hydrosalpinx fluid, down-regulation of key redox pathway enzymes have been identified herein, including GSTP1 (log 2FC−6.30; P<0.02), PRDX5 (log 2FC−5.31; P<0.001), TXN (log 2FC−2.33; P<0.05), PRDX6 (log 2FC−2.06; P<0.05) and SOD1 (log 2FC−6.76; P<0.05).

The co-dysregulation of these key detoxification enzymes in hydrosalpinx contributes to a microenvironment of increased oxidative stress detrimental to both gamete viability and early embryo development. These findings support increased inflammation and oxidative stress as the molecular basis for the observed embryotoxicity of hydrosalpingeal fluid likely underpinning the observed impairment of embryonic implantation in IVF.

Key mediators in mitigating ROS mediated cell death were also decreased in the hydrosalpinx fluid compared to fluid from healthy Fallopian tubes. ROS alter most cellular molecules such as lipids, proteins and nucleic acids and if not resolved through both enzymatic and non-enzymatic antioxidation pathways, lead to cell death. Heat shock protein family members (HSPB1/HSPA1A/HSPA1B), aldolase (ALDOA), selenium binding protein 1 (SELENBP1) and protein/nucleic acid deglycase DJ-1 (PARK7) mediate protection against stress, cell death and tissue necrosis by attenuating cellular stress (73-75). HSPB1 prevents apoptosis via directly inhibiting caspases (CASP9 and CASP3) and dysregulation of HSPB1 results in cell death (76). In addition to its function in glycolysis, glyceraldehyde-3-phosphae dehydrogenase (GAPDH) has an important role in DNA repair and replication, post-transcriptional regulation, gene expression and cell death (77, 78). In hydrosalpinx fluid, a decreased expression of SELENBP1 (log 2FC−3.39; $P<0.001$), ALDOA (log 2FC−2.71; $P<0.001$), PARK7 (log 2FC−2.29; $P<0.05$), HSPB1 (log 2FC−1.73; $P<0.01$), HSPA2 (log 2FC−1.6; $P<0.01$) and GAPDH (log 2FC−1.9; $P<0.05$) was observed. The co-down regulation of proteins that are involved in removing ROS with proteins that are directly associated with prevention of cell death contribute to a cytotoxic environment in hydrosalpinx characterized by ROS mediated cell death, tissue necrosis and complement mediated tissue lysis.

One of the benefits of the system and method embodiments herein include the ability obtain tubal samples at the time of MTA for analysis of the tubal proteome. Hormonal confirmation as to menstrual cycle phase allows analysis of potential cycle related influences on the molecular signatures of tubal fluid specimens. In some embodiments, tubal lavages were performed with gentle infusion on a saline rinsed surgical field and only specimens with <1% blood contaminants were included in the study.

Expression analysis using a discovery shotgun proteomics spectral counting approach has allowed for the identification of statistically significant differential expression of 116 proteins. Significant up-regulation of mesothelin in hydrosalpinx is a novel finding that has diagnostic and therapeutic implications as described herein. The ELISA assay results in the plasma suggest particular benefits of plasma mesothelin level as a diagnostic biomarker. Currently, there are no diagnostic laboratory test for hydrosalpinx.

The results enumerated herein demonstrate enrichment of the complement pathway which may mediate tubal mucosal fold damage associated with increased ectopic pregnancy risk in the setting of hydrosalpinx-affected Fallopian tubes. Down-regulation of detoxification proteins and proteins that mitigate ROS-mediated cell damage are likely to contribute to the embryotoxicity of hydrosalpingeal fluid that contributes to observed reductions in fertility in affected women. Differentially expressed proteins identified herein provide novel targets for diagnosis and treatment of hydrosalpinx.

REFERENCES

1. Brunham, R. C., Gottlieb, S. L., and Paavonen, J. (2015) Pelvic inflammatory disease. *The New England journal of medicine* 372, 2039-2048
2. Leng, Z., Moore, D. E., Mueller, B. A., Critchlow, C. W., Patton, D. L., Halbert, S. A., and Wang, S. P. (1998) Characterization of ciliary activity in distal Fallopian tube biopsies of women with obstructive tubal infertility. *Human reproduction* 13, 3121-3127
3. Practice Committee of the American Society for Reproductive, M. (2015) Role of tubal surgery in the era of assisted reproductive technology: a committee opinion. *Fertility and sterility* 103, e37-43
4. Zeyneloglu, H. B., Arici, A., and Olive, D. L. (1998) Adverse effects of hydrosalpinx on pregnancy rates after in vitro fertilization-embryo transfer. *Fertility and sterility* 70, 492-499
5. Camus, E., Poncelet, C., Goffinet, F., Wainer, B., Merlet, F., Nisand, I., and Philippe, H. J. (1999) Pregnancy rates after in-vitro fertilization in cases of tubal infertility with and without hydrosalpinx: a meta-analysis of published comparative studies. *Human reproduction* 14, 1243-1249
6. Johnson, N., van Voorst, S., Sowter, M. C., Strandell, A., and Mol, B. W. (2010) Surgical treatment for tubal disease in women due to undergo in vitro fertilisation. *The Cochrane database of systematic reviews*, CD002125
7. Sagoskin, A. W., Lessey, B. A., Mottla, G. L., Richter, K. S., Chetkowski, R. J., Chang, A. S., Levy, M. J., and Stillman, R. J. (2003) Salpingectomy or proximal tubal occlusion of unilateral hydrosalpinx increases the potential for spontaneous pregnancy. *Human reproduction* 18, 2634-2637
8. Practice Committee of American Society for Reproductive Medicine in collaboration with Society of Reproductive, S. (2008) Salpingectomy for hydrosalpinx prior to in vitro fertilization. *Fertility and sterility* 90, S66-68
9. Hammadieh, N., Coomarasamy, A., Ola, B., Papaioannou, S., Afnan, M., and Sharif, K. (2008) Ultrasound-guided hydrosalpinx aspiration during oocyte collection improves pregnancy outcome in IVF: a randomized controlled trial. *Human reproduction* 23, 1113-1117
10. Van Voorhis, B. J., Sparks, A. E., Syrop, C. H., and Stovall, D. W. (1998) Ultrasound-guided aspiration of hydrosalpinges is associated with improved pregnancy and implantation rates after in-vitro fertilization cycles. *Human reproduction* 13, 736-739
11. Andersen, A. N., Yue, Z., Meng, F. J., and Petersen, K. (1994) Low implantation rate after in-vitro fertilization in patients with hydrosalpinges diagnosed by ultrasonography. *Human reproduction* 9, 1935-1938
12. Savaris, R. F., and Giudice, L. C. (2007) The influence of hydrosalpinx on markers of endometrial receptivity. *Seminars in reproductive medicine* 25, 476-482
13. Song, Y., Wang, Q., Huang, W., Xiao, L., Shen, L., and Xu, W. (2012) NF kappaB expression increases and CFTR and MUC1 expression decreases in the endometrium of infertile patients with hydrosalpinx: a comparative study. *Reproductive biology and endocrinology: RB&E* 10, 86
14. Strandell, A. (2000) The influence of hydrosalpinx on IVF and embryo transfer: a review. *Human reproduction update* 6, 387-395
15. Seli, E., Kayisli, U. A., Cakmak, H., Bukulmez, O., Bildirici, I., Guzeloglu-Kayisli, O., and Arici, A. (2005) Removal of hydrosalpinges increases endometrial leukaemia inhibitory factor (LIF) expression at the time of the implantation window. *Human reproduction* 20, 3012-3017
16. Daftary, G. S., Kayisli, U., Seli, E., Bukulmez, O., Arici, A., and Taylor, H. S. (2007) Salpingectomy increases peri-implantation endometrial HOXA10 expression in women with hydrosalpinx. *Fertility and sterility* 87, 367-372
17. Daftary, G. S., and Taylor, H. S. (2002) Hydrosalpinx fluid diminishes endometrial cell HOXA10 expression. *Fertility and sterility* 78, 577-580
18. Lane, M., and Gardner, D. K. (2007) Embryo culture medium: which is the best?*Best practice & research. Clinical obstetrics & gynaecology* 21, 83-100
19. Gardner, D. K., Lane, M., Calderon, I., and Leeton, J. (1996) Environment of the preimplantation human embryo in vivo: metabolite analysis of oviduct and uterine fluids and metabolism of cumulus cells. *Fertility and sterility* 65, 349-353
20. Georgiou, A. S., Sostaric, E., Wong, C. H., Snijders, A. P., Wright, P. C., Moore, H. D., and Fazeli, A. (2005) Gametes alter the oviductal secretory proteome. *Molecular & cellular proteomics: MCP* 4, 1785-1796
21. Love, M. I., Huber, W., and Anders, S. (2014) Moderated estimation of fold change and dispersion for RNA-seq data with DESeq2. *Genome biology* 15, 550

22. Anders, S., and Huber, W. (2010) Differential expression analysis for sequence count data. *Genome biology* 11, R106
23. Shao, R., Wang, X., Weijdegard, B., Norstrom, A., Fernandez-Rodriguez, J., Brannstrom, M., and Billig, H. (2012) Coordinate regulation of heterogeneous nuclear ribonucleoprotein dynamics by steroid hormones in the human fallopian tube and endometrium in vivo and in vitro. *American journal of physiology. Endocrinology and metabolism* 302, E1269-1282
24. Shao, R., Norstrom, A., Weijdegard, B., Egecioglu, E., Fernandez-Rodriguez, J., Feng, Y., Stener-Victorin, E., Brannstrom, M., and Billig, H. (2011) Distinct expression pattern of Dicer1 correlates with ovarian-derived steroid hormone receptor expression in human Fallopian tubes during ovulation and the midsecretory phase. *The Journal of clinical endocrinology and metabolism* 96, E869-877
25. Ajonuma, L. C., Ng, E. H., and Chan, H. C. (2002) New insights into the mechanisms underlying hydrosalpinx fluid formation and its adverse effect on IVF outcome. *Human reproduction update* 8, 255-264
26. Chang, K., and Pastan, I. (1996) Molecular cloning of mesothelin, a differentiation antigen present on mesothelium, mesotheliomas, and ovarian cancers. *Proceedings of the National Academy of Sciences of the United States of America* 93, 136-140
27. Weinstock, C., Anliker, M., and von Zabern, I. (2015) CD59: A long-known complement inhibitor has advanced to a blood group system. *Immunohematology* 31, 145-151
28. Meri, S., Lehto, T., Sutton, C. W., Tyynela, J., and Baumann, M. (1996) Structural composition and functional characterization of soluble CD59: heterogeneity of the oligosaccharide and glycophosphoinositol (GPI) anchor revealed by laser-desorption mass spectrometric analysis. *The Biochemical journal* 316 (Pt 3), 923-935
29. Rudd, P. M., Morgan, B. P., Wormald, M. R., Harvey, D. J., van den Berg, C. W., Davis, S. J., Ferguson, M. A., and Dwek, R. A. (1997) The glycosylation of the complement regulatory protein, human erythrocyte CD59. *The Journal of biological chemistry* 272, 7229-7244
30. Pastan, I., and Hassan, R. (2014) Discovery of mesothelin and exploiting it as a target for immunotherapy. *Cancer research* 74, 2907-2912
31. Onda, M., Nagata, S., Ho, M., Bera, T. K., Hassan, R., Alexander, R. H., and Pastan, I. (2006) Megakaryocyte potentiation factor cleaved from mesothelin precursor is a useful tumor marker in the serum of patients with mesothelioma. *Clinical cancer research: an official journal of the American Association for Cancer Research* 12, 4225-4231
32. Scholler, N., Fu, N., Yang, Y., Ye, Z., Goodman, G. E., Hellstrom, K. E., and Hellstrom, I. (1999) Soluble member(s) of the mesothelin/megakaryocyte potentiating factor family are detectable in sera from patients with ovarian carcinoma. *Proceedings of the National Academy of Sciences of the United States of America* 96, 11531-11536
33. Pannala, V. R., and Dash, R. K. (2015) Mechanistic characterization of the thioredoxin system in the removal of hydrogen peroxide. *Free radical biology & medicine* 78, 42-55
34. Hassan, R., Kreitman, R. J., Pastan, I., and Willingham, M. C. (2005) Localization of mesothelin in epithelial ovarian cancer. *Applied immunohistochemistry & molecular morphology: AIMM* 13, 243-247
35. Patil, M. (2009) Assessing tubal damage. *Journal of human reproductive sciences* 2, 2-11
36. Zalel, Y., Soriano, D., Lipitz, S., Mashiach, S., and Achiron, R. (2000) Contribution of color Doppler flow to the ultrasonographic diagnosis of tubal abnormalities. *Journal of ultrasound in medicine: official journal of the American Institute of Ultrasound in Medicine* 19, 645-649
37. Aboulghar, M. A., Mansour, R. T., and Serour, G. I. (1998) Controversies in the modern management of hydrosalpinx. *Human reproduction update* 4, 882-890
38. Strandell, A., and Lindhard, A. (2002) Why does hydrosalpinx reduce fertility? The importance of hydrosalpinx fluid. *Human reproduction* 17, 1141-1145
39. Kufe, D. W. (2009) Mucins in cancer: function, prognosis and therapy. *Nature reviews. Cancer* 9, 874-885
40. Cheever, M. A., Allison, J. P., Ferris, A. S., Finn, O. J., Hastings, B. M., Hecht, T. T., Mellman, I., Prindiville, S. A., Viner, J. L., Weiner, L. M., and Matrisian, L. M. (2009) The prioritization of cancer antigens: a national cancer institute pilot project for the acceleration of translational research. *Clinical cancer research: an official journal of the American Association for Cancer Research* 15, 5323-5337
41. Chang, K., Pastan, I., and Willingham, M. C. (1992) Isolation and characterization of a monoclonal antibody, K1, reactive with ovarian cancers and normal mesothelium. *International journal of cancer* 50, 373-381
42. Enss, M. L., Cornberg, M., Wagner, S., Gebert, A., Henrichs, M., Eisenblatter, R., Beil, W., Kownatzki, R., and Hedrich, H. J. (2000) Proinflammatory cytokines trigger MUC gene expression and mucin release in the intestinal cancer cell line LS180. *Inflammation research: official journal of the European Histamine Research Society . . . [et al.]* 49, 162-169
43. Smirnova, M. G., Kiselev, S. L., Birchall, J. P., and Pearson, J. P. (2001) Up-regulation of mucin secretion in HT29-MTX cells by the pro-inflammatory cytokines tumor necrosis factor-alpha and interleukin-6. *European cytokine network* 12, 119-125
44. Koga, T., Kuwahara, I., Lillehoj, E. P., Lu, W., Miyata, T., Isohama, Y., and Kim, K. C. (2007) TNF-alpha induces MUC1 gene transcription in lung epithelial cells: its signaling pathway and biological implication. *American journal of physiology. Lung cellular and molecular physiology* 293, L693-701
45. Lundgren, J. D., Rieves, R. D., Mullol, J., Logun, C., and Shelhamer, J. H. (1994) The effect of neutrophil protenase enzymes on the release of mucus from feline and human airway cultures. *Respiratory medicine* 88, 511-518
46. Kuwahara, I., Lillehoj, E. P., Hisatsune, A., Lu, W., Isohama, Y., Miyata, T., and Kim, K. C. (2005) Neutrophil elastase stimulates MUC1 gene expression through increased Sp1 binding to the MUC1 promoter. *American journal of physiology. Lung cellular and molecular physiology* 289, L355-362
47. Fischer, B. M., and Voynow, J. A. (2002) Neutrophil elastase induces MUC5AC gene expression in airway epithelium via a pathway involving reactive oxygen species. *American journal of respiratory cell and molecular biology* 26, 447-452
48. Rump, A., Morikawa, Y., Tanaka, M., Minami, S., Umesaki, N., Takeuchi, M., and Miyajima, A. (2004) Binding of ovarian cancer antigen CA125/MUC16 to mesothelin mediates cell adhesion. *The Journal of biological chemistry* 279, 9190-9198
49. Bera, T. K., and Pastan, I. (2000) Mesothelin is not required for normal mouse development or reproduction. *Molecular and cellular biology* 20, 2902-2906

50. Hassan, R., Bera, T., and Pastan, I. (2004) Mesothelin: a new target for immunotherapy. *Clinical cancer research: an official journal of the American Association for Cancer Research* 10, 3937-3942
51. Hassan, R., Sharon, E., Thomas, A., Zhang, J., Ling, A., Miettinen, M., Kreitman, R. J., Steinberg, S. M., Hollevoet, K., and Pastan, I. (2014) Phase 1 study of the antimesothelin immunotoxin SS1P in combination with pemetrexed and cisplatin for front-line therapy of pleural mesothelioma and correlation of tumor response with serum mesothelin, megakaryocyte potentiating factor, and cancer antigen 125. *Cancer* 120, 3311-3319
52. Kreitman, R. J., Hassan, R., Fitzgerald, D. J., and Pastan, I. (2009) Phase I trial of continuous infusion anti-mesothelin recombinant immunotoxin SS1P. *Clinical cancer research: an official journal of the American Association for Cancer Research* 15, 5274-5279
53. Hassan, R., Kindler, H. L., Jahan, T., Bazhenova, L., Reck, M., Thomas, A., Pastan, I., Parno, J., O'Shannessy, D. J., Fatato, P., Maltzman, J. D., and Wallin, B. A. (2014) Phase II clinical trial of amatuximab, a chimeric antimesothelin antibody with pemetrexed and cisplatin in advanced unresectable pleural mesothelioma. *Clinical cancer research: an official journal of the American Association for Cancer Research* 20, 5927-5936
54. Yokokawa, J., Palena, C., Arlen, P., Hassan, R., Ho, M., Pastan, I., Schlom, J., and Tsang, K. Y. (2005) Identification of novel human CTL epitopes and their agonist epitopes of mesothelin. *Clinical cancer research: an official journal of the American Association for Cancer Research* 11, 6342-6351
55. Ricklin, D., Hajishengallis, G., Yang, K., and Lambris, J. D. (2010) Complement: a key system for immune surveillance and homeostasis. *Nature immunology* 11, 785-797
56. Merle, N. S., Church, S. E., Fremeaux-Bacchi, V., and Roumenina, L. T. (2015) Complement System Part I—Molecular Mechanisms of Activation and Regulation. *Frontiers in immunology* 6, 262
57. Merle, N. S., Noe, R., Halbwachs-Mecarelli, L., Fremeaux-Bacchi, V., and Roumenina, L. T. (2015) Complement System Part II: Role in Immunity. *Frontiers in immunology* 6, 257
58. Gaipl, U. S., Kuenkele, S., Voll, R. E., Beyer, T. D., Kolowos, W., Heyder, P., Kalden, J. R., and Herrmann, M. (2001) Complement binding is an early feature of necrotic and a rather late event during apoptotic cell death. *Cell death and differentiation* 8, 327-334
59. Koski, C. L., Ramm, L. E., Hammer, C. H., Mayer, M. M., and Shin, M. L. (1983) Cytolysis of nucleated cells by complement: cell death displays multi-hit characteristics. *Proceedings of the National Academy of Sciences of the United States of America* 80, 3816-3820
60. Jones, J., and Morgan, B. P. (1995) Apoptosis is associated with reduced expression of complement regulatory molecules, adhesion molecules and other receptors on polymorphonuclear leucocytes: functional relevance and role in inflammation. *Immunology* 86, 651-660
61. Fedele, L., Zamberletti, D., Marchini, M., Vercellini, P., and Cavalli, G. (1984) Degree of endosalpingeal deciliation (by S.E.M.) in hydrosalpinx is not prognostic for post-surgical fertility. *Acta Europaea fertilitatis* 15, 199-204
62. Kolev, M., Le Friec, G., and Kemper, C. (2014) Complement—tapping into new sites and effector systems. *Nature reviews. Immunology* 14, 811-820
63. Morgan, B. P., and Gasque, P. (1997) Extrahepatic complement biosynthesis: where, when and why? *Clinical and experimental immunology* 107, 1-7
64. Calogero, A. E., Condorelli, R. A., Russo, G. I., and La Vignera, S. (2017) Conservative Nonhormonal Options for the Treatment of Male Infertility: Antibiotics, Anti-Inflammatory Drugs, and Antioxidants. *BioMed research international* 2017, 4650182
65. Murphy, A. A., Palinski, W., Rankin, S., Morales, A. J., and Parthasarathy, S. (1998) Evidence for oxidatively modified lipid-protein complexes in endometrium and endometriosis. *Fertility and sterility* 69, 1092-1094
66. Bedaiwy, M. A., Goldberg, J. M., Falcone, T., Singh, M., Nelson, D., Azab, H., Wang, X., and Sharma, R. (2002) Relationship between oxidative stress and embryotoxicity of hydrosalpingeal fluid. *Human reproduction* 17, 601-604
67. Fazeli, A., Affara, N. A., Hubank, M., and Holt, W. V. (2004) Sperm-induced modification of the oviductal gene expression profile after natural insemination in mice. *Biology of reproduction* 71, 60-65
68. Roca, J., Rodriguez, M. J., Gil, M. A., Carvajal, G., Garcia, E. M., Cuello, C., Vazquez, J. M., and Martinez, E. A. (2005) Survival and in vitro fertility of boar spermatozoa frozen in the presence of superoxide dismutase and/or catalase. *Journal of andrology* 26, 15-24
69. Rossi, T., Mazzilli, F., Delfino, M., and Dondero, F. (2001) Improved human sperm recovery using superoxide dismutase and catalase supplementation in semen cryopreservation procedure. *Cell and tissue banking* 2, 9-13
70. Matsuoka, I., Fujino, Y., Ogita, S., and Inoue, M. (1995) Impact of erythrocytes on mouse embryonal development in vitro. *FEBS letters* 371, 297-299
71. Lapointe, J., and Bilodeau, J. F. (2003) Antioxidant defenses are modulated in the cow oviduct during the estrous cycle. *Biology of reproduction* 68, 1157-1164
72. Chanr, L. Y., Chiu, P. Y., and Lau, T. K. (2004) Hydrosalpinx fluid induced embryotoxicity and lipid peroxidation. *Reproductive toxicology* 19, 147-148
73. Creagh, E. M., Sheehan, D., and Cotter, T. G. (2000) Heat shock proteins—modulators of apoptosis in tumour cells. *Leukemia* 14, 1161-1173
74. Cohen, S. D., Pumford, N. R., Khairallah, E. A., Boekelheide, K., Pohl, L. R., Amouzadeh, H. R., and Hinson, J. A. (1997) Selective protein covalent binding and target organ toxicity. *Toxicology and applied pharmacology* 143, 1-12
75. Kabakov, A. E., Budagova, K. R., Malyutina, Y. V., Latchman, D. S., and Csermely, P. (2004) Pharmacological attenuation of apoptosis in reoxygenated endothelial cells. *Cellular and molecular life sciences: CMLS* 61, 3076-3086
76. Heinrich, J. C., Tuukkanen, A., Schroeder, M., Fahrig, T., and Fahrig, R. (2011) RP101 (brivudine) binds to heat shock protein HSP27 (HSPB1) and enhances survival in animals and pancreatic cancer patients. *Journal of cancer research and clinical oncology* 137, 1349-1361
77. Sirover, M. A. (2012) Subcellular dynamics of multifunctional protein regulation: mechanisms of GAPDH intracellular translocation. *Journal of cellular biochemistry* 113, 2193-2200
78. Sirover, M. A. (2011) On the functional diversity of glyceraldehyde-3-phosphate dehydrogenase: biochemical mechanisms and regulatory control. *Biochimica et biophysica acta* 1810, 741-751

79. Chu, J. et al. Salpingostomy in the treatment of hydrosalpinx: a systematic review and meta-analysis. *Hum Reprod* 30, 1882-1895 (2015).
80. McLemore, M. R., Miaskowski, C., Aouizerat, B. E., Chen, L. M. & Dodd, M. J. Epidemiological and genetic factors associated with ovarian cancer. *Cancer Nurs* 32, 281-288; quiz 289-290 (2009).
81. Robinson, B. W. et al. Mesothelin-family proteins and diagnosis of mesothelioma. *Lancet* 362, 1612-1616 (2003).
82. Hollevoet, K. et al. Serum mesothelin for diagnosing malignant pleural mesothelioma: an individual patient data meta-analysis. *Journal of clinical oncology: official journal of the American Society of Clinical Oncology* 30, 1541-1549 (2012).

TABLE 1

Relative fold changes for the selected proteins determine from verification western blot analysis of hydrosalpinx and healthy control tubal lavages.

| Protein | Log 2 fold change [a] | P-value (T-test) |
|---|---|---|
| MSLN | 5.38 | 2.69E−05 |
| CD59 | 12.25 | 0.0017 |
| GSTP1 | −6.30 | 0.027 |
| SOD1 | −6.76 | 8.02E−05 |
| TRX | −10.77 | 0.0010 |
| TRXR [b] | −3.89 | 0.045 |

[a] The log fold change is expressed as log ration between the mean intensity of immunoblot for the hydrosalpinx and healthy controls after normalization to transferrin.
[b] Protein identified via IPA network analysis.

TABLE 2

Patient Information for fallopian tube aspirates (hydrosalpinx) and lavages (from fertile controls undergoing tubal re-anastomosis). A total of 26 independent samples were used for shotgun proteomics. The additional independent control samples were used for western blot verification analysis presented in FIGS. 4B and C.

| | Healthy Control | Hydrosalpinx | t-Test p-value |
|---|---|---|---|
| Age (years) | 32.1 ± 1.0  25 \| 41 | 30.5 ± 2.0  24 \| 38 | 0.35 |
| Parity | 2.9 ± 0.3 | 1.4 ± 0.4 | $5.5 \times 10^{-5}$ |
| BMI | 26.1 ± 1.0 | 24.5 ± 1.6 | 0.28 |
| Serum Estradiol (pg/mL) | 140.2 ± 24.2 | 121.7 ± 19.8 | 0.26 |
| Serum Progesterone (ng/ml) | 3.9 ± 1.1 | 5.4 ± 1.3 | 0.38 |
| Cycle Phases, n patients: | | | |
| Menstrual (M) | 6 | 3 | |
| Proliferative (P) | 6 | 4 | |
| Early-Secretory (ES) | 4 | 2 | |
| Mid-Secretory (MS) | 4 | 1 | |
| Chi-Square Test | | 0.896 | |

TABLE 3

Differential proteome profile of tubal fluids from subjects with hydrosalpinx relative to lavages from healthy fertile donors.

| Accession | Protein identity | Log 2 Fold change | P-Adj | Biological Process |
|---|---|---|---|---|
| Q08380 | Galectin-3-binding protein OS = Homo sapiens GN = LGALS3BP PE = 1 SV = 1 − [LG3BP_HUMAN] | 6.38 | 9.79E−20 | Platelet degranulation, cell defense response, cell adhesion, activation of neutrophils & granulocytes |
| P10909 | Clusterin OS = Homo sapiens GN = CLU PE = 1 SV = 1 − [CLUS_HUMAN] | 2.3 | 5.67E−15 | Complement activation, cell death, innate immune response, recruitment of phagocytes |
| P01833 | Polymeric immunoglobulin receptor OS = Homo sapiens GN = PIGR PE = 1 SV = 4 − [PIGR_HUMAN] | 8.32 | 4.12E−11 | Immune Cell trafficking, immunoglobulin transcytosis in epithelial cells |
| Q13421 | Mesothelin OS = Homo sapiens GN = MSLN PE = 1 SV = 2 − [MSLN_HUMAN] | 4.2 | 1.29E−09 | Cell adhesion |
| P80188 | Neutrophil gelatinase-associated lipocalin OS = Homo sapiens GN = LCN2 PE = 1 SV = 2 − [NGAL_HUMAN] | 7.36 | 2.71E−09 | Innate immune response, activation of macrophages, recruitment of neutrophils, chemotaxis of neutrophils, ion transport, inflammation of mucosa |
| P02750 | Leucine-rich alpha-2-glycoprotein OS = Homo sapiens GN = LRG1 PE = 1 SV = 2 − [A2GL_HUMAN] | 2.23 | 4.44E−09 | Positive regulator of endothelial cell proliferation, positive regulation of agiogenesis |
| P10451 | Osteopontin OS = Homo sapiens GN = SPP1 PE = 1 SV = 1 − [OSTP_HUMAN] | 7.67 | 4.44E−09 | Inflammatory response, Osteoblast differentiation, cell adhesion, recruitment & accumulation of macrophages |
| P04745 | Alpha-amylase 1 OS = Homo sapiens GN = AMY1A PE = 1 SV = 2 − [AMY1_HUMAN] | 5.78 | 4.85E−09 | Cabohydrate metabolic process |
| Q14508 | WAP four-disulfide core domain protein 2 OS = Homo sapiens GN = WFDC2 PE = 1 SV = 2 − [WFDC2_HUMAN] | 5.1 | 8.08E−09 | Proteolysis |
| Q8WXI7 | Mucin-16 OS = Homo sapiens GN = MUC16 PE = 1 SV = 3 − [MUC16_HUMAN] | 7.55 | 1.51E−08 | Cell adhesion |
| P14384 | Carboxypeptidase M OS = Homo sapiens GN = CPM PE = 1 SV = 2 − [CBPM_HUMAN] | 7.25 | 2.23E−08 | peptide metabolic process, anatomical structure morphogenesis |
| P05155 | Plasma protease C1 inhibitor OS = Homo sapiens GN = SERPING1 PE = 1 SV = 2 − [IC1_HUMAN] | 1.89 | 5.09E−08 | complement activation, classical pathway, innate immune response, accumulation of granulocytes |

TABLE 3-continued

Differential proteome profile of tubal fluids from subjects with hydrosalpinx relative to lavages from healthy fertile donors.

| Accession | Protein identity | Log 2 Fold change | P-Adj | Biological Process |
|---|---|---|---|---|
| P12109 | Collagen alpha-1(VI) chain OS = Homo sapiens GN = COL6A1 PE = 1 SV = 3 - [CO6A1_HUMAN] | 6.84 | 1.75E-07 | cell adhesion, extracellular matrix organization, osteoblast differentiation, |
| P23142 | Fibulin-1 OS = Homo sapiens GN = FBLN1 PE = 1 SV = 4 - [FBLN1_HUMAN] | 7.39 | 2.08E-07 | integrin-mediated signaling pathway, embryo implantation, extracellular matrix organization |
| P05156 | Complement factor I OS = Homo sapiens GN = CFI PE = 1 SV = 2 - [CFAI_HUMAN] | 1.91 | 2.69E-07 | complement activation, classical pathway, regulation of complement activation, innate immune response, |
| O00391 | Sulfhydryl oxidase 1 OS = Homo sapiens GN = QSOX1 PE = 1 SV = 3 - [QSOX1_HUMAN] | 4.97 | 3.19E-07 | negative regulation of macroautophagy, cell redox homeostasis, oxidation-reduction process, |
| Q14515 | SPARC-like protein 1 OS = Homo sapiens GN = SPARCL1 PE = 1 SV = 2 - [SPRL1_HUMAN] | 4.33 | 7.85E-07 | signal transduction, anatomical structure development |
| Q86WI1 | Fibrocystin-L OS = Homo sapiens GN = PKHD1L1 PE = 2 SV = 2 - [PKHL1_HUMAN] | 6.27 | 9.12E-07 | immune response |
| Q16270 | Insulin-like growth factor-binding protein 7 OS = Homo sapiens GN = IGFBP7 PE = 1 SV = 1 - [IBP7_HUMAN] | 6.86 | 1.08E-06 | regulation of cell growth, cell adhesion, embryo implantation, |
| O00592 | Podocalyxin OS = Homo sapiens GN = PODXL PE = 1 SV = 2 - [PODXL_HUMAN] | 6.09 | 1.48E-06 | negative regulation of cell adhesion, cell migration, epithelial tube formation, |
| P12821 | Angiotensin-converting enzyme OS = Homo sapiens GN = ACE PE = 1 SV = 1 - [ACE_HUMAN] | 6.35 | 1.57E-06 | inflammatory response, activation of macrophages, neutrophil mediated immunity, activation of antigen presenting cells, blood vessel remodeling |
| P00747 | Plasminogen OS = Homo sapiens GN = PLG PE = 1 SV = 2 - [PLMN_HUMAN] | -1.71 | 1.57E-06 | platelet degranulation, accumulation of granulocytes, movement of monocytes extracellular matrix disassembly, tissue remodeling |
| P61769 | Beta-2-microglobulin OS = Homo sapiens GN = B2M PE = 1 SV = 1 - [B2MG_HUMAN] | 5.22 | 3.30E-06 | positive regulation of T cell mediated cytotoxicity, antigen processing and presentation of peptide antigen via MHC class I, negative regulation of neuron projection development, immune response |
| P15941 | Mucin-1 OS = Homo sapiens GN = MUC1 PE = 1 SV = 3 - [MUC1_HUMAN] | 4.2 | 3.78E-06 | response to hypoxia, DNA damage response, signal transduction |
| O43490 | Prominin-1 OS = Homo sapiens GN = PROM1 PE = 1 SV = 1 - [PROM1_HUMAN] | 6.3 | 4.77E-06 | retina layer formation, positive regulation of nephron tubule epithelial cell differentiation, atopic dermatitis |
| P02788 | Lactotransferrin OS = Homo sapiens GN = LTF PE = 1 SV = 6 - [TRFL_HUMAN] | 6.49 | 5.09E-06 | innate immune response in mucosa, ion transport, activation of neutrophils & macrophages |
| P36222 | Chitinase-3-like protein 1 OS = Homo sapiens GN = CHI3L1 PE = 1 SV = 2 - [CH3L1_HUMAN] | 5.76 | 7.18E-06 | activation of phagocytes, recruitment of neutrophils, carbohydrate metabolic process, chitin catabolic |
| Q12889 | Oviduct-specific glycoprotein OS = Homo sapiens GN = OVGP1 PE = 2 SV = 1 - [OVGP1_HUMAN] | 3.49 | 7.23E-06 | negative regulation of binding of sperm to zona pellucida |
| Q9BW30 | Tubulin polymerization-promoting protein family member 3 OS = Homo sapiens GN = TPPP3 PE = 1 SV = 1 - [TPPP3_HUMAN] | -2.78 | 8.55E-06 | microtubule bundle formation |
| P09211 | Glutathione S-transferase P OS = Homo sapiens GN = GSTP1 PE = 1 SV = 2 - [GSTP1_HUMAN] | -2.24 | 1.41E-05 | response to reactive oxygen species, negative regulation of acute inflammatory response |
| P13671 | Complement component C6 OS = Homo sapiens GN = C6 PE = 1 SV = 3 - [CO6_HUMAN] | 3.34 | 1.43E-05 | complement activation |
| Q13228 | Selenium-binding protein 1 OS = Homo sapiens GN = SELENBP1 PE = 1 SV = 2 - [SBP1_HUMAN] | -3.39 | 1.51E-05 | protein transport, allergic pulmonary eosinophilia, |
| P06396 | Gelsolin OS = Homo sapiens GN-GSN PE = 1 SV = 1 - [GELS_HUMAN] | 1.66 | 1.55E-05 | chemotaxis of leukocytes, phagocytosis, immune response of antigen presenting cells |
| Q16651 | Prostasin OS = Homo sapiens GN = PRSS8 PE = 1 SV = 1 - [PRSS8_HUMAN] | 5.98 | 1.88E-05 | proteolysis |
| Q13938 | Calcyphosin OS = Homo sapiens GN = CAPS PE = 1 SV = 1 - [CAYP1_HUMAN] | -1.58 | 1.98E-05 | intracellular signal transduction |
| O00468 | Agrin OS = Homo sapiens GN = AGRN PE = 1 SV = 5 - [AGRIN_HUMAN] | 6.27 | 2.00E-05 | glycosaminoglycan biosynthetic process, activation of leukocytes |
| P13987 | CD59 glycoprotein OS = Homo sapiens GN = CD59 PE = 1 SV = 1 - [CD59_HUMAN] | 4.99 | 2.56E-05 | regulation of complement activation, immune response, activation of mononuclear leukocytes |
| Q9NQ79 | Cartilage acidic protein 1 OS = Homo sapiens GN = CRTAC1 PE = 1 SV = 2 - [CRAC1_HUMAN] | 5.35 | 5.95E-05 | axonal fasciculation |
| P00568 | Adenylate kinase isoenzyme 1 OS = Homo sapiens GN = AK1 PE = 1 SV = 3 - [KAD1_HUMAN] | -5.77 | 7.20E-05 | nucleobase-containing compound metabolic process |

TABLE 3-continued

Differential proteome profile of tubal fluids from subjects with hydrosalpinx relative to lavages from healthy fertile donors.

| Accession | Protein identity | Log 2 Fold change | P-Adj | Biological Process |
|---|---|---|---|---|
| P08294 | Extracellular superoxide dismutase [Cu—Zn] OS = Homo sapiens GN = SOD3 PE = 1 SV = 2 - [SODE_HUMAN] | 5.1 | 7.47E-05 | response to reactive oxygen species, cellular infiltration by macrophages |
| P01034 | Cystatin-C OS = Homo sapiens GN = CST3 PE = 1 SV = 1 - [CYTC_HUMAN] | 3.66 | 1.15E-04 | chemotaxis of leukocytes, accumulation of neutrophils, response to hypoxia, apoptotic process |
| P02792 | Ferritin light chain OS = Homo sapiens GN = FTL PE = 1 SV = 2 - [FRIL_HUMAN] | 4.96 | 1.42E-04 | iron ion transport, inflammation, synovitis |
| Q8N2S1 | Latent-transforming growth factor beta-binding protein 4 OS = Homo sapiens GN = LTBP4 PE = 1 SV = 2 - [LTBP4_HUMAN] | 5.81 | 1.57E-04 | regulation of cell growth |
| P04083 | Annexin A1 OS = Homo sapiens GN = ANXA1 PE = 1 SV = 2 - [ANXA1_HUMAN] | -3.12 | 1.60E-04 | neutrophil homeostasis, adaptive immune response, monocyte chemotaxis, migration & accumulation of neutrophils, adhesion of neutrophil, inflammation of mucosa |
| P09466 | Glycodelin OS = Homo sapiens GN = PAEP PE = 1 SV = 2 - [PAEP_HUMAN] | 6.37 | 1.66E-04 | apoptotic process, regulation of interleukin-13 secretion, positive regulation of interleukin-6 secretion |
| P04075 | Fructose-bisphosphate aldolase A OS = Homo sapiens GN = ALDOA PE = 1 SV = 2 - [ALDOA_HUMAN] | -2.71 | 1.80E-04 | glycolytic process, tissue necrosis, inflammation of body cavity, body organ & joints |
| P15291 | Beta-1,4-galactosyltransferase 1 OS = Homo sapiens GN = B4GALT1 PE = 1 SV = 5 - [B4GT1_HUMAN] | 5.53 | 1.91E-04 | acute inflammatory response, chemotaxis of leukocytes, binding of neutrophils & professional phagocytic cells, epithelial cell development |
| P08123 | Collagen alpha-2(I) chain OS = Homo sapiens GN = COL1A2 PE = 1 SV = 7 - [CO1A2_HUMAN] | 3.25 | 2.25E-04 | skeletal system development, extracellular matrix organization, colitis |
| P54108 | Cysteine-rich secretory protein 3 OS = Homo sapiens GN = CRISP3 PE = 1 SV = 1 - [CRIS3_HUMAN] | 3.46 | 2.25E-04 | defense response, innate immune response |
| P08185 | Corticosteroid-binding globulin OS = Homo sapiens GN = SERPINA6 PE = 1 SV = 1 - [CBG_HUMAN] | 5.27 | 2.27E-04 | glucocorticoid metabolic process |
| P30044 | Peroxiredoxin-5, mitochondrial OS = Homo sapiens GN = PRDX5 PE = 1 SV = 4 - [PRDX5_HUMAN] | -5.31 | 3.37E-04 | response to reactive oxygen species, hydrogen peroxide catabolic process, inflammatory response |
| P30086 | Phosphatidylethanolamine-binding protein 1 OS = Homo sapiens GN = PEBP1 PE = 1 SV = 3 - [PEBP1_HUMAN] | -2.85 | 3.71E-04 | negative regulation of endopeptidase activity |
| P08758 | Annexin A5 OS = Homo sapiens GN = ANXA5 PE = 1 SV = 2 - [ANXA5_HUMAN] | -2.34 | 5.81E-04 | immune response leukocytes, phagocytosis, signal transduction, apoptotic process |
| P08603 | Complement factor H OS = Homo sapiens GN = CFH PE = 1 SV = 4 - [CFAH_HUMAN] | -1.62 | 6.22E-04 | regulation of complement activation, immune response of leukocytes, binding of neutrophils, phagocytosis |
| P05787 | Keratin, type II cytoskeletal 8 OS = Homo sapiens GN = KRT8 PE = 1 SV = 7 - [K2C8_HUMAN] | -5.07 | 7.21E-04 | tumor necrosis factor-mediated signaling pathway, cell differentiation involved in embryonic placenta development |
| P01024 | Complement C3 OS = Homo sapiens GN = C3 PE = 1 SV = 2 - [CO3_HUMAN] | 1.62 | 9.62E-04 | complement activation, inflammatory response |
| P61916 | Epididymal secretory protein E1 OS = Homo sapiens GN = NPC2 PE = 1 SV = 1 - [NPC2_HUMAN] | 5.12 | 0.001 | cholesterol metabolic process |
| P15328 | Folate receptor alpha OS = Homo sapiens GN = FOLR1 PE = 1 SV-3 - [FOLR1_HUMAN] | 5.17 | 0.001 | folic acid transport, cellular response to folic acid |
| P39060 | Collagen alpha-1(XVIII) chain OS = Homo sapiens GN = COL18A1 PE = 1 SV = 5 - [COIA1_HUMAN] | 5.45 | 0.002 | endothelial cell morphogenesis, extracellular matrix organization, accumulation of leukocytes |
| P21291 | Cysteine and glycine-rich protein 1 OS = Homo sapiens GN = CSRP1 PE = 1 SV = 3 - [CSRP1_HUMAN] | -4.5 | 0.002 | platelet aggregation |
| P61626 | Lysozyme C OS = Homo sapiens GN = LYZ PE = 1 SV = 1 - [LYSC_HUMAN] | 4.49 | 0.002 | inflammatory response, metabolic process, antibacterial response |
| P26038 | Moesin OS = Homo sapiens GN = MSN PE = 1 SV = 3 - [MOES_HUMAN] | 1.96 | 0.002 | movement of cell or subcellular component, leukocyte cell-cell adhesion |
| P62937 | Peptidyl-prolyl cis-trans isomerase A OS = Homo sapiens GN = PPIA PE = 1 SV = 2 - [PPIA_HUMAN] | -2.07 | 0.002 | protein peptidyl-prolyl isomerization, chemotaxis of monocytes |
| P13611 | Versican core protein OS = Homo sapiens GN = VCAN PE = 1 SV = 3 - [CSPG2_HUMAN] | 4.7 | 0.002 | skeletal system development |
| P08697 | Alpha-2-antiplasmin OS = Homo sapiens GN = SERPINF2 PE = 1 SV = 3 - [A2AP_HUMAN] | -1.96 | 0.003 | platelet degranulation, acute-phase response |

TABLE 3-continued

Differential proteome profile of tubal fluids from subjects with hydrosalpinx relative to lavages from healthy fertile donors.

| Accession | Protein identity | Log 2 Fold change | P-Adj | Biological Process |
|---|---|---|---|---|
| P08174 | Complement decay-accelerating factor OS = Homo sapiens GN = CD55 PE = 1 SV = 4 - [DAF_HUMAN] | 5.16 | 0.003 | complement activation, innate immune response |
| P02649 | Apolipoprotein E OS = Homo sapiens GN = APOE PE = 1 SV = 1 - [APOE_HUMAN] | 1.87 | 0.004 | cholesterol metabolic process, negative regulation of inflammatory response, response to reactive oxygen species |
| P51884 | Lumican OS = Homo sapiens GN = LUM PE = 1 SV = 2 - [LUM_HUMAN] | 3.31 | 0.004 | organismal Injury, axonogenesis |
| P01033 | Metalloproteinase inhibitor 1 OS = Homo sapiens GN = TIMP1 PE = 1 SV = 1 - [TIMP1_HUMAN] | 4.4 | 0.004 | cell activation, platelet degranulation, accumulation of macrophages |
| Q96C23 | Aldose 1-epimerase OS = Homo sapiens GN = GALM PE = 1 SV = 1 - [GALM_HUMAN] | -4.47 | 0.005 | carbohydrate metabolic process, chitin catabolic |
| P05186 | Alkaline phosphatase, tissue-nonspecific isozyme OS = Homo sapiens GN = ALPL PE = 1 SV-4 - [PPBT_HUMAN] | 4.91 | 0.006 | skeletal system development |
| P03973 | Antileukoproteinase OS = Homo sapiens GN = SLPI PE = 1 SV = 2 - [SLPI_HUMAN] | 2.45 | 0.006 | innate immune response, antibacterial humoral response |
| P49747 | Cartilage oligomeric matrix protein OS = Homo sapiens GN = COMP PE = 1 SV = 2 - | 5.22 | 0.006 | skeletal system development, apoptotic process |
| P12277 | Creatine kinase B-type OS = Homo sapiens GN = CKB PE = 1 SV = 1 - [KCRB_HUMAN] | -3.21 | 0.006 | creatine metabolic process, immune response of cells, phagocytosis |
| Q9HC84 | Mucin-5B OS = Homo sapiens GN = MUC5B PE = 1 SV = 3 - [MUC5B_HUMAN] | 4.7 | 0.006 | regulation of macrophage activation, antibacterial response, O-glycan processing |
| P54652 | Heat shock-related 70 kDa protein 2 OS = Homo sapiens GN = HSPA2 PE = 1 SV = 1 - [HSP72_HUMAN] | -1.6 | 0.008 | response to unfolded protein, regulation of cell death |
| P04792 | Heat shock protein beta-1 OS = Homo sapiens GN = HSPB1 PE = 1 SV = 2 - [HSPB1_HUMAN] | -1.73 | 0.009 | oxidative stress-induced intrinsic apoptotic signaling pathway, response to unfolded protein, cell movement |
| P41222 | Prostaglandin-H2 D-isomerase OS = Homo sapiens GN = PTGDS PE = 1 SV = 1 - [PTGDS_HUMAN] | 4.69 | 0.009 | prostaglandin biosynthetic process, accumulation of granulocytes |
| P11142 | Heat shock cognate 71 kDa protein OS = Homo sapiens GN = HSPA8 PE = 1 SV = 1 - [HSP7C_HUMAN] | -1.54 | 0.011 | response to unfolded protein |
| P02794 | Ferritin heavy chain OS = Homo sapiens GN = FTH1 PE = 1 SV = 2 - [FRIH_HUMAN] | 4.51 | 0.014 | iron ion transport, immune response, oxidation-reduction process |
| Q06828 | Fibromodulin OS = Homo sapiens GN = FMOD PE = 1 SV = 2 - [FMOD_HUMAN] | 4.36 | 0.014 | complement activation |
| Q8NBJ4 | Golgi membrane protein 1 OS = Homo sapiens GN = GOLM1 PE = 1 SV = 1 - [GOLM1_HUMAN] | 4.23 | 0.014 | nucleus organization |
| Q7L266 | Isoaspartyl peptidase/L-asparaginase OS = Homo sapiens GN = ASRGL1 PE = 1 SV = 2 - [ASGL1_HUMAN] | -3.11 | 0.014 | proteolysis |
| P08571 | Monocyte differentiation antigen CD14 OS = Homo sapiens GN = CD14 PE = 1 SV = 2 - [CD14_HUMAN] | 3.28 | 0.014 | apoptotic process, inflammatory response, activation of leukocytes, production of ROS |
| P55058 | Phospholipid transfer protein OS = Homo sapiens GN = PLTP PE = 1 SV = 1 - [PLTP_HUMAN] | 4.29 | 0.014 | lipid transport, inflammatory response, binding of neutrophils, sperm motility |
| P35241 | Radixin OS = Homo sapiens GN = RDX PE = 1 SV = 1 - [RADI_HUMAN] | 1.56 | 0.014 | regulation of cell shape |
| P60174 | Triosephosphate isomerase OS = Homo sapiens GN = TPI1 PE = 1 SV = 3 - [TPIS_HUMAN] | -1.5 | 0.014 | gluconeogenesis, canonical glycolysis |
| P20061 | Transcobalamin-1 OS = Homo sapiens GN = TCN1 PE = 1 SV = 2 - [TCO1_HUMAN] | 4.79 | 0.015 | cobalt ion transport |
| PODMV9 | Heat shock 70 kDa protein 1B OS = Homo sapiens GN = HSPA1B PE = 1 SV = 1 - [HS71B_HUMAN] | -1.5 | 0.016 | regulation of cell death, cellular response to oxidative stress |
| P09871 | Complement C1s subcomponent OS = Homo sapiens GN = C1S PE = 1 SV = 1 - [C1S_HUMAN] | 1.87 | 0.017 | complement activation, innate immune response |
| P23526 | Adenosylhomocysteinase OS = Homo sapiens GN = AHCY PE = 1 SV = 4 - [SAHH_HUMAN] | -4 | 0.018 | sulfur amino acid metabolic process, chronic inflammatory response to antigenic stimulus, response to hypoxia |
| O43866 | CD5 antigen-like OS = Homo sapiens GN = CD5L PE = 1 SV = 1 - [CD5L_HUMAN] | -2.75 | 0.019 | inflammatory response, apoptotic process, recruitment of phagocytes |
| POCOL4 | Complement C4-A OS = Homo sapiens GN = C4A PE = 1 SV = 2 - [CO4A_HUMAN] | 1.59 | 0.019 | complement activation, inflammatory response, activation of leukocytes |

TABLE 3-continued

Differential proteome profile of tubal fluids from subjects with hydrosalpinx relative to lavages from healthy fertile donors.

| Accession | Protein identity | Log 2 Fold change | P-Adj | Biological Process |
|---|---|---|---|---|
| P07900 | Heat shock protein HSP 90-alpha OS = Homo sapiens GN = HSP90AA1 PE = 1 SV = 5 - [HS90A_HUMAN] | -1.69 | 0.019 | protein folding, immune response of antigen presenting cells |
| P09429 | High mobility group protein B1 OS = Homo sapiens GN = HMGB1 PE = 1 SV = 3 - [HMGB1_HUMAN] | -4.29 | 0.019 | activation of innate immune response, regulation of tolerance induction |
| P07225 | Vitamin K-dependent protein S OS = Homo sapiens GN = PROS1 PE = 1 SV = 1 - [PROS_HUMAN] | 4.46 | 0.019 | leukocyte migration, regulation of complement activation |
| Q8IZP2 | Putative protein FAM10A4 OS = Homo sapiens GN = ST13P4 PE = 5 SV = 1 - [ST134_HUMAN] | -3.75 | 0.021 | NA |
| P00441 | Superoxide dismutase [Cu-Zn] OS = Homo sapiens GN = SOD1 PE = 1 SV = 2 - [SODC_HUMAN] | -1.52 | 0.022 | response to reactive oxygen species, ovarian follicle development |
| P0COL5 | Complement C4-B OS = Homo sapiens GN = C4B PE = 1 SV = 2 - [CO4B_HUMAN] | 0.86 (NS) | 0.023 | complement activation, inflammatory response |
| Q14103 | Heterogeneous nuclear ribonucleoprotein D0 OS = Homo sapiens GN = HNRNPD PE = 1 SV = 1 - [HNRPD_HUMAN] | -3.87 | 0.023 | mRNA splicing, via spliceosome |
| Q99497 | Protein DJ-1 OS = Homo sapiens GN = PARK7 PE = 1 SV = 2 - [PARK7_HUMAN] | -2.29 | 0.027 | inflammatory response, cellular response to oxidative stress, hydrogen peroxide metabolic process, protein stabilization |
| P06702 | Protein S100-A9 OS = Homo sapiens GN = S100A9 PE = 1 SV = 1 - [S10A9_HUMAN] | 3.28 | 0.027 | leukocyte migration involved in inflammatory response, neutrophil chemotaxis, accumulation of macrophages |
| P43353 | Aldehyde dehydrogenase family 3 member B1 OS = Homo sapiens GN = ALDH3B1 PE = 1 SV = 1 - [AL3B1_HUMAN] | 4.28 | 0.028 | alcohol metabolic process, cell death, necrosis, cellular response to oxidative stress |
| P00736 | Complement C1r subcomponent OS = Homo sapiens GN = C1R PE = 1 SV = 2 - [C1R_HUMAN] | 2.87 | 0.028 | complement activation, immune response |
| P04406 | Glyceraldehyde-3-phosphate dehydrogenase OS = Homo sapiens GN = GAPDH PE = 1 SV = 3 - [G3P_HUMAN] | -1.94 | 0.028 | glycolytic process, apoptotic process, DNA repair |
| P30041 | Peroxiredoxin-6 OS = Homo sapiens GN = PRDX6 PE = 1 SV = 3 - [PRDX6_HUMAN] | -2.06 | 0.029 | response to reactive oxygen species, hydrogen peroxide catabolic process |
| P06454 | Prothymosin alpha OS = Homo sapiens GN = PTMA PE = 1 SV = 2 - [PTMA_HUMAN] | -2.95 | 0.029 | transcription |
| P52943 | Cysteine-rich protein 2 OS = Homo sapiens GN = CRIP2 PE = 1 SV = 1 - [CRIP2_HUMAN] | -3.17 | 0.032 | positive regulation of cell proliferation |
| P05154 | Plasma serine protease inhibitor OS = Homo sapiens GN = SERPINA5 PE = 1 SV = 3 - [IPSP_HUMAN] | 2.79 | 0.038 | lipid transport |
| O00560 | Syntenin-1 OS = Homo sapiens GN = SDCBP PE = 1 SV = 1 - [SDCB1_HUMAN] | 4.24 | 0.039 | negative regulation of receptor internalization |
| P10599 | Thioredoxin OS = Homo sapiens GN = TXN PE = 1 SV = 3 - [THIO_HUMAN] | -2.33 | 0.039 | response to reactive oxygen species, hydrogen peroxide catabolic process |
| Q7Z7G0 | Target of Nesh-SH3 OS = Homo sapiens GN = ABI3BP PE = 1 SV = 1 - [TARSH_HUMAN] | 4.38 | 0.04 | extracellular matrix organization |
| P05109 | Protein S100-A8 OS = Homo sapiens GN = S100A8 PE = 1 SV = 1 - [S10A8_HUMAN] | 3.94 | 0.046 | leukocyte migration involved in inflammatory response, neutrophil chemotaxis, chronic inflammatory response |
| P29401 | Transketolase OS = Homo sapiens GN = TKT PE = 1 SV = 3 - [TKT_HUMAN] | -2.28 | 0.046 | xylulose biosynthetic process |
| P22626 | Heterogeneous nuclear ribonucleoproteins A2/B1 OS = Homo sapiens GN = HNRNPA2B1 PE = 1 SV = 2 - [ROA2_HUMAN] | -3.75 | 0.047 | transcription from RNA polymerase II promoter |
| P27169 | Serum paraoxonase/arylesterase 1 OS = Homo sapiens GN = PON1 PE = 1 SV = 3 - [PON1_HUMAN] | -1.94 | 0.048 | response to toxic substance, response to reactive oxygen species |

What is claimed is:

1. A method comprising:
    detecting, by quantitative ELISA, a presence of mesothelin in a plasma sample from a subject;
    identifying the subject as having hydrosalpinx if the sample comprises
        an increased level of mesothelin relative to a control, or comprises a level of mesothelin corresponding to a hydrosalpinx control;
        and
    administering a hydrosalpinx therapy to the subject, wherein the hydrosalpinx therapy comprises sclerotherapy, surgical removal or excision of all or a part of a fallopian tube, fallopian tube dilation, or removal of fallopian adhesion.

2. A method of treating a subject suffering from infertility, comprising:
    determining whether the subject has hydrosalpinx by detecting the presence of an increased mesothelin level in a plasma sample from the subject relative to a control; or comprises a level of mesothelin corresponding to a hydrosalpinx control, wherein detecting comprises conducting a quantitative ELISA;
    administering a hydrosalpinx therapy to the subject, wherein the hydrosalpinx therapy comprises sclerotherapy, fallopian tube dilation, or removal of fallopian adhesion; and administering a fertility treatment after the administering of the hydrosalpinx therapy.

* * * * *